US007135337B2

(12) United States Patent
Grigliatti et al.

(10) Patent No.: US 7,135,337 B2
(45) Date of Patent: Nov. 14, 2006

(54) INSECT EXPRESSION VECTORS

(76) Inventors: Tom A. Grigliatti, 4157 Staulo Crescent, Vancouver, B.C. (CA) V6N 3S1; Tom A. Pfeifer, 1007-1330 Hardwood Street, Vancouver, B.C. (CA) V6E 1S8; David A. Theilmann, R.R. #4 S99 C38, 6622 Nixon Road, Summerland, B.C. (CA) V0H 1Z0; Dwayne D. Hegedus, 205-2700 Acadia Road, Vancouver, B.C. (CA) V6T 1R9

( * ) Notice: Subject to any disclaimer, the term of this patent is extended or adjusted under 35 U.S.C. 154(b) by 140 days.

(21) Appl. No.: 09/896,888

(22) Filed: Jun. 29, 2001

(65) Prior Publication Data
US 2002/0116723 A1 Aug. 22, 2002

Related U.S. Application Data

(63) Continuation of application No. 09/048,911, filed on Mar. 26, 1998, now abandoned.

(60) Provisional application No. 60/049,946, filed on Mar. 27, 1997.

(30) Foreign Application Priority Data

Jan. 28, 1998 (CA) .................................... 2221819

(51) Int. Cl.
C12N 5/16 (2006.01)
C12N 15/85 (2006.01)

(52) U.S. Cl. ..................................... 435/348; 435/320.1
(58) Field of Classification Search ............... 435/69.1, 435/325, 7.1, 320.1, 252.3; 536/23.1
See application file for complete search history.

(56) References Cited

U.S. PATENT DOCUMENTS 5,077,214 A 12/1991 Guarino et al.
5,179,007 A 1/1993 Jarvis et al.

FOREIGN PATENT DOCUMENTS

EP 0 756 007 A2 1/1997
WO WO 88/03169 5/1988
WO WO 95/09923 4/1995

OTHER PUBLICATIONS

Theilmann et al., Virology 187, 84-96, 1992.*
Luckow and Summers, Bio/Tech., 6:47-55, 1988.
Miller, Annu. Rev. Microbiol., 42:177-199, 1988.
Guarino and Summers, J. Virol., 62:463-471, 1988.
Miller et al., Virology, 126:376-380, 1983.
Carbonell et al., J. Virol., 56:153-160, 1985.
Lenhard et al., Gne, 169:187-190, 1996.
Kidd and Emery, Appl. Biochem. Biotechnol., 42:137-159, 1993.
Anderson et al., Biochem. J., 280:219-224, 1991.
Chazenbalk and Rapoport, J. Biol. Chem., 270:1543-1549, 1995.
Hsu et al., Prot. Expr. Purif., 5:595-603, 1994.
Li et al., Virology, 204:266-278, 1994.
Kretzchmar et al., J. Biol. Chem., 375:323-327, 1994.
Jarvis and Finn, Virology, 212:500-511, 1995.
Jarvis and Finn, Nature Biotechnology, 14:1288-1292, 1996.
Jarvis et al., Prot. Expr. Purif., 8:191-203, 1996.
Johansen et al., Genes Develop., 3:882-889, 1989.
Culp et al., Bio/Technology, 9:173-177, 1991.
Shotkoski et al., FEBS Lett., 380:257-262, 1996.
Jarvis et al., Bio/Technology, 8:950-955, 1990.
Leisy et al., Virology, 208:742-752, 1995.
Glocker et al., J. Virol., 66:3476-3484, 1992.
Rodems and Friesen, J. Virol., 69:5368-5375, 1995.
Carlson et al., Annu. Rev. Entomol., 40:359-388, 1995.
Bourouis and Jarry, EMBO J., 2:1099-1104, 1983.
Shotkoski and Fallon, Insect Biochem. Molec. Biol., 23:883-893, 1993.
Rio and Rubin, Mol. Cell. Biol., 5:1833-1838, 1985.
Maisonhaute and Echailier, FEBS Lett., 197:45-49, 1986.
Lycett and Crampton, Gene, 136:129-136, 1993.
McGrane et al., Am. J. Trop. Med. Hyg., 39:502-510, 1988.
Monroe et al., Proc. Natl. Acad. Sci. USA, 89:5725-5729, 1992.
Mulsant et al., Somat. Cell Mol. Genet., 14:243-252, 1988.
Invitrogen Corporation ApZeoSV2(+) or pZeoSV2(-)@ product manual, Version C, San Diego, CA, U.S.A.
Krappa and Knebel-Morsdorf, J. Virol., 65:805-812, 1991.
Carson et al., J. Virol., 65:945-951, 1991.
Devereux et al., Nucl. Acids Res., 12:387-395, 1984.
Mismer and Rubin, Genetics, 116:565-578, 1987.
Cartier et al., J. Virol., 68:7728-7737, 1994.
Theilman and Stewart, Virology, 187:84-96, 1992.
Blochinger and Digglemann, Mol. Cell. Biol., 4:2929-2931, 1984.
Kovach et al., Insect Mol. Biol., 1:37-43, 1992.
Berger and Rudolph, Invertebrate Cell System Applications, CRC Press, Inc., Boca Raton, FL (1989).

(Continued)

Primary Examiner—Nancy Vogel
(74) Attorney, Agent, or Firm—Scully, Scott, Murphy & Presser, P.C

(57) ABSTRACT

The invention provides insect shuttle vectors, and methods of using such vectors, for stably transforming disparate insect cell lines to express heterologous proteins. The invention provides a transformed insect cell selection system based on resistance to the bleomycin/phleomycin family of antibiotics, including the antibiotic Zeocin. Efficient promoters derived from baculovirus immediate early promoters are disclosed for use in directing expression of heterologous proteins, including selectable markers, in transformed insect cells of the invention. Transposon-based vectors are disclosed that provide inducible transposition to optimize heterologous protein expression and unobtrusive markers to facilitate selection of desired transformants.

19 Claims, 27 Drawing Sheets

OTHER PUBLICATIONS

Chalfie et al., *Science*, 263:802-805, 1994.
Mackett et al., *J. Virol.*, 49:857-864, 1984.
Neumann et al., *BioTechniques*, 5:444-448, 1987.
Food et al., *J. Biol. Chem.*, 269:3034-3040, 1994.
Jefferies et al., *Brain Res.*, 712:122-126, 1996.
Meredith et al., *J. Exp. Biol.*, 199:1053-1061, 1996.
Pritchard et al., *Mol. Gen. Genet.*, 214:533-540, 1988.
Meister and Grigliatti, *Genome*, 36:1169-1175, 1993.
Kaufman et al., *Cell*, 59:359-371, 1988.
Sass, *Gene*, 89:179-186, 1990.
Morris and Miller, *J. Virol.*, 66:7397-7405, 1992.
Kogan and Blissard, *J. Virol.*, 68:813-822, 1994.
Kogan et al., *J. Virol.* 69:1452-1461, 1995.
Pullen and Friesen, *J. Virol.*, 69:156-165, 1995.
Krappa et al., *J. Virol.*, 66:3494-3503, 1992.
Dickson and Friesen, *J. Virol.*, 65:4006-4016, 1991.
Nissen and Friesen, *J. Virol.*, 63:493-503, 1989.
Guarino et al., *J. Virol.*, 60:224-229, 1986.
Choi and Guarino, *J. Virol.*, 69:4548-51, 1995.
O'Reilly et al., Baculovirus Expression Vectors, W.H. Freeman and Company, New York, NY, USA, 27-46, 98-103, 237-240, 1992.
Jarvis, Insect Cell Culture Engineering, Marcel Dekker, Inc., New York, NY, USA 195-219, 1993.
Walker, *Adv. Cell Culture*, 7:87-124, 1989.
Steller and Pirotta, *EMBO J.*, 4:167-171, 1985.
Berdy, Handbook of Antibiotic Compounds, vol. IV, Part 1. Amino Acid and Peptide Antibiotics, CRC Press, Boca Raton, FL, USA, 459-497, 1980.
Gatignol et al., *FEBS Lett.*, 230:171-175, 1988.
Perez et al., *Plant Mol. Biol.*, 13:365-373, 1989.
Miller, Experiments in Molecular Genetics, Cold Spring Harbor Laboratory, Cold Spring Harbor, NY, USA, 277-318, 1972.
Meyer, *TIBTECH*, 13:332-337, 1995.
Sambrook et al., Molecular Cloning: A Laboratory Manual, Cold Spring Harbor, NY 9.44, 9.42, 5.73-5.81, 5.84.
Brown et al., *Proc. Natl. Acad. Sci. USA*, 78:539-543, 1981.
Audsley et al., *J. Exp. Biol.*, 173:261-274, 1992.
Theilmann and Stewart, *Virology*, 187:97-106, 1992.
van der Straten et al., Invertebrate Cell System Applications, CRC Press Inc., Boca Raton, FL 183-195, 1989.
Blissard and Rohrmann, *Virology*, 170:537-555, 1989.
Carson et al., *Virology*, 65:945-951, 1991.
O'Brochta et al., J. of Cell. Biochemistry—Keystone Symposia Suppl., 21A: 195, 1995.
McNagny et al., *Blood*, 87:1343-1352, 1996.
Kennard et al., *Biotechnol. Bioeng.*, 42:480-486, 1993.
Davie et al., *Adv. Enzymol. Relat. Areas Mol. Biol.* 48:277-318, 1979.
Coronado C. et al., "Use of Firefly Luciferase Gene for Plasmid Copy Number Determination", *Plasmid*, 1994, 32:336-341.

* cited by examiner

Figure 2b

```
                                      -225  -221R -191  -162  -157R -101  -89   -76   -34
A       C  T  T  A  T  C  G  G
B                T  T  A  T  C  G  G  .  G  A  C  A  G  A  C  G  C
C                T  T  A  T  C  C  G  G     A  A  C  A  G  A  C  G  C
D                T  T  A  T  C  G  T  G     A  C [C] A  G  A  C  G  C
E                T  T  A  T  C  G  G  A     A  A  A  G  A  C  G  C
F                T  T  A  T  C  C  G  G     A  A  C  A  G  A  C  G  C
G                T  T  A  T  C  G  G  A     A  A  G [A] G  A  C  G  C
H                T  T  A  T  C  G  G  A     A  C  A  G  A  C  G  C
I                                              
Consensus       C  T  T  A  T  C  G  G  -    A  C  A  G  G  A  C  C  G
         -232  -212R -197  -175  -147R -118  -93   -80   -40
```

Figure 12b

5' P-element rescue pDM79
    CGACGGGACCACCTTATGTTATTTCATCATG<u>GGCCAGAC</u>CCACGTAGTCCAGCGGC...

79-2 Xho.6
    CGACGGGACCACCTTATGTTATTTCATCATG<u>TCTCGAAC</u>CAACGAGAGCAGTATGC...

79-2 Xho.4
    CGACGGGACCACCTTATGTTATTTCATCATG<u>GTACAGAC</u>ATCTACTTCCCCCCGCT...

79-1 Sph.1
    CGACGGGACCACCTTATGTTATTTCATCATG<u>ATCTTGCG</u>CTTTAAAATGTGGAGTC...

3' P-element rescue pDM79
    CGACGGGACCACCTTATGTTATTTCATCATG<u>GTCTGGCC</u>ATTCTCATCGTGAGCTT...

79-2 kan.3
    CGACGGGACCACCTTATGTTATTTCATCATG<u>AGCCAAAC</u>AGAAAGCAGAAAAGCTC...

79-2 kan.2
    CGACGGGACCACCTTATGTTATTTCATCATG<u>GCCTGACC</u>TAAGCAGATTTGACTGC...

79-2 kan.1
    CGACGGGACCACCTT                      <u>CAACGCTA</u>CCTAATCTTAAGAACCA...

consensus
                                                          GNCYRRAC

Figure 16b

INSECT EXPRESSION VECTORS

This is a continuation of U.S. patent application Ser. No. 09/048,911, filed Mar. 26, 1998 now abandoned, which in turn claims the benefit of U.S. Provisional Patent Application No. 60/049,946, both of which are incorporated herein by reference in their entirety.

FIELD OF THE INVENTION

The invention is in the field of vectors for genetic engineering. The invention relates to vectors for directing expression of heterologous proteins in transformed cells, particularly in stably transformed insect cells, methods for using such vectors and cells transformed with such vectors.

BACKGROUND OF THE INVENTION

The transformation of cultured cells with foreign DNA sequences is useful in the study of gene expression and in the production of commercially important heterologous gene products, such as valuable proteins. Simple proteins may be produced in bacterial cells. However, to function properly, many eukaryotic proteins require post-translational modifications that are not carried out by prokaryotic cells. There are other problems associated with expressing some proteins in prokaryotic cells; for example, some expressed heterologous proteins are deposited as insoluble inclusion bodies in prokaryotic cells, making the proteins difficult to recover. Many of the difficulties associated with prokaryotic expression systems may be overcome by using transformed mammalian cell culture systems to produce post-translationally processed proteins. Mammalian cell cultures may, however, be relatively inefficient because they grow slowly and are difficult and costly to maintain.

Advances in the culture of insect cells, and the development of baculovirus-based expression systems, have facilitated the expression of heterologous proteins by transformed insect cell lines (Luckow and Summers, Bio/Tech., 6: 47–55 (1988); Miller, Annu. Rev. Microbiol., 42: 177–199 (1988)). To date, the expression of heterologous proteins in transformed insect cell lines has been accomplished primarily using vectors derived from the baculovirus Autographa californica multicapsid nucleopolyhedrosis virus (AcMNPV) (Luckow and Summers, Bio/Tech., 6: 47–55 (1988); Miller, Annu. Rev. Microbiol., 42: 177–199 (1988)). Baculoviruses are double-stranded DNA viruses that kill infected insect cells by lysis at the end of a typical infection cycle. A variety of baculoviruses are known, each of which is endemic to a particular arthropod species. Baculoviruses are not known to undergo replication in animals outside the Arthropoda. An understanding of the prior art in this field requires some appreciation of the molecular biology of baculovirus infection.

Gene expression during natural baculovirus infection of an insect is highly regulated and occurs as an ordered cascade. The viral genes may be classified into four different groups according to their place in this cascade of gene expression: immediate early (ie), delayed early (de), late, and very late. Early gene expression occurs before the onset of viral DNA replication and appears to be essential for the induction of late viral gene expression (Blissard and Rohrmann, Annu. Rev. Entomol., 35: 127–155 (1990); Guarino and Summers, J. Virol., 62: 463–471(1988); Miller et al., Virology, 126: 376–380 (1983)). Experimental evidence indicates that baculovirus ie genes are transcribed by host RNA polymerase II in the absence of other viral factors. Baculovirus ie genes are therefore understood to have promoters that are recognized by the host cell transcription machinery.

In prior art expression systems based on derivatives of the AcMNPV, foreign gene expression is generally directed by a very strong late viral promoter, such as the polyhedrin (pol) or p10 promoters. Expression from such baculovirus late promoters is, however, dependent upon viral-encoded RNA polymerase for transcription and is restricted to permissive lepidopteran cells, ie. cells that permit lytic baculovirus infection (Carbonell et al., J. Virol., 56: 153–160 (1985)). A wide array of baculovirus expression vectors have been designed to optimize expression, secretion and recovery of recombinant proteins produced by such systems (O'Reilly et al., Baculovirus Expression Vectors, W. H. Freeman and Company, New York, N.Y., USA (1992); U.S. Pat. No. 5,179,007 to Jarvis and Carrington; Lenhard et al., Gene, 169: 187–190 (1996)). Many post-translational modifications known to occur in mammalian systems, including N- and O-linked glycosylation, phosphorylation, acylation, proteolysis (Kidd and Emery, Appl. Biochem. Biotechnol., 42: 137–159 (1993)) and amidation (Andersons et al., Biochem. J., 280: 219–224 (1991)) also occur, at least to some degree, in insect cell lines infected with derivatives of the AcMNPV.

Using A cMNPV-based expression systems, proteins localized to the nucleus or cytoplasm may be expressed in adequate quantities (U.S. Pat. No. 5,179,007 to Jarvis et al. issued 12 Jan. 1993). Proteins entering the secretory pathway associated with the endoplasmic reticulum are, however, often expressed at lower levels (Jarvis, Insect Cell Culture Engineering, Marcel Dekker, Inc, New York, N.Y., USA (1993)). This subset of highly modified, membrane-bound and secreted proteins includes important bioactive species such as cell surface receptors (Chazenbalk and Rapoport, J. Biol. Chem., 270: 1543–1549 (1995)), antibodies (Hsu et al., Prot. Expr. Purif, 5: 595–603 (1994)) and secreted vaccine components (Li et al., Virology, 204: 266–278 (1994)). Proteins of this kind are frequently expressed relatively poorly and in a heterogeneous form in lytic AcMNPV-based systems. Reduced expression levels and alterations in processing may be the result of damage to the infected cells normal protein expression machinery caused by the progression of the lytic baculovirus infection (Kretzchmar et al., J. Biol. Chem., 375: 323–327 (1994); Jarvis and Finn, Virology, 212: 500–511 (1995); Chazenbalk and Rapoport, J. Biol. Chem., 270: 1543–1549 (1995)). Accordingly, research has been directed toward the generation of baculovirus vectors capable of expressing proteins early in the infection cycle (Jarvis and Finn, Nature Biotechnology, 14: 1288–1292 (1996); Jarvis et al., Prot. Expr. Purif., 8: 191–203 (1996)).

To overcome the problems associated with lytic baculovirus expression systems, approaches have been developed for the stable transformation of insect cell lines. Drosophila melanogaster Schneider cells have been stably transformed with a system that utilizes the D. melanogaster metallothionein promoter to drive heterologous protein expression and hygromycin selection to identify transformants (Johansen et al., Genes Develop., 3: 882–889 (1989); Culp et al., Bio/Technology, 9: 173–177 (1991)). Dipteran cell lines (D. melanogaster and Aedes albopictus, mosquito) have been stably transformed with a system that utilizes the D. melanogaster hsp70 or AcMNPV ie1 promoters to drive heterologous protein expression and methotrexate selection to identify transformants (Shotkoski et al., FEBS Lett., 380: 257–262 (1996)). A lepidopteran cell line (Sf9, derived from the fall army worm *Spodoptera frugiperda*) has been stably transformed with a system that utilizes the AcMNPV ie1 promoter to drive heterologous protein expression and geneticin (G-418) selection to identify transformants, although expression in this system was found to be relatively inefficient (Jarvis et al., *Bio/Technology,* 8: 950–955 (1990); U.S. Pat. No. 5,077,214 issued to Guarino and Jarvis on 31 Dec. 1991). In each of these transformation systems, the selectable marker on one vector was cotransfected with a separate expression vector carrying the heterologous protein expression cassette. Using separate plasmids that must be cotransfected complicates the transformation procedure, since some of the cell lines that acquire the selectable marker will not also acquire the desired expression vector. There is accordingly a need in the art for vectors capable of providing both a selectable marker and an expression cassette.

There is also a need in the art for strong promoters to direct expression of heterologous proteins in stably transformed insect cells. In an attempt to meet this need, the hr enhancer element has been used to increase expression from the Ac ie1 promoter (Shotkoski et al., *FEBS Lett.,* 380: 257–262 (1996)). The hr enhancer exists as five large homologous regions dispersed throughout the AcMNPV baculovirus genome and serve to activate transcription of proximal genes (Leisy et al., *Virology,* 208: 742–752 (1995)). However, difficulties may arise with the use of hr elements in transformation systems because specific cellular or baculovirus-encoded factors may be required to modulate the action of hr elements (Glocker et al., *J. Virol.,* 66: 3476–3484 (1992); Choi and Guarino, *J. Virol.,* 69: 4548–4551 (1995); Rodems and Friesen, *J. Virol.,* 69: 5368–5375 (1995)). Also, adding enhancer sequences to a promoter may significantly increase the size of the promoter, necessarily leaving less room in the relevant vector for the heterologous gene of interest. There is therefore a need in the art for promoters that are capable of directing adequate levels of heterologous protein expression, including selectable marker expression, without the need for enhancer sequences.

Transposable elements have been used as transformation vectors in a number of organisms. Transposable elements are mobile segments of DNA that are characterized by the ability to autonomously replicate and insert themselves in a variety of locations within the cell's genome. There are two distinctly different classes of transposable elements: 1) the short inverted repeat class of DNA transposons ("DNA transposable elements"); and, 2) the retrotransposons which replicate through an RNA intermediate and require reverse transcriptase activity for transposition (such as are disclosed in International Patent Publication Number WO 88/03169). One aspect of the present invention relates to the short inverted repeat class of DNA transposable elements, as distinguished from retrotransposons.

A complete DNA transposable element encodes a transposase enzyme that mediates transposition of the element. The transposase protein interacts with DNA sequences near the termini of the element; intact termini (usually about 150 to 250 base pairs) are typically required to allow DNA transposable elements to respond to the transposase enzyme.

The DNA transposable elements, P, hobo, mariner, I, and Hermes (a hobo-like mobile element from *Musca domestica*) have all been used to transform the fruit fly, *D. melanogaster* (O'Brochta, et al., *J. of Cell. Biochemistry-Keystone Symposia Suppl.,* 21A: 195 (1995); Pritchard, et al., *Mol. Gen. Genet.,* 214: 533–540 (1988)). Large pieces of foreign DNA (>12 kb) can be placed within non-coding regions of the P element and not hinder its ability to replicate through transposition (Meister and Grigliatti, *Genome,* 36: 1169–1175 (1993)). The DNA transposable element Tc1 has been used to transform the round worm *Caenorhabdites elegans*. The selection of desired transformants is an important step in any transformation system. While several transformation systems based upon auxotrophic complementation or dominant selection have been designed for use in mammalian systems, relatively few have been adapted for insect cells (Walker, *Adv. Cell Cult.,* 7: 87–124 (1989); Carlson et al., *Annu. Rev. Entomol.,* 40: 359–388 (1995)). The transformation of *D. melanogaster* cells to methotrexate resistance using a bacterial dihydrofolate reductase (DHFR) gene was first described by Bourouis and Jarry, *EMBO J.,* 2: 1099–1104 (1983). Subsequently, Shotkoski and Fallon, *Insect Biochem. Molec. Biol.,* 23: 883–893 (1993) described a mosquito dihydrofolate reductase gene that functioned as a dominant selectable marker in mosquito cells. In these instances the transforming DNA was incorporated into the genome as repetitive structures and as randomly integrated single copies; however, in the absence of selective pressure a loss of transfecting DNA was observed (Shotkoski and Fallon, *Insect Biochem. Molec. Biol.,* 23: 883–893 (1993)). Resistance to geneticin (G418) after introduction of the bacterial neomycin phosphotransferase gene, can be endowed upon both *D. melanogaster* (Steller and Pirotta, *EMBO J.,* 4: 167–171 (1985)) and its derivative cell lines (Rio and Rubin, *Mol. Cell. Biol.,* 5: 1833–1838 (1985)), mosquitoes (Maisonhaute and Echalier, *FEBS Lett.,* 197: 45–49 (1986); Lycett and Crampton, *Gene,* 136: 129–136 (1993)) and the Sf9 lepidopteran cell line (Jarvis et al., *Bio/Tech.,* 8: 950–955 (1990)). However, gene amplification arising from continued selection and high spontaneous resistance frequencies (McGrane et al., *Am. J. Trop. Med Hyg.,* 39: 502–510 (1988) undermine the use of this selection system in certain instances. Hygromycin resistance provided by the bacterial hygromycin B phosphotransferase gene is reported to be more reliable, and selection more rapid, than in G418-based selection systems (van der Straten et al., Invertebrate Cell System Applications, CRC Press Inc., Boca Raton, Fla., USA (1989); Carlson et al., *Annu. Rev. Entomol.,* 40: 359–388 (1995)). However, in mosquito cell lines transformed for hygromycin resistance, the introduced plasmid was amplified extensively and was present as long tandem arrays or as self-replicating extra chromosomal pseudo-chromosomes (Monroe et al., *Proc. Natl. Acad. Sci. USA,* 89: 5725–5729 (1992)). Either genetic arrangement, tandem arrays or extra chromosomal elements, lends itself to rapid loss of the resistance gene once selection has been relaxed. Accordingly, there is a need for an improved selection system and strategy for efficient insertion of DNA into the host cells' genome, particularly for use in selecting stably transformed insect cells.

Zeocin is a member of the bleomycin/phleomycin family of antibiotics isolated from *Streptomyces verticillus* (Berdy, Handbook of Antibiotic Compounds, Vol IV, Part 1. Amino Acid and Peptide Antibiotics, CRC Press, Boca Raton, Fla., USA (1980)). Zeocin is a trademark of S.A.R.L. Cayla of Toulouse, France, from whom it may be available. Zeocin is a copper-chelated glycopeptide of the formula $C_{55}H_{83}N_{19}O_{21}S_2Cu$.

Resistance to the bleomycin/phleomycin family of antibiotics may be conferred by a 3.6 kDa protein, the product of the *Streptoalloteichus hindustanus ble* gene, that binds the antibiotic in a stoichiometric manner (Gatignol et al., *FEBS Lett.,* 230: 171–175 (1988)). The ble resistance gene has been successfully used in mammalian (Mulsant et al., *Somat. Cell Mol. Genet.,* 14: 243–252 (1988)) and plant cells (Perez et al., *Plant Mol. Biol.*, 13:365–373 (1989)) to confer Zeocin resistance. The effect the bleomycin/phleomycin antibiotics on cells derived from other genera is unpredictable.

A number of potential difficulties are associated with the use of Zeocin as a selectable marker. The copper-chelated form of the drug is inactive. The current incomplete understanding of the mechanism of action of the Zeocin suggests that activation only occurs if appropriate conditions are encountered within the target cell to reduce the chelated copper from $Cu^{2+}$ to $Cu^{1+}$, so that the copper ion may be removed by sulfydryl compounds in the cell. High salt concentrations may inactivate Zeocin. The drug may also be inactivated by acidic or basic solutions (Invitrogen Corporation "pZeoSV2(+) or pZeoSV2(−)" product manual, Version C, San Diego, Calif., U.S.A.).

Insect cell expression systems are of interest in large part because of their ability to accomplish sophisticated post translational modifications. However, there may be variability from one cell line to another in the nature of the precise post translational modification to a protein of interest. Accordingly, it may be useful to screen a number of transformed insect cell lines from disparate species to determine which cell line best expresses the protein of interest. To accomplish such a screening procedure, there is a need in the art for an expression vector capable of stably transforming a range of insect cell lines to strongly express heterologous proteins.

SUMMARY OF THE INVENTION

An aspect of the present invention involves the use of Zeocin as a selection system in insect cell lines. The use of Zeocin resistance as a selection system may provide important, unpredicted advantages over prior art insect selection systems. These advantages may include: relatively low concentrations of the antibiotic may be required for selection (resulting in reduced cell culture costs); the same selection scheme is effective in both eukaryotic and prokaryotic systems (so that the vector need carry only one resistance gene, minimizing the size of the vector); and, the small size of the ble resistance gene (374 bp) allows for the development of compact cloning vectors (again, minimizing the size of the vector and thereby maximizing the vector's capacity to incorporate heterologous sequences); another indirect advantage is that the availability of Zeocin resistance selection systems in accordance with this invention adds to the repertoire of alternative selection schemes for use with insect cells. The use of alternative selection systems may be particularly useful, for example, when multiple constructs are introduced either collectively or sequentially into a specific host cell, each such construct utilizing a different selection system. An additional advantage flowing from the relatively compact Zeocin selection system is the possibility of adding unobtrusive reporter gene sequences to vectors of the invention, such as β-galactosidase or green fluorescent protein genes.

One aspect of the present invention involves the use of promoters derived from a baculovirus immediate early promoter to control expression of a selectable marker gene that confers resistance to one of the family of bleomycin/phleomycin-type antibiotics. In one aspect, the selectable marker gene may be the *Streptoalloteichus hindustanus ble* gene which is shown herein to confer Zeocin resistance on insect cells. The ie1 and ie2 promoters derived from the *Orgyia pseudotsugata* multicapsid nucleopolyhedrosis virus (OpMNPV) ie1 and ie2 genes may be operably linked to the selectable marker gene to control transcription from the selectable marker gene. The promotor may comprise sequences homologous to portions of the OpMNPV ie2 promoter, particularly those portions that include a sequence motif designated as an IE2B element or a paired GATA-IE2B element.

An aspect of the invention is an expression vector that includes a multiple cloning site to enable an inserted coding sequence to be operably linked to a baculovirus immediate-early promoter. This expression vector may be used with another vector that confers a selection advantage on an insect cell line, for the purpose of constructing a stable insect cell line producing a heterologous protein.

In one aspect, shuttle vectors of the invention may include a multiple cloning site or a heterologous coding sequence operably linked to a baculovirus immediate early promoter. In accordance with this aspect of the invention, promoters homologous to the OpMNPV ie1 or ie2 promoters may be used to drive expression of heterologous genes in transformed dipteran and lepidopteran cell lines.

A compact shuttle vector is disclosed comprising a chimeric Op ie-synthetic bacterial promoter that may direct expression of a Zeocin resistance gene in insect cell lines and in *E. coli*, to allow selection of both eukaryotic and prokaryotic transformants. A series of versatile expression vectors is disclosed that use the OpMNPV ie2 promoter for constitutive heterologous protein expression in a broad range of dipteran and lepidopteran insect cells. In some aspects, vectors of the invention comprise the *D. melanogaster* metallothionein (Mtn) promoter for metal-inducible protein expression in dipteran cell lines. Other aspects of the invention comprise the use of modified lacI/O or tet components for inducible protein expression in insect cells.

Unexpected advantages associated with use of the Op ie2 promotor are disclosed, such as function in a broad range of insect cell hosts, restricted expression in non-insect cell lines, high levels of expression in the absence of enhancer-like sequences and cryptic prokaryotic promoter functionality.

Aspects of the invention include cells lines transformed for the constitutive and inducible expression of heterologous genes, including the highly processed glycosylphosphatidylinositol-anchored glycoprotein, human melanotransferrin, secreted Factor X, and the secreted ion transport peptide hormone (ITP) in transformed insect cell lines.

Vectors of the invention may comprise unobtrusive reporter genes, such as β-galactosidase or green fluorescent protein (GFP) coding genes, useful to assess protein production capability in transformed cell lines and to thereby facilitate the recovery of clonal cell lines or cell populations expressing high levels of heterologous protein. These unobtrusive reporter genes can be linked via inframe protein fusions to the antibiotic resistance gene such as Zeocin resistance, thus allowing analysis and selection of cell lines via both antibiotic resistance and/or FACS.

Vectors of the invention may include a transposon-based protein expression cassette comprising transposable elements defining a transposon, the selectable marker gene and/or heterologous protein coding sequences being within the transposon. Such vectors may be introduced into cell lines having a source of transposase. Several mechanisms are disclosed to provide a source of the transposase. In one embodiment, a transgenic insect cell line is induced to provide transposase from an inducible genomic transposase gene. When transposase is expressed, the enzyme directs the entry of the transposon into the genomic DNA. While transposase is expressed, the number of copies of the transposon-based expression cassette may increase over time via replicative transposition of the cassette to new genomic sites. Transposase expression may be modulated to regulate movement of the transposon, thereby controlling transposon copy number. The level of expression of specific heterologous proteins may be optimized by optimizing the copy number of transposon-based expression cassettes that a cell line carries.

In one aspect of the invention, a P transposon-based expression cassette may be used to transform SL2 cell lines. The vector may comprise the P element inverted repeat transposon termini defining a transposon, and within the transposon: an inducible transposase gene (to control movement), a selectable marker (to select only transformed cells) and a heterologous protein expression cassette (which may include a multiple cloning site). In an alternative embodiment, the transposase gene may be integrated stably into the genome of the cell line. Alternatively, the transposase gene may be incorporated into a transformation helper plasmid which provides transposase to mediate integration, but is itself unable to integrate into the genome by transposition.

The invention includes an SL2 cell line with the P transposase gene integrated into the genome, in which the transposase gene has the third intron removed (Δ2-3) which allows transposase to be active in somatic cells. In this embodiment, the Δ2-3 transposase gene is under the control of the metallothionein (Mtn) promoter (the cell line being designated SL2MTAΔ2-3) so that transposase expression may be induced.

In certain embodiments, the elements of the transposase vector of the invention may combine to provide a mechanism for easily identifying transformants (such as Zeocin resistance), a mechanism for inducing an increase in the number of stably integrated copies of the vector (inducible transposase), and a mechanism for easily identifying clones with the potential for increased heterologous protein expression (an unobtrusive marker that is indicative of heterologous sequence copy number). In effect, the novel combination of structural features in such vectors work together to provide important functional advantages at various stages in the production of heterologous proteins from transformed insect cells.

BRIEF DESCRIPTION OF THE DRAWINGS

FIG. 2b. Alignment of the repeated sequences of the IE2B promoter elements. The position of the elements relative to the ie2 transcriptional start site is indicated by the numbers. The elements that are in reverse orientation have an R designation. The location of repeats A through I as shown in FIG. 2b are identified by bracketed reference letters in FIG. 2a.

Figure 8A:
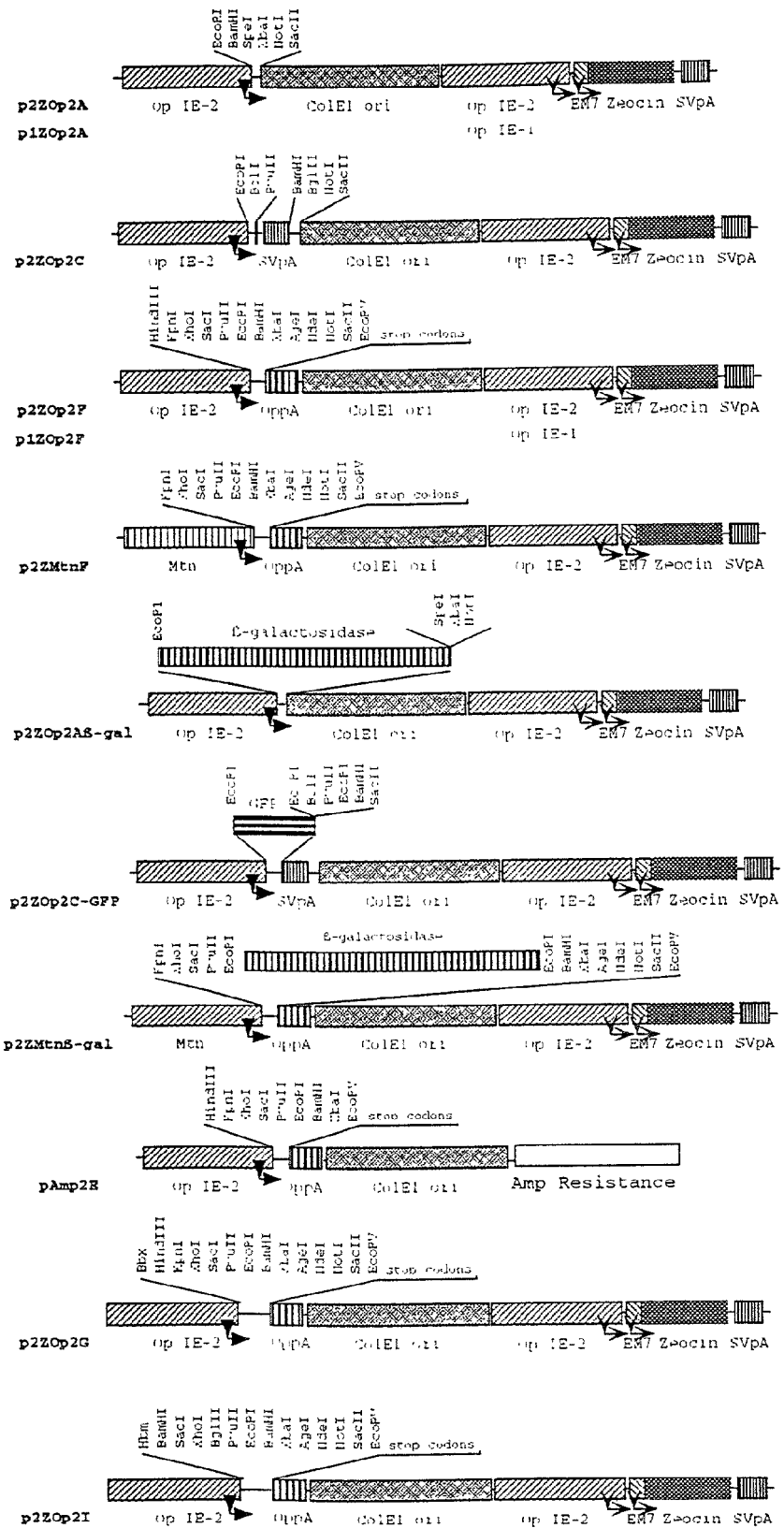
FIG. 8a. Insect cell line protein expression vectors containing a Zeocin resistance gene shuttle cassette. Each plasmid is designated by an acronym whereby: p, plasmid; 1Z/2Z, ie1 or ie2 promoter directing expression of the Zeocin resistance gene; Op2, ie2 promoter in the protein expression cassette; Mtn, D. melanogaster metallothionein promoter in the protein expression cassette; A, no pA signal sequence; C, SV40 early gene pA signal sequence; F, ie2 gene pA signal sequence; Bbx, bombyxin secretion signal; Hbm, Honey bee mellatin secretion signal. Constructs are not drawn to scale.
Figure 8B:
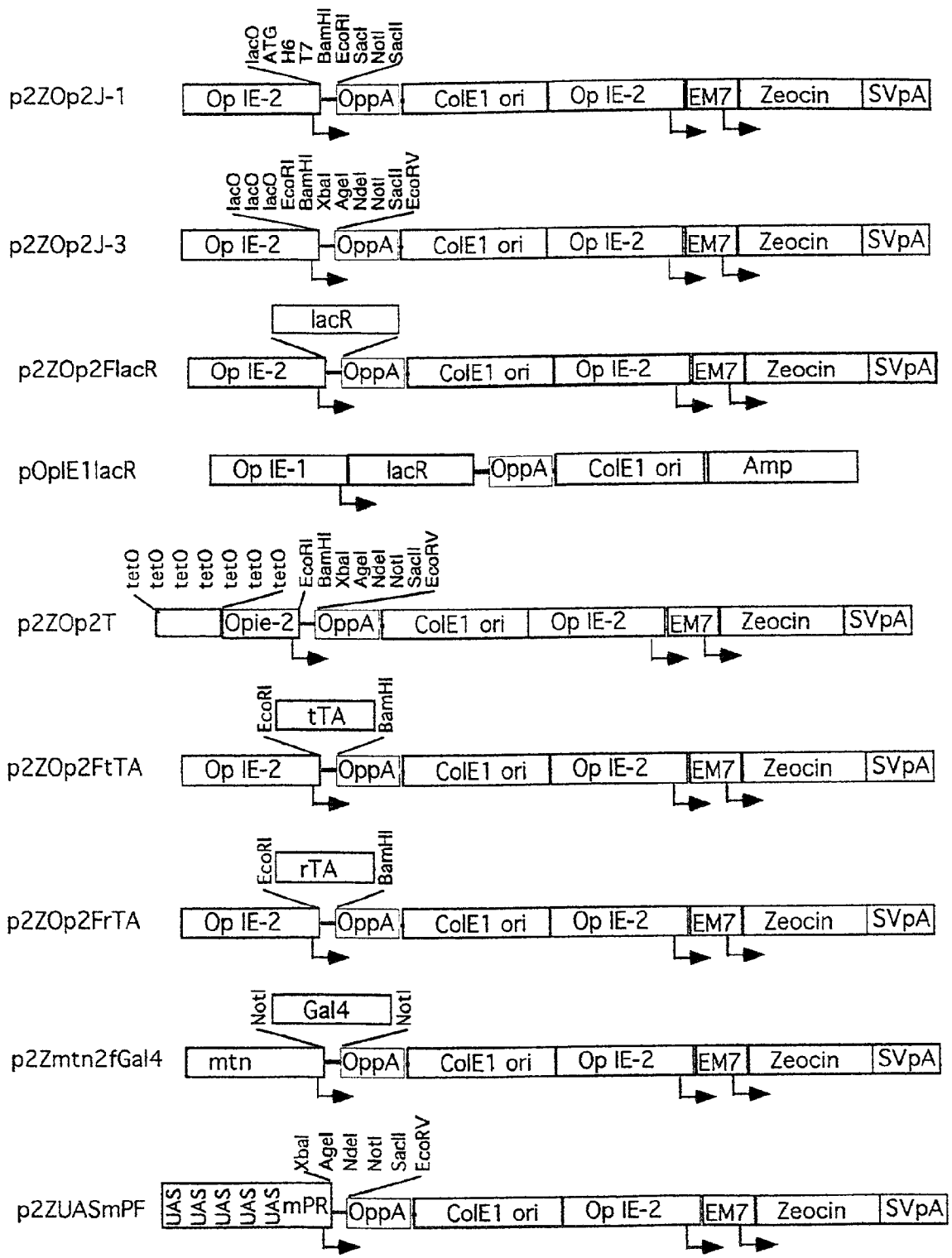

FIG. 8b. Specialized insect cell line expression vectors. Constructs are not drawn to scale lacO, lac Operator sequence; H6, six histidine amino acids; T7, sequence identified by T7 polymerase; lacR, fragment encoding the lacI gene and a nuclear localization signal; tetO, tetracycline operator sequence; tTA, tetracycline transcriptional activator; rTA, reverse tetracycline transcriptional activator; UAS, upstream activator sequence. Other designations are the same as in FIG. 8a.

Figure 9:
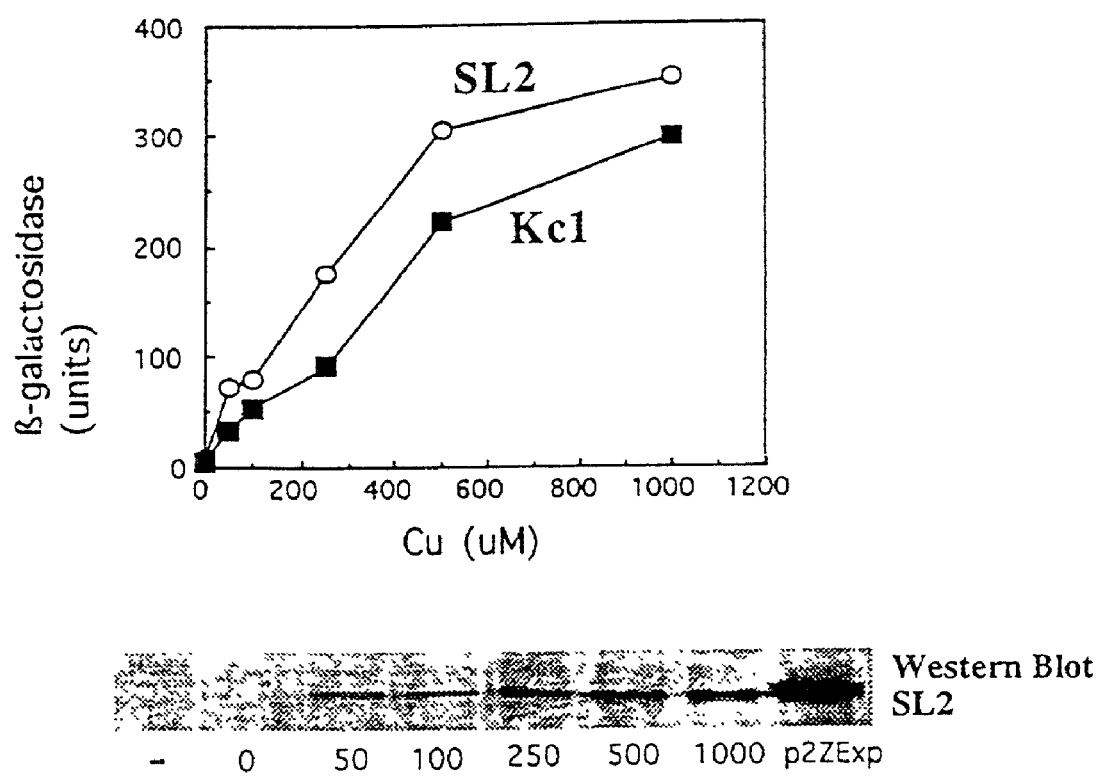

FIG. 9. Induction of β-galactosidase activity with $CuSO_4$ in D. melanogaster Kc1 and SL2 cell lines transiently transformed with either p2ZMtnFβ-Gal or p2ZOp2Aβ-Gal; reporter gene constructs. Panel A shows enzymatic activity present in the cell pellet and Panel B the corresponding western blot analysis.

Figure 10:
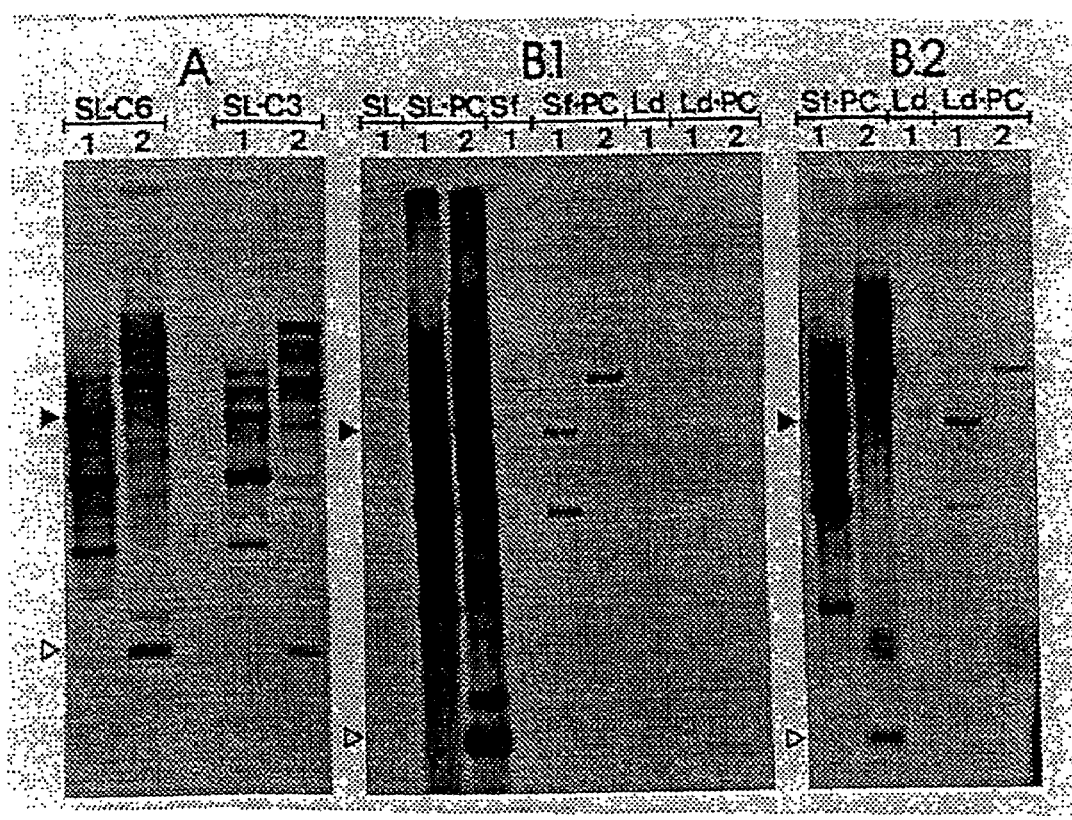

FIG. 10. Genomic Southern blot analysis of stable, clonal and polyclonal insect cell lines transformed with the pZOp2Aβ-Gal reporter construct. Lanes containing DNA from clonal SL2 lines are designated by SL-C.# and polyclonal cells lines by -PC. Cell line DNA in each lane is as follows: Sf, Spodoptera fiugiperda Sf9; Ld, Lymantria dispar (gypsy moth) Ld652Y; and SL, D. melanogaster SL2. Lanes containing DNA from non-transformed SL2 (SL), Sf9 (Sf) and Ld652y (Ld) are as indicated. Lanes 1 and 2 refer to EcoRI or PstI-SalI-digested DNA, respectively. Panel B.2 is a longer exposure of a portion of panel B.1 to enhance bands in the Sf-PC and Ld-PC lanes. Arrowheads in the left margin indicate the position of the β-galactosidase (lane 1) and Zeocin resistance genes (lane 2).

Figure 11:
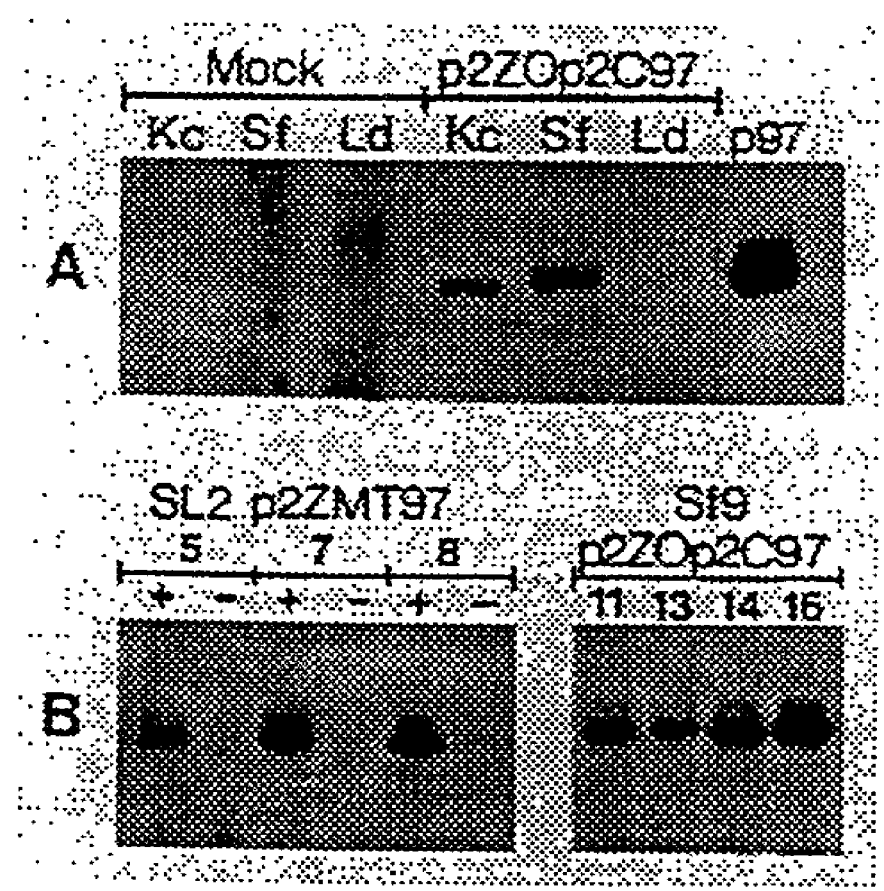

FIG. 11. Western blot analysis of human melanotransferrin (p97) expressed transiently (Panel A) or in stably transformed (Panel B) insect cell lines after transformation with either Mtn (p2ZMtn97), +/− induction with 500 μM $CuSO_4$, or ie2 (p2ZOp2C97) promoter-p97 gen constructs. Cell line protein in each lane is as follows: Kc, D. melanogaster KC1; Sf, S. frugiperda Sf9; Ld, L. dispar Ld652Y; and SL, D. melanogaster SL2. The p97 control lane contains semi-purified baculovirus-expressed p97 protein.

Figure 12A:
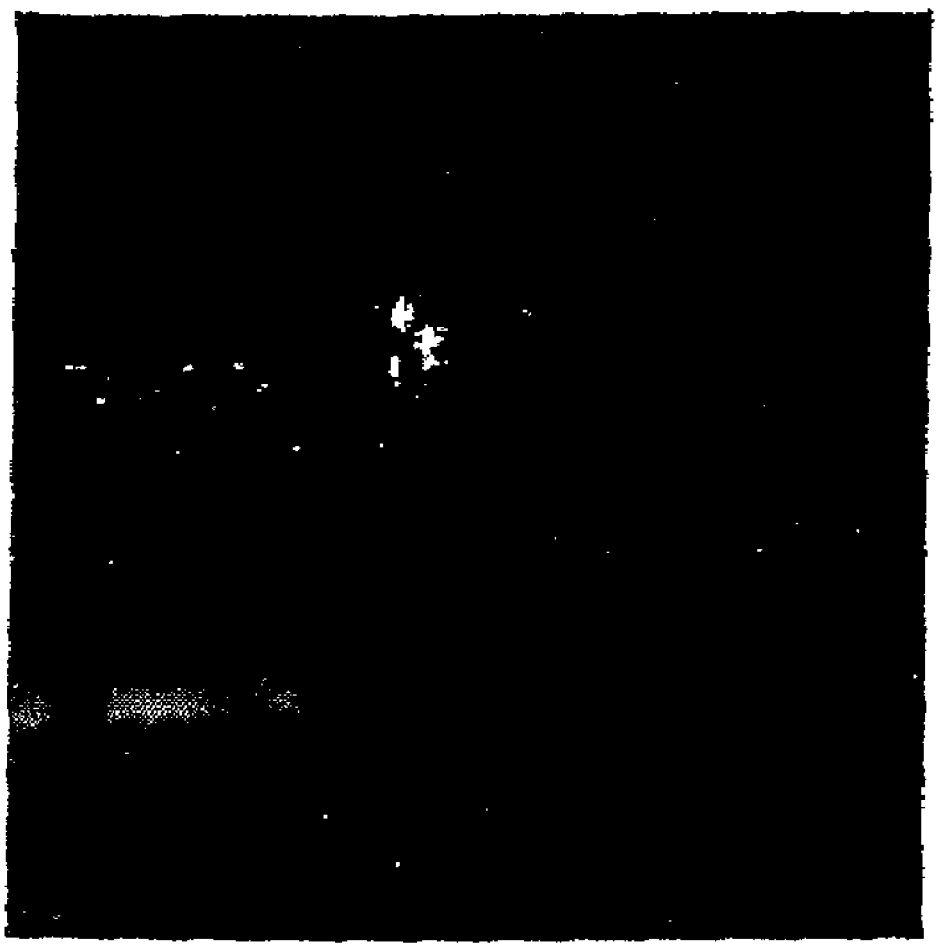

FIG. 12a. Immunofluorescence localization of the recombinant human melanotransferrin (p97) on the surface of transformed Sf9 cells.

FIG. 12b. Deletion constructs made of the melanotransferrin (p97) gene and compared with the native p97 construct as well as the chicken homologues.

Figure 12C:
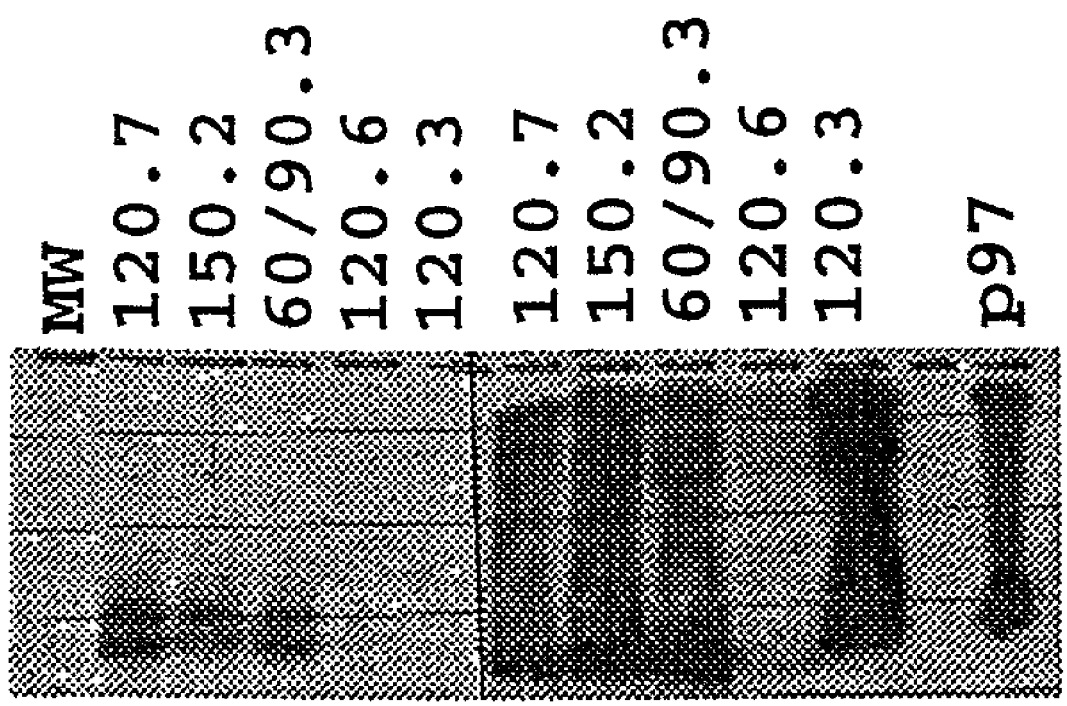

FIG. 12c. Western blot analysis of p97 deletion constructs. The left side of the blot contains pellet samples while the right side of the blot contains the corresponding supernatant samples. Sample 120.6 is present in the supernatant sample.

Figure 12D:
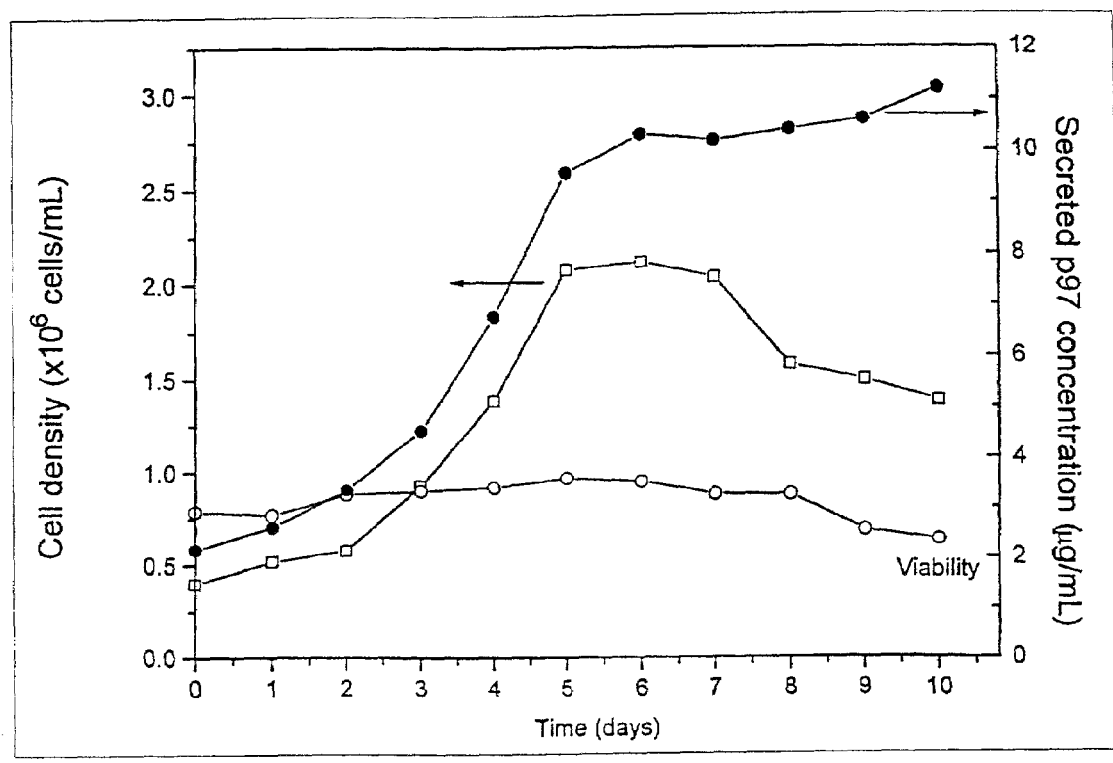

FIG. 12d. Production of secreted p97 during growth of the deletion construct 120.6 grown in a 100 ml spinner flask. Viability utilizes the left side vertical axis where 1 is equal to 100%.

Figure 12E:
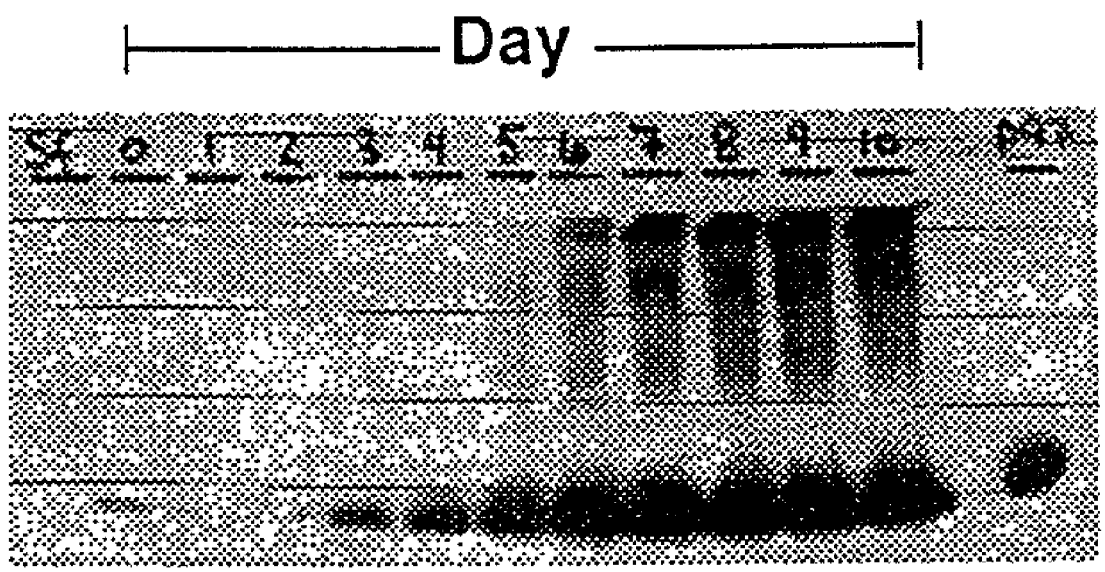

FIG. 12e. Western blot analysis of superatant samples taken during the growth phase of the deletion construct 120.6 in FIG. 12d. Sf, negative control; p97, positive control.

Figure 13A:
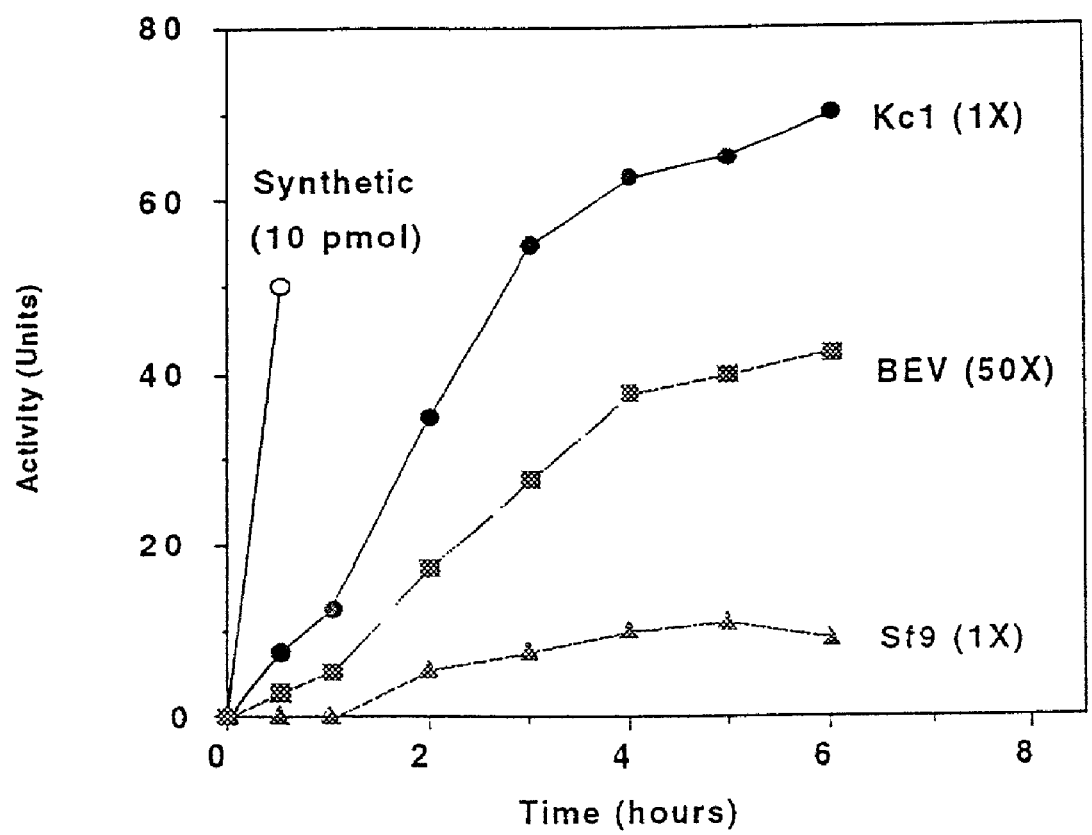

FIG. 13a. Biological activity of recombinant ion transport peptide expressed in various insect cell lines or baculovirus. The amount of supernatant used in the assays is indicated in brackets.

Figure 13B:
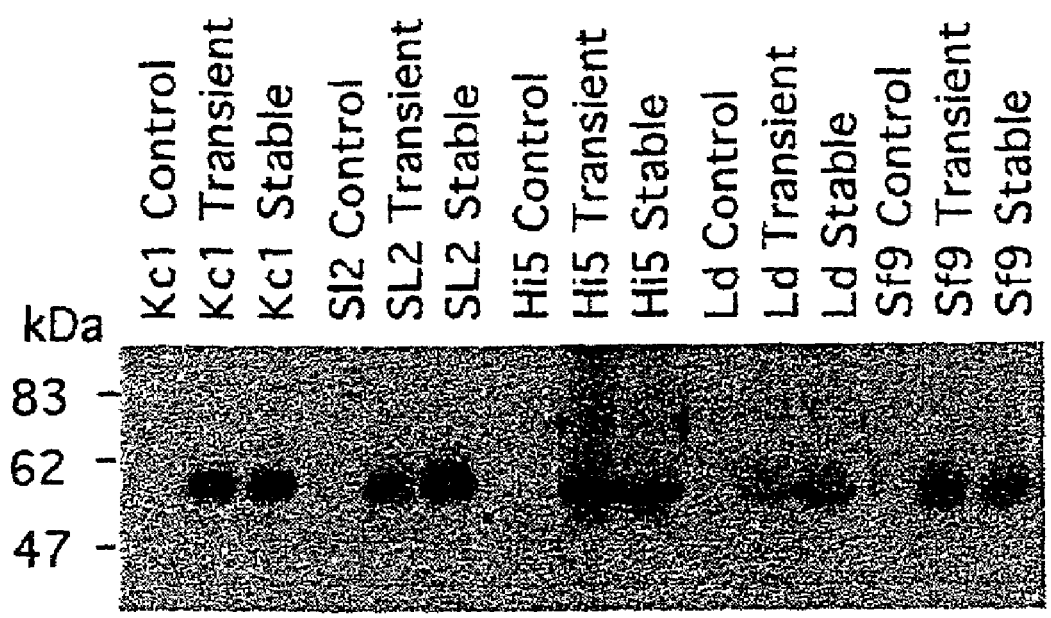

FIG. 13b. Western blot analysis of supernatant samples taken from transiently or stable polyclonal cell lines transformed with the Factor X constructs.

Figure 14:
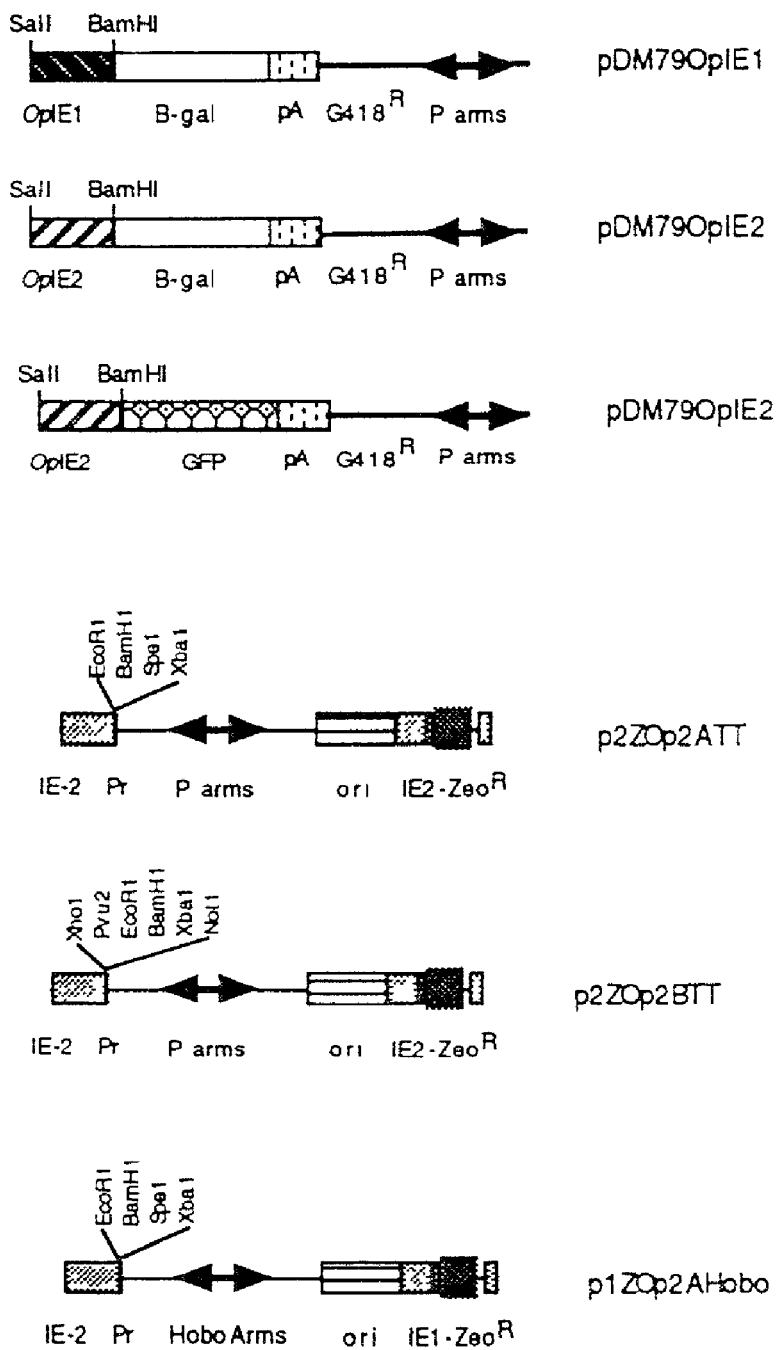

FIG. 14. Transposon-based vectors for the expression of proteins in insect cell lines. Arrowheads indicate direction of inverted repeats.

Figure 15:
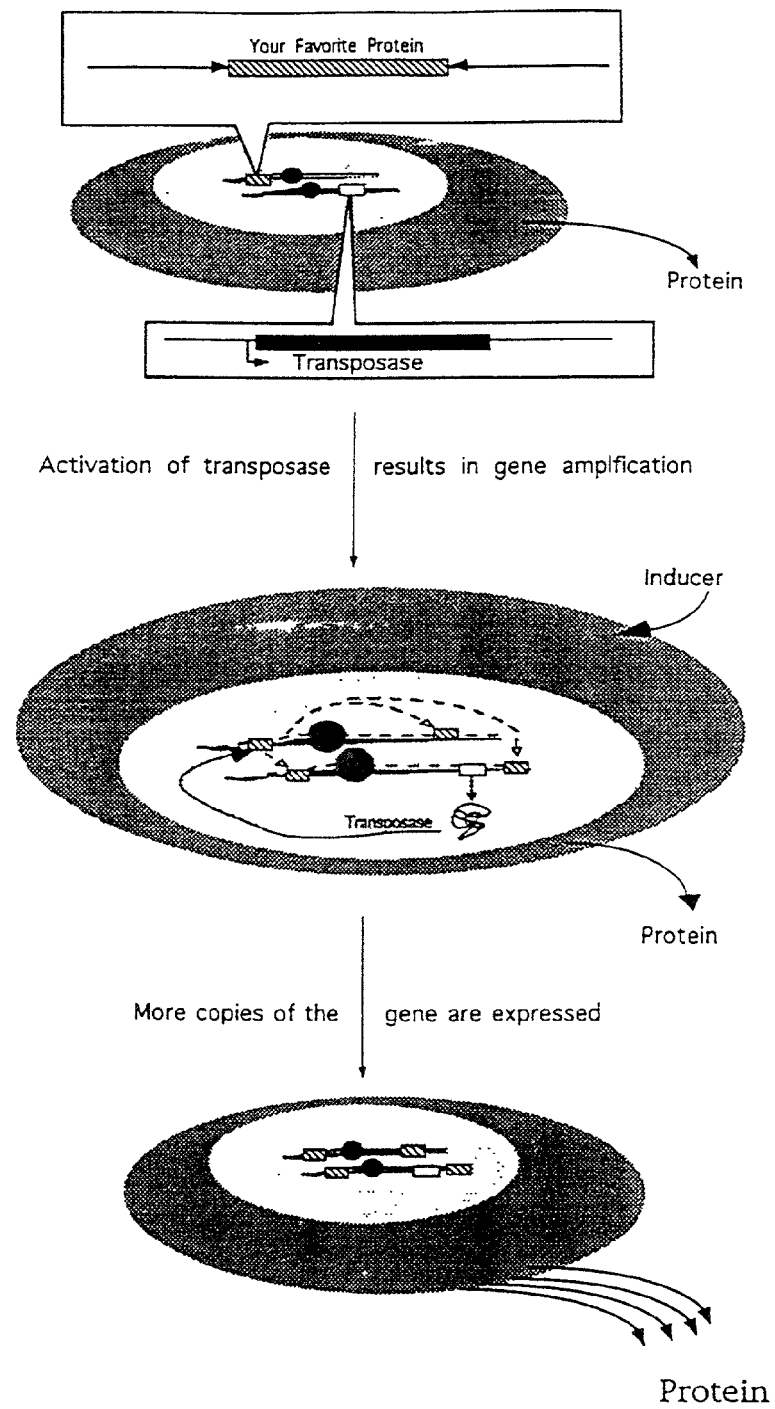

FIG. 15. Schematic representation of the transposon-based protein expression cassette introduction and amplification system.

Figure 16A:
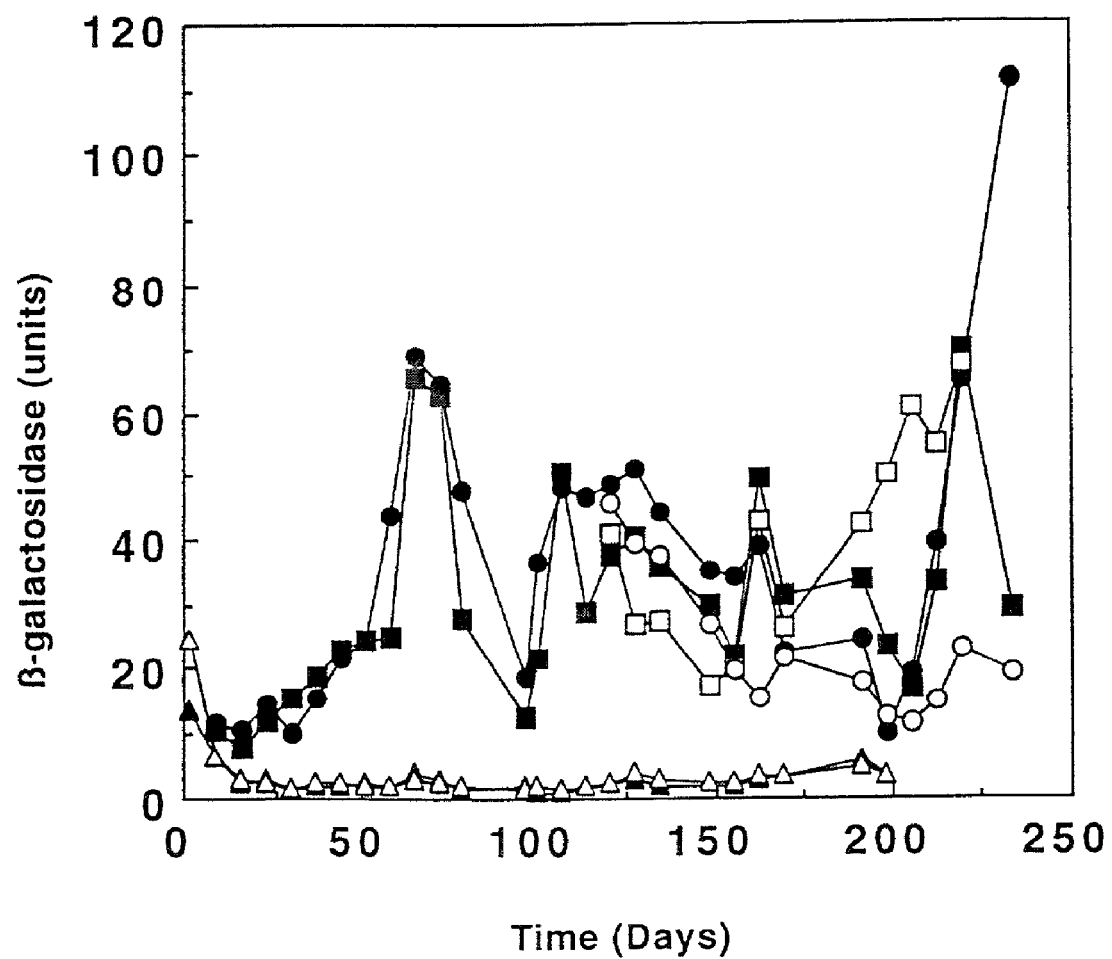

FIG. 16a. Continual expression of β-galactosidase by SL2 MTΔ2-3 polyclonal cell lines transformed with the P transposon-based reporter vector pDM79OPIE2 over a period of several months. Transposase production was induced by exposure to 250 μM $CuSO_4$ prior to transformation. Subsequently the cells were collected by centrifugation, transformed and placed on unsupplemented TC-100+7.5% fetal bovine serum medium (-Δ-) or medium containing 100 $CuSO_4$ (-▲-), 100 $CuSO_{4+1}$ mg/ml G-418 (-■-) or 1 mg/ml G-418 (-●-). After 18 weeks the G-418 resistant cell lines were split and cultured in the presence (-■-,-●-) or absence (-□-, -o-) of antibiotic selective pressure.

FIG. 16b. Sequences of rescued P-element ends from a stable cell line transformed with the vector pDM79IE-2. The bold sequences are vector sequences, while the normal type is chromosomal DNA from the cell line. The underlined segment is the 8 bp duplicated region. None of the chromosomal or non-P sequences are from the original vector, demonstrating that a transposition event has occured.

Figure 17:
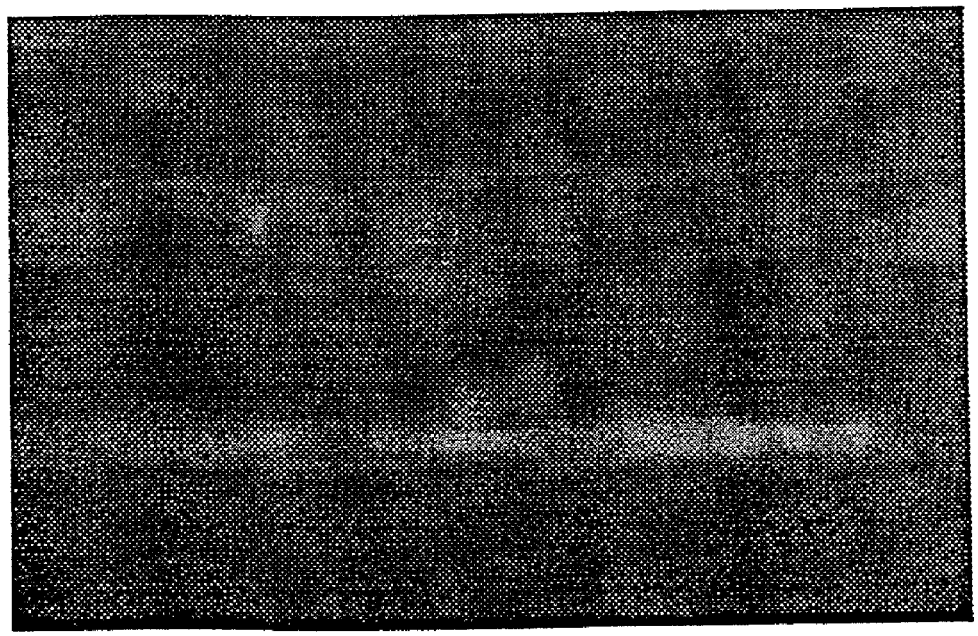

FIG. 17. Expression of green fluorescent protein by an SL2 MTΔ2,3 polyclonal cell line transformed with the P transposon-based reporter vector, pDM79IE2GFP.

DETAILED DESCRIPTION

Effect of Zeocin on Growth and Viability of Insect Cell Lines

The dipteran (D. melanogaster) cell lines Kc1 and SL2, and the lepidopteran cell lines Sf9 (S. frugiperda), Ld652Y (L. dispar) and Cf1 (Choristoneura fumeferana) were tested for sensitivity to Zeocin in order to establish whether Zeocin was toxic in standard culture conditions to cell lines from these disparate insect orders. Zeocin is thought to exert its toxic effects by binding to DNA to induce double strand breaks. Such strand cleavage is thought to inhibit growth by disruption of DNA replication, which in turn interferes with subsequent cell division. Accordingly, cells already committed to division would not be expected to be affected by Zeocin until the next round of DNA replication; it would therefore be expected that cells treated with Zeocin may divide once, but will be unable to undergo further mitotic divisions since their DNA will not be intact.

Figure 4A:
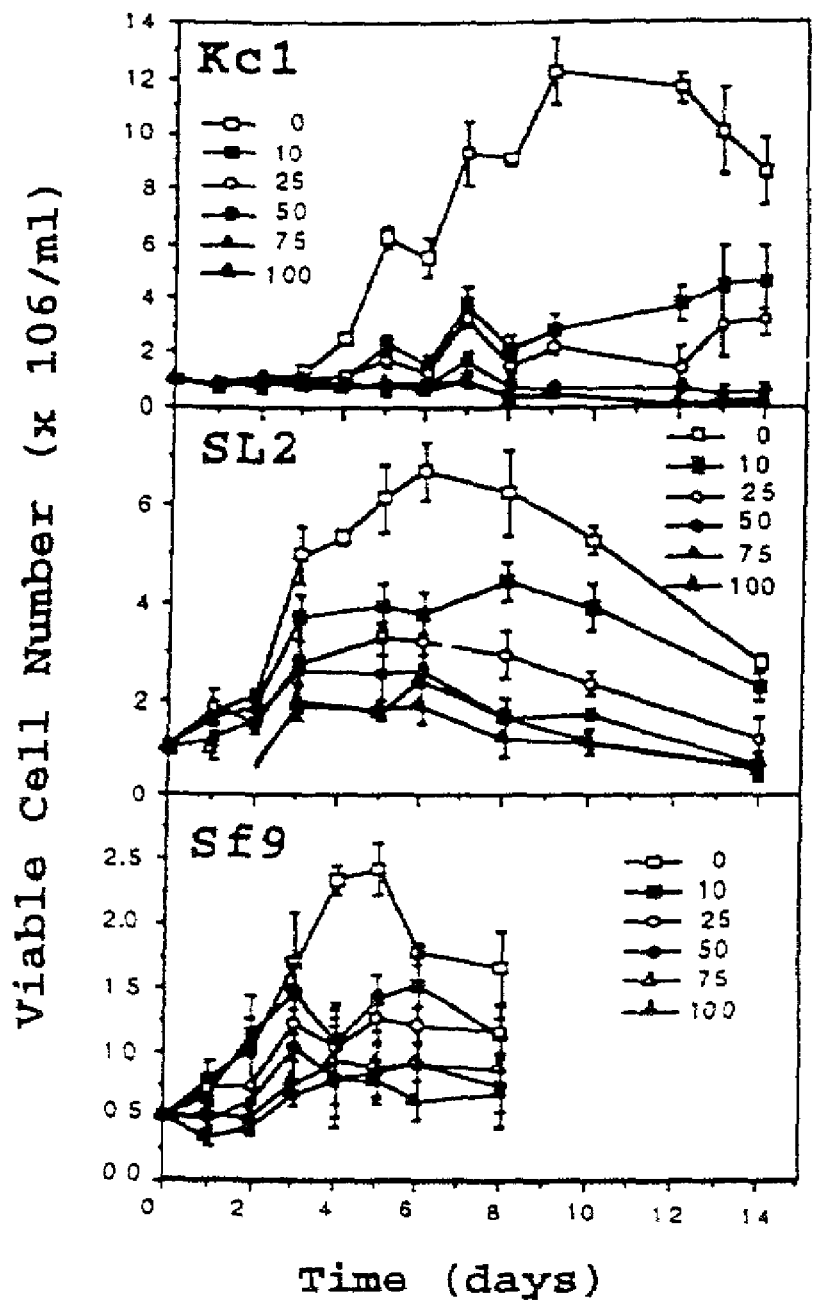
FIG. 4a. Growth of Kc1, SL2 and Sf9 cell lines on varying concentrations of Zeocin. Zeocin concentrations (μg/ml) are shown in the figure for each cell line.
Figure 4B:
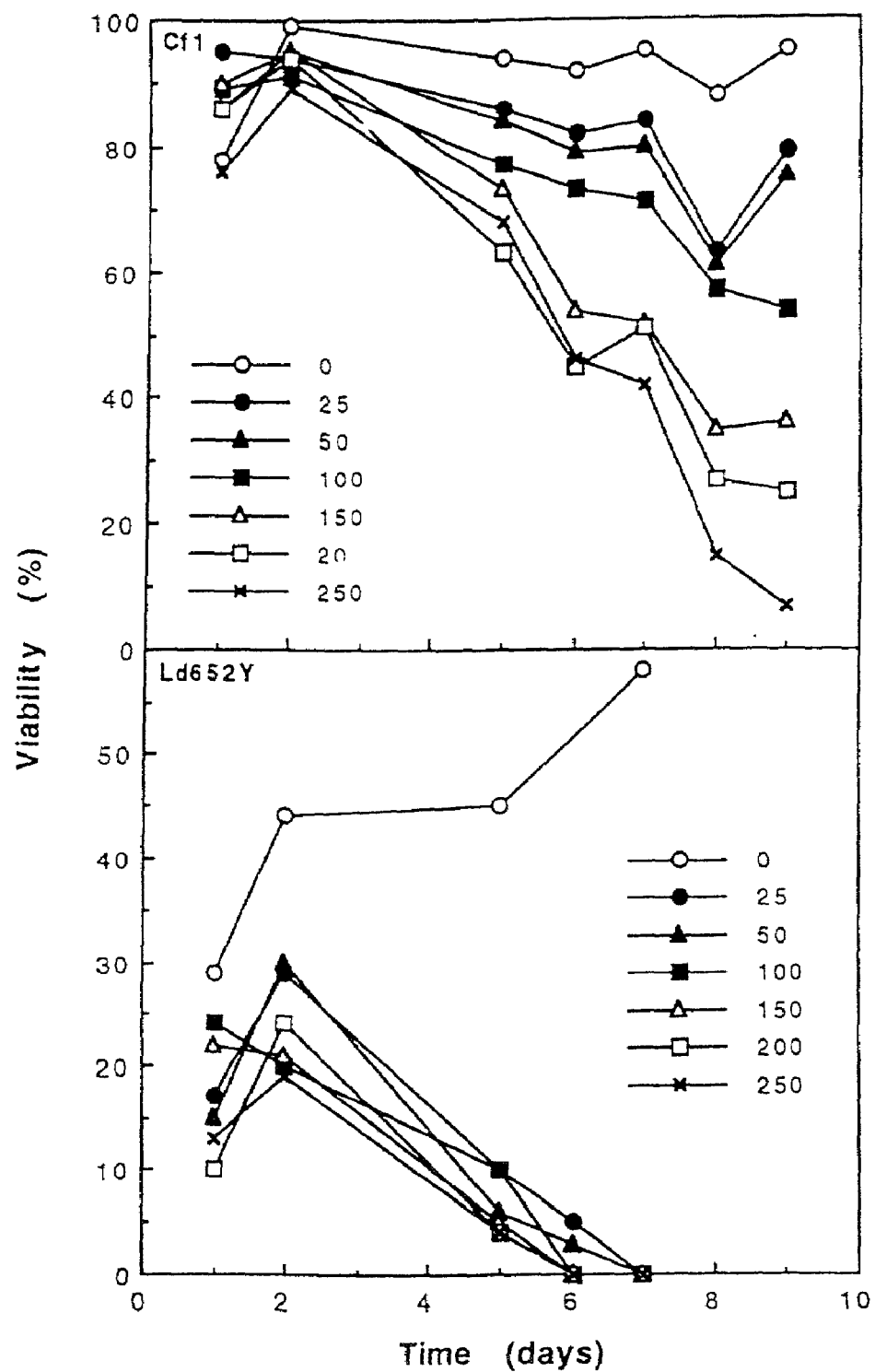
FIG. 4b. Viability of Ld652Y and Cf1 cell lines in the presence of increasing Zeocin concentrations. Zeocin concentrations (μg/ml) are shown in the figure for each cell line.

In accordance with the current understanding of Zeocin's mechanism of action, the minimal inhibitory concentration of Zeocin is described herein as the amount of antibiotic required to limit the culture to one doubling. Growth curves for the determination of inhibitory concentrations of Zeocin in the Kc1, SL2 and Sf9 cell lines (FIG. 4a) were performed in rotating 1.5 ml microcentrifuge tubes containing 1 ml of TC-100 complete medium (pH=6.2) with 10% fetal bovine serum (Life Technologies, Gaithersburg, Md., U.S.A.), $0.5-1.0\times10^6$ cells and varying concentrations of Zeocin (obtained from Invitrogen, San Diego, Calif.) at 27° C. Samples were removed daily, stained with 0.4% trypan blue and the number of viable cells determined in quadruplicate using a hemocytometer. The minimal inhibitory Zeocin concentrations affecting Ld652Y and Cf1 cell lines were determined by seeding approximately 5,000 cells in a total volume of 200 μl TC-100 complete medium +10% fetal bovine serum+ Zeocin into wells of 96 well microtitre plates. Individual wells were sacrificed daily and stained with 0.4% trypan blue to determine cell viability (FIG. 4b).

The D. melanogaster SL2 and Kc1 cell lines and the L. dispar Ld652Y cell line were highly sensitive to Zeocin and exhibited dramatic reductions in growth rates at Zeocin concentrations of 10 μg/ml, although SL2 cell line growth was not as severely inhibited as that of Kc1. Zeocin concentrations greater than 50 μg/ml and 75 mg/ml inhibited more than one round of cell division with Kc1 and SL2 cell lines, respectively. The Sf9 and Cf1 cell lines were less sensitive to Zeocin and required concentrations of at least 250 μg/ml to completely inhibit further cell division. Zeocin concentrations of 800 and 250 μg/ml were found to inhibit growth of Hi5 (T. ni) and C6/36 (mosquito) cell lines respectively.

These results disclose that Zeocin is a candidate antibiotic for use in a selection system for insect cell lines from disparate orders. The viability of such a selection system of course depends upon the identification, discussed below, of promoters that will successfully direct adequate expression in such cell lines from a heterologous gene that confers Zeocin resistance on such cells.

Construction of Vectors to Examine Promoter Expression

The β-galactosidase reporter gene was used to assess the efficiency of selected promoters in a variety of dipteran and lepidopteran insect cell lines. This allowed for the evaluation and comparison of the strengths of several different promoters in insect cell lines prior to using them for expression of genes encoding antibiotic resistance or other heterologous proteins.

Vectors for testing promoter expression (shown in FIG. 3) were constructed by inserting the β-galactosidase reporter gene from the plasmid pDM79 (Mismer and Rubin, Genetics, 116: 565–578 (1987)) downstream of the promoters derived from various baculovirus immediate early genes: the Ac ie1 promoter from the Ac MNPV ie1 gene (characterized in Cartier et al., J. Virol., 68: 7728–7737, (1994)); the Op ie1 promoter from the Op MNPV ie1 gene (characterized in Theilmann and Stewart, Virology, 180: 492–508, (1991)); and, the Op ie2 promoter from the Op MNPV ie2 gene (characterized in Theilmann and Stewart, Virology, 187: 84–96, (1992)). In addition, mammalian viral promoters from SV40 and CMV early genes (obtained from commercial vectors available from Invitrogen, San Diego, Calif.) were tested for expression levels in insect cells. The construction of these vectors for testing promoter expression is discussed below.

The Ac ie1 promoter was tested in the plasmid pAcIE1$^{hr}$β-gal, which was constructed as follows. A 4.2 kb EcoRI fragment from the plasmid pDM79 containing the D. melanogaster alcohol dehydrogenase 5' untranslated region and AUG translational start site, the β-galactosidase gene, and an SV40 transcriptional terminator and polyadenylation signals (pA) was subcloned into the plasmid pBSIIKS (Stratagene Inc., La Jolla, Calif., U.S.A.). After determination of the orientation a PstI-SalI fragment was cloned into the PstI-SalI site of pIE1$^{hr}$/PA (Cartier et al., J. Virol. 68: 7728–7737 (1994)). This places the Ac ie1 promoter and enhancer elements (hr5) upstream of the β-galactosidase transcriptional fusion gene.

Figure 2A:
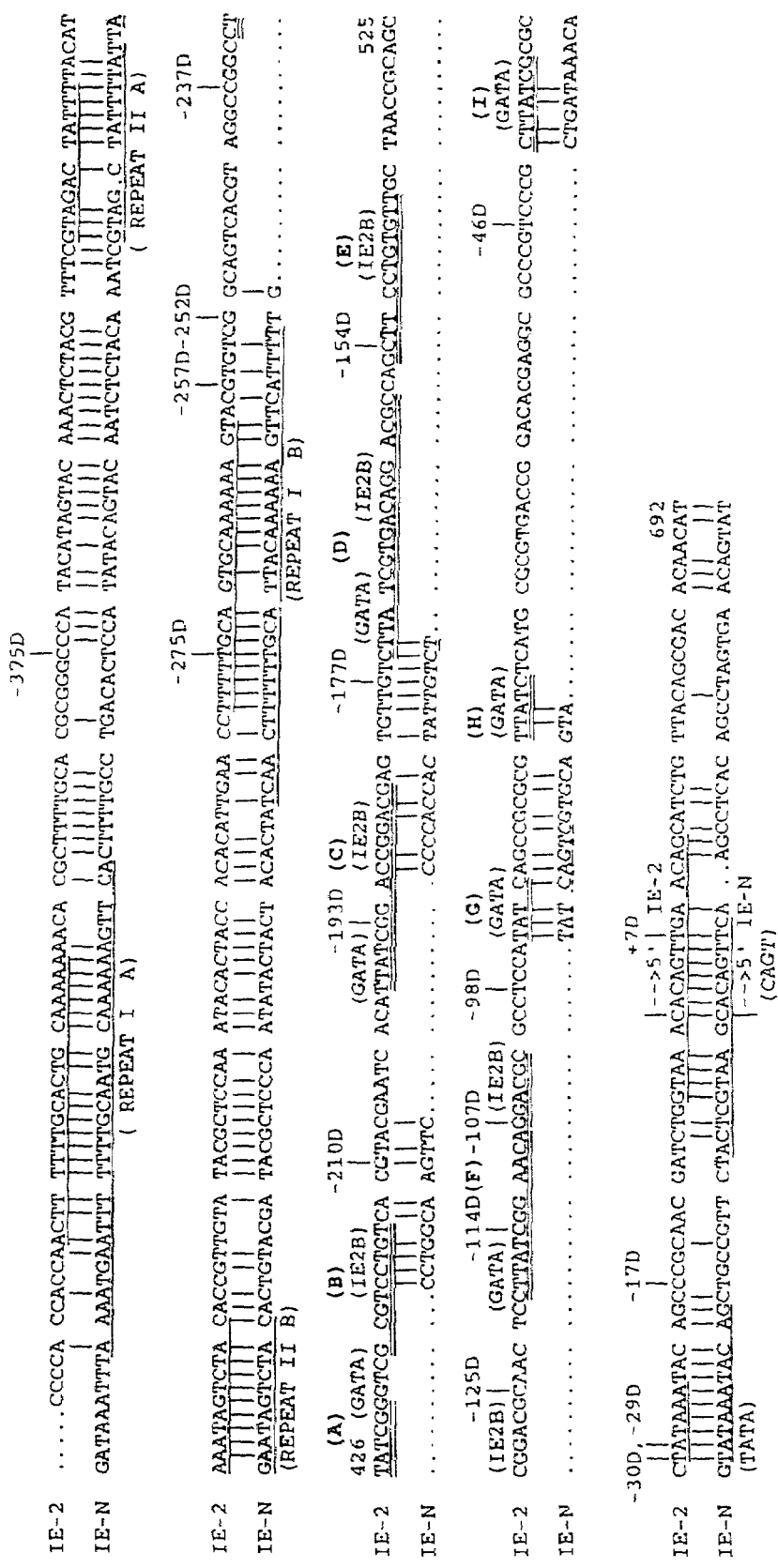
FIG. 2a. Comparison of the promoter sequences of OpMNPV ie2 and the AcMNPV ien genes (Krappa and Knebel-Morsdorf, J. Virol., 65: 805–812 (1991)). The transcriptional start sites are identified by arrows above and below the nucleotide sequence. The alignment was produced by the GAP sequence analysis program (Devereux et al., Nucl. Acids Res., 12: 387–395 (1984)) using a gap penalty of zero. The repeat elements identified in the OpMNPV ie2 promoter are shown double underlined and labeled GATA and IE2B. The inverted repeats in the AcMNPV ien promoter (Carson et al., J. Virol., 65: 945–951 (1991); Krappa and Knebel-Morsdorf, J. Virol., 65: 805–812 (1991)) as well as the related sequences in the OpMNPV ie2 promoter have been underlined and labeled REPEAT I A, REPEAT I B, REPEAT II A and REPEAT II B. The vertical lines identify identical nucleotide sequences. Also shown above the sequences are the location of the 5' ends of the IE-2CAT promoter deletions shown in FIG. 1.

The Op ie2 promoter was tested in the plasmid pOpIE2β-gal, which was constructed to contain Op ie2 promoter sequences from positions −661 to +315 relative to the transcriptional start site (see FIG. 2a). In this vector, the first 94 amino acids of Op ie2 gene are fused to the β-galactosidase gene, and 3' sequences derived from positions −95 to +131 relative to the Op ie2 polyadenylation signal, where the first A of SEQ ID 11: AATAAA is designated as position +1. These sequences were cloned into the PstI-EcoRI site of the vector pBSKS+ (Stratagene, Inc., La Jolla, Calif., U.S.A.).

The Op ie1 promoter was tested in the plasmid pDM79OpIE1, which was constructed by inserting a 598 bp SalI-BamHI fragment from the OpMNPV ie1 gene containing the Op ie1 promoter into the SalI-BamHI site of pDM79 (Mismer and Rubin, Genetics, 116: 565–578 (1987)) upstream of the β-galactosidase gene.

To facilitate direct comparison with the expression assay results obtained from the pDM79OpIE1 vector, the Op ie2 promoter was also placed into the pDM79 vector background. This relevant vector, designated pDM79OpIE2, was constructed by subcloning a 700 bp HindIII-BamHI fragment from the OpMNPV ie2 gene containing the Op ie2 promoter into pBSIIKS (Stratagene, Inc., La Jolla, Calif., U.S.A.). This construct was cleaved with SalI and BamHI and the SalI-BamHI fragment containing the Op ie2 promoter was cloned into the SalI-BamHI site of pDM79.

Testing Promoter Host Range and Efficiency

The relative strengths of various baculovirus promoters was tested in transient transformation expression assays using the constructs described above: pAcIE1$^{hr}$β-gal, pOpIE2β-gal, pDM79OpIE1, pDM79OpIE2. Dipteran (D. melanogaster) cell lines Kc1 and SL2, and lepidopteran cell lines Sf9 (S. frugiperda) and Ld652Y (L. dispar), were transformed with each of these vectors. The Kc1, SL2, Ld652Y and Sf9 cell lines were obtained from ATCC (Rockville, Md., U.S.A.) and maintained in TC-100 complete medium supplemented with 10% fetal bovine serum (Life Technologies, Gaithersburg, Md., U.S.A.) at 27° C. Transformation of cell lines was performed using Cellfectin (Life Technologies, Gaithersburg, Md., U.S.A.) according to the manufacturer's protocols. Plasmid DNA for cell line transformations was purified on CsCl gradients. Two micrograms of plasmid DNA and 5 μl of Cellfectin were prepared as individual 0.5 ml aliquots in unsupplemented Grace's insect medium (Life Technologies, Gaithersburg, Md.), mixed and then incubated for 30 min at 20° C. Approximately $1.0 \times 10^6$ cells were harvested, pelleted at 500 rpm in a benchtop centrifuge and gently resuspended in 1.0 ml of Cellfectin/DNA solution in 5.0 ml plastic tubes. The tubes were incubated horizontally at 27° C. for four hours at which time the cells were pelleted and resuspended in 3.0 ml of TC-100 supplemented with 10% FBS and IX antibiotic-antimycotic mixture (Life Technologies, Gaithersburg, Md.).

After transformation, the cells were transferred to six-well tissue culture plates and incubated at 27° C. Approximately 48 hours after introduction of the plasmid DNA, β-galactosidase activity was determined by pelleting 0.5 ml of cells at 500 rpm, resuspending in 60 ml of 0.25 M Tris-HCl (pH 7.4) and freeze-thawing three times. The cell debris was pelleted at 14,000× g in a microcentrifuge and 5–50 μl assayed for activity according to standard methods (Miller, Experiments in Molecular Genetics, Cold Spring Harbor Laboratory, Cold Spring Harbor, N.Y., USA (1972)). The results of the β-galactosidase assays are described below and the relative enzyme rates summarized in Table 1.

TABLE 1

Relative β-Galactosidase Expression in Insect Cell Lines Using Various Baculovirus Promoter-Reporter Constructs.

| | | Cell Line | | | |
|---|---|---|---|---|---|
| Construct[1] | Promoter | Kc1 | SL2 | Sf9 | Ld652Y |
| pDM79OpIE1 | Op ie1 | 1× | 1× | 1× | 0.5× |
| pDM79OpIE2 | Op ie2 | 10× | 10× | 10× | 0.5× |
| pAcIE1$^{hr}$β-gal | Ac ie1$^{hr}$ | 100× | 100× | 10× | 2× |
| pZOp2Aβ-gal | Op ie2 | 100× | 100× | 10× | 2× |
| pOpIE2β-gal[2] | Op ie2 | 100× | 100× | 1000× | 25–50× |

[1] dotted lines separate constructs in isogenic background vectors
[2] in-frame fusion of Op ie2 coding region to a β-galactosidase gene Kc1, SL2 and Sf9 cell lines transformed with the pDM79OpIE1 expression vector produced 8–30 units of β-galactosidase activity. Cell lines transformed with the pDM79OpIE2 expression vector produced 70–200 units of β-galactosidase activity. The unanticipated result of this assay is that the pDM79OpIE2 vector (with the Op ie2 promoter) produced 5–10 fold more activity than the pDM79OpIE1 vector (with the Op ei1 promoter).

The Op ie2 promoter was even more active in a different vector background. Cell lines transformed with pOpIE2β-gal produced 10–100 times more β-galactosidase activity than the cell lines transformed with pDM79OpIE2. Levels of β-galactosidase activity approaching 800, 2,000 and 20,000 units were found in transformed Ld652Y, *D. melanogaster* and Sf9 cell lines, respectively. The OpIE2β-gal construct consists of an in-frame fusion between the amino-terminal Op ie2 coding region with the β-galactosidase gene. The increased β-galactosidase expression with pOpIE2β-gal demonstrates that sequences immediately proximal to the translational start site in the Op ie2 gene are important in mediating maximum levels of gene expression in Lepidopteran cells (Table 1). This proximal sequence includes a CAGT motif, previously identified in other baculovirus early genes (Blissad and Rohrmann, Virology 170: 537–555 (1989)) and identified in FIG. 2a, however sequences flanking the translational start site may also be involved.

In the *D. melanogaster* cell lines, the enhancer-less Op ie2 promoter (in the vector pZOp2Aβ-gal) unexpectedly mediated expression of β-galactosidase levels comparable to the Ac ie1 promoter with the hr5 enhancer (in the vector pIE$^{hr}$β-gal). A similar result was obtained with transformed Sf9 cell lines, in which the enhancer-less Op ie2 promoter (in pZOp2Aβ-gal) also exhibited β-galactosidase levels comparable to the Ac ie1 promoter with the hr5 enhancer. The activity of the Op ie2 promoter (in pOpIE2β-gal) was as much as 10 fold higher in the Sf9 cell line than in the *D. melanogaster* cell lines.

When the plasmid pZeoSVlacZ (Invitrogen, San Diego, Calif., USA) was used as the transformation vector, the SV40 promoter/enhancer was found to have no detectable activity in any of the insect cell lines tested. This is consistent with previously reported *D. melanogaster* cell-line transformation studies (Bourouis and Jarry, EMBO J., 2: 1099–1104 (1983)). In addition, transformation of cell lines using the original pZeoSV vector, (see below) which uses the CMV promoter to drive expression of the Zeocin resistance gene, failed to generate any Zeocin-resistant *D. melanogaster* or Sf9 cell lines. Presumably, the mammalian CMV promoter was unable to direct proper transcription in the insect system.

The behavior of the Op ie2 promoter in mammalian cell lines was determined by transforming several mammalian cell lines obtained from ATCC (Rockville, Md., U.S.A.) with the plasmid pOpIE2β-gal using Cellfectin (Life Technologies, Gaithersburg, Md., U.S.A.) according to the manufacturers recommendations. These cell lines were maintained in MEM or DMEM medium (Life Technologies, Gaithersburg, Md., U.S.A.) supplemented with 10% FBS at 37° C. under 5% $CO_2$.

No β-galactosidase activity was observed 48 hours after transformation of human (CaCO-2 and HEP-G2), canine (MDCK) or mouse (J774A10) lines with the pOpIE2β-gal construct. Therefore, within the limits of the transfection protocols and β-galactosidase assay, the Op ie2 promoter does not appear to function in these mammalian cell lines.

Construction of Zeocin Resistance Insect Shuttle Vectors

Figure 3:
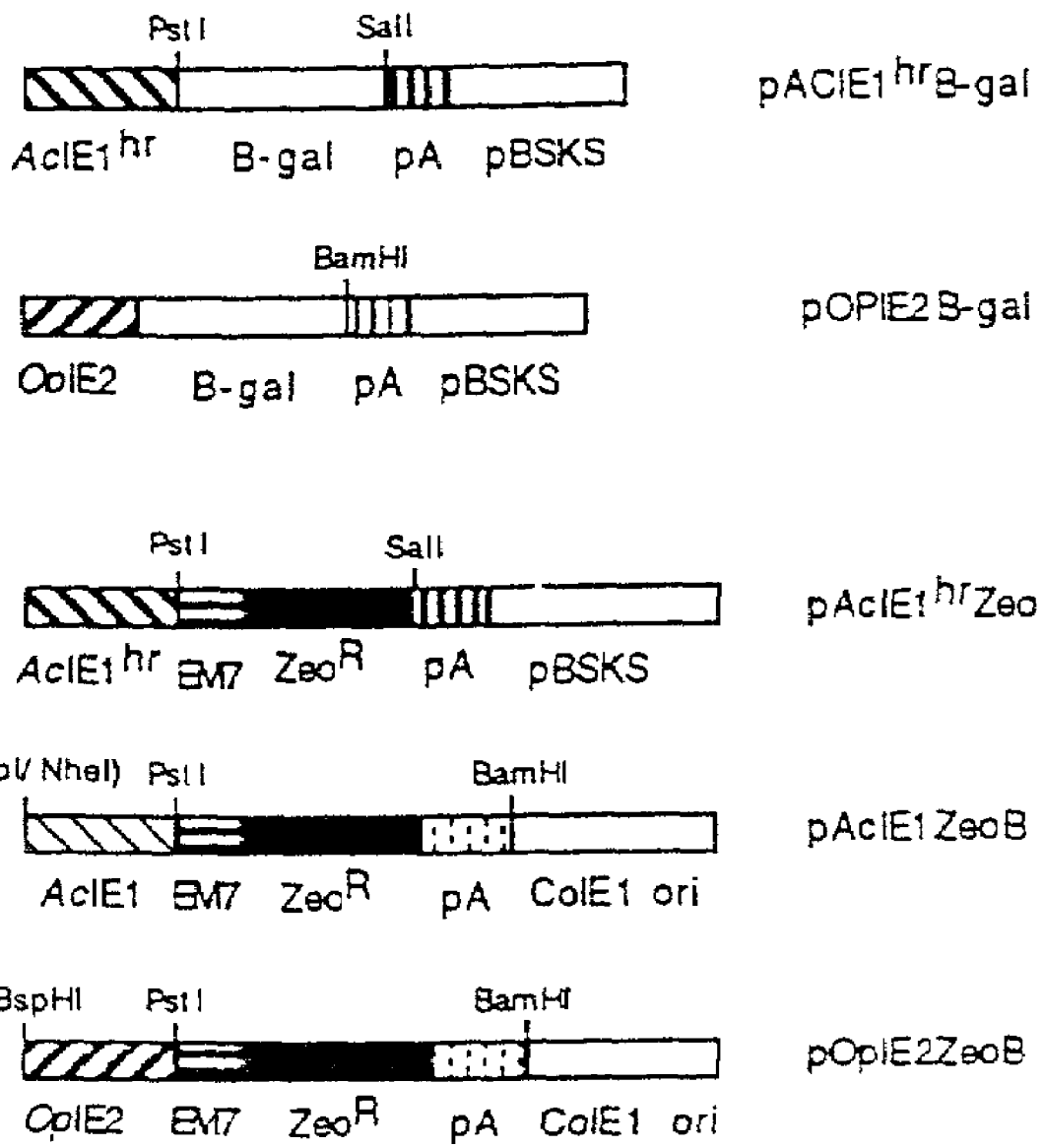
FIG. 3. Vectors constructed for expression of β-galactosidase and the Zeocin resistance gene (ble) using promoter regions from the Ac ie1$^{hr}$, Op ie1 and Op ie2 genes. Different fill-in patterns designate different DNA sequences. Constructs are not drawn to scale.

FIG. 3 illustrates various embodiments of shuttle vectors designed for expression of the ble Zeocin resistance gene in both insects and bacteria. These shuttle vectors were constructed by placing a baculovirus immediate early promoter directly upstream of the synthetic bacterial EM-7 promoter. The baculovirus immediate early promoter and the prokaryotic promoter are operably linked to the downstream ble gene (from the vector pZeoSV, obtained from Invitrogen, San Diego, Calif.). In these novel shuttle vectors, the baculovirus immediate early promoter directs expression of the ble gene in transformed insect cells, and the prokaryotic promoter directs transcription in an appropriate prokaryotic host, such as *E. coli*. Other prokaryotic promoters might be substituted for the EM-7 promoter in these constructs. The construction of the shuttle vectors illustrated in FIG. 3 is described below.

"Operably linked" when describing the relationship between two DNA regions means that they are functionally related to each other. For example, a promoter sequence is operably linked to another sequence if the promoter controls transcription of the other sequence.

The plasmid pAcIE1$^{hr}$Zeo was constructed by cloning a 500 bp PstI-SalI fragment from pZeoSV containing the synthetic bacterial EM-7 promoter and Zeocin resistance gene into the PstI-SalI site of pAcIE1$^{hr}$/PA (Cartier et al., J. Virol. 68: 7728–7737).

The plasmid pAcIE1ZeoB was constructed as follows. The plasmid pZeoSV was digested with BamHI to remove the SV40 enhancer-promoter and polyadenylation signal expression cassette and then religated to form pZeoB. A 470 bp PstI-NheI (blunt-ended with mung bean nuclease) fragment from pAcIE1$^{hr}$/PA containing the AcIE-1 promoter without the enhancer element was placed into the PstI-SspI site of pZeoB upstream of the EM-7 promoter and Zeocin resistance gene.

The plasmid pOpIE2ZeoB was constructed by inserting a 500 bp PstI-BspHI fragment containing the OpIE-2 promoter into the PstI-BspHI sites of pZeoB upstream of the EM-7 promoter and Zeocin resistance gene.

Transformation of Insect Cell Lines to Zeocin Resistance

Transformation of cell lines with Cellfectin was performed as described above. After transformation the cells were transferred to six well tissue culture plates and incubated for an additional 24 hours at 27° C. At this time, the cells were split 1:10 and Zeocin-resistant cell lines were selected with the addition of 150 μg/ml (Kc1 and SL2) or 500 μg/ml (Sf9) of Zeocin to the medium. These concentrations represent a 2–3 fold increase over the minimal inhibitory concentration for these cell lines. With respect to dipteran cells, these concentrations are similar to those used for hygromycin B selection (200 μg/ml; Blochinger and Digglemann, *Mol. Cell. Biol.*, 4: 2929–2931 (1984)) and several times less than is commonly used for selection of G418-resistance (500 to 1000 μg/ml; Rio and Rubin, *Mol. Cell. Biol.*, 5: 1833–1838 (1985)).

Microscopic observations of the non-transformed cell morphology revealed that affected cells became grossly enlarged, eventually lost integrity and lysed. In the case of Sf9 and Ld652Y cell lines, which normally remain attached to the surface of the tissue culture plate, lysis was preceded by the loss of attachment. This phenotype among Zeocin-sensitive cells was highly advantageous and aided the subsequent isolation of single resistant transformed colonies since non-transformed cells were cleared from the surface of the plate, leaving transformed cells free to form colonies.

The frequency at which spontaneous Zeocin-resistant insect cells occur in culture is unexpectedly low. Mock transformations carried out in the absence of plasmid DNA or with plasmids not possessing the resistance gene did not result in any Zeocin resistant insect cells. This unexpected and advantageous characteristic of the Zeocin selection system of the invention is in contrast to the relatively high spontaneous resistance rates that have been reported in selection systems employing antibiotics such as G-418.

Figure 5:
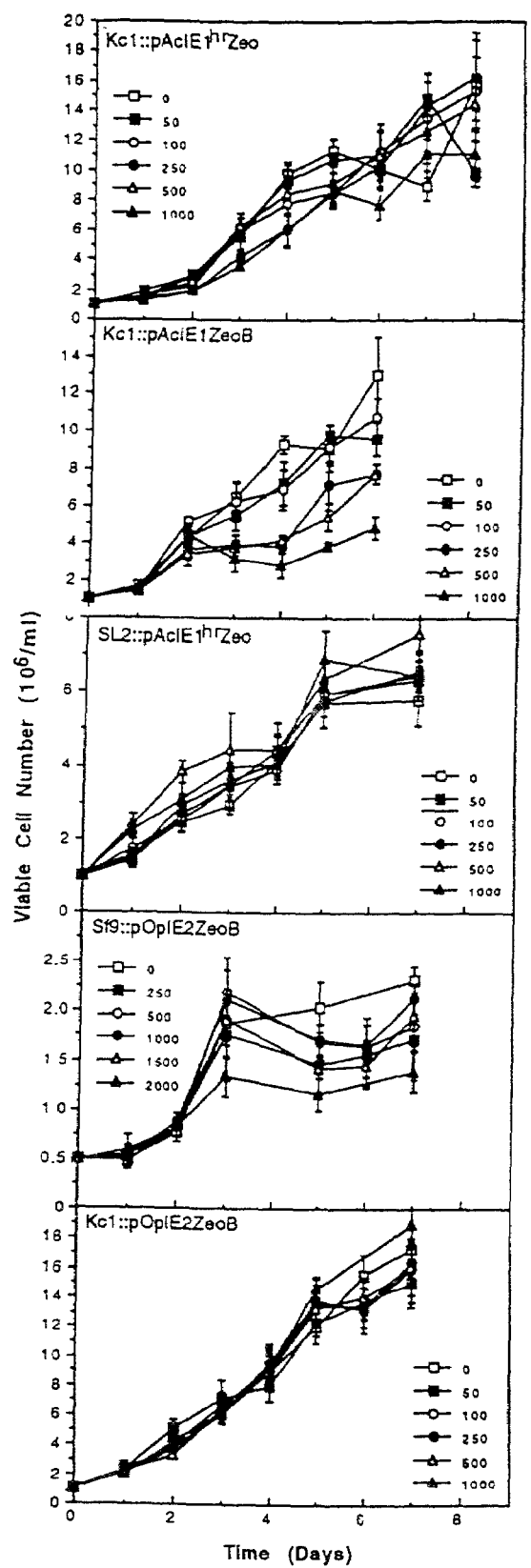
FIG. 5. Growth of Kc1, SL2 and Sf9 cell lines transformed with pAcIE1$^{hr}$Zeo, pAcIE1ZeoB or pOpIE2ZeoB on varying Zeocin concentrations. Plasmid constructs carried by each cell line and the Zeocin concentrations (μg/ml) used are indicated in the figure.

Within 3–4 weeks of transformation, resistant populations of cells were generated. Resistant cells were then removed from selection for several generations before being placed back under selective conditions at various Zeocin concentrations. Individual Zeocin resistant clones were not isolated; Zeocin-resistant cells were maintained as polyclonal cultures. Growth curves for transformed cell lines are shown in FIG. 5. Kc1 and SL2 cell lines possessing the pAcIE1$^{hr}$Zeo construct were resistant to Zeocin at concentrations exceeding 1.0 mg/ml. The rates of cell growth were essentially indistinguishable with increasing concentrations of the antibiotic. This represents a 10–100 fold increase in resistance over the minimum inhibitory concentration for these cell lines. The Kc1 cell line transformed with the Ac ie1 promoter construct lacking the hr enhancer sequences exhibited lower levels of resistance than the corresponding cell lines possessing the enhancer elements. It will be understood from this that variations of the invention could be constructed in which the hr elements are combined with the Op ie2 promoter. In Kc1 cell lines transformed with the Ac ie1 promoter lacking the enhancer elements, cell multiplication was not observed if the Zeocin concentrations exceeded 500 μg/ml.

To determine the effectiveness of the Op ie2 promoter in directing transcription of the Zeocin resistance gene, Kc1 and Sf9 cells were transformed with the plasmid pOpIE2ZeoB. The resultant Kc1 cell line was resistant to Zeocin concentrations exceeding 1.0 mg/ml. Growth rates at the increased antibiotic concentration were similar to the Kc1 cell line transformed with the pAcIE1$^{hr}$Zeo construct. The Sf9 transformed cell line could be propagated at Zeocin levels up to 1.5 mg/ml without appreciable inhibition of cell growth. This demonstrates the surprising result that the enhancer-less Op ie2 promoter functions as well as the Ac ie1 promoter with accompanying hr enhancer elements.

Genomic Stability of Insect Cell Lines Transformed to Zeocin Resistance

As noted previously, many known selection systems exhibit the undesirable characteristic that transforming DNA sequences are amplified over time in the presence of antibiotic selection. These amplified DNA sequences may be unstable and are liable to be rapidly lost in the absence of continued selection. This section discloses experiments that evidence the stability of transforming sequences in insect cell lines transformed to Zeocin resistance in accordance with the present invention.

To assess the stability of transforming DNA sequences in cell lines of the present invention, Zeocin-resistant transformed cell lines were selected, then grown for several generations (2–3 weeks) in the absence of Zeocin, then again placed under selection at various concentrations of Zeocin and grown until early stationary phase (approximately 6–8 days). Southern blotting was then used to assess the stability of the transformed DNA sequences.

Total genomic DNA was then isolated from the cell lines as follows: A 1.5 ml aliquot containing approximately 5–10× $10^6$ cells was pelleted at low speed in a microcentrifuge for 3 minutes; the cell pellet was resuspended in 0.5 ml HB buffer [7 M urea, 2% SDS, 50 mM Tris-HCl (pH=7.5), 10 mM EDTA and 0.35 M NaCl]; the resulting solution was extracted three times with 0.5 ml of phenol-chloroform (1:1) and the DNA precipitated with the addition of 1/10 volume of 3 M sodium acetate and 0.6 volumes of isopropanol; the DNA was dried under vacuum, resuspended in 100 μl of TE buffer [10 mM Tris-HCl (pH=8.0), 1 mM EDTA] and treated with 1 μl of 10 mg/ml RNAse A (Sigma, St. Louis, Mo.) for 30 min at 37° C. The DNA was reprecipitated, washed with 70% ethanol, dried under vacuum and resuspended in 50 μl of TE buffer.

Five micrograms of the total genomic DNA was digested with PstI and SalI, separated by agarose gel electrophoresis and blotted onto nylon membranes (Sambrook et al., 1989). Southern blot analysis was conducted with the ECL chemiluminescent system (Amersham, England) using the entire plasmid constructs of the invention as probes.

Figure 6:
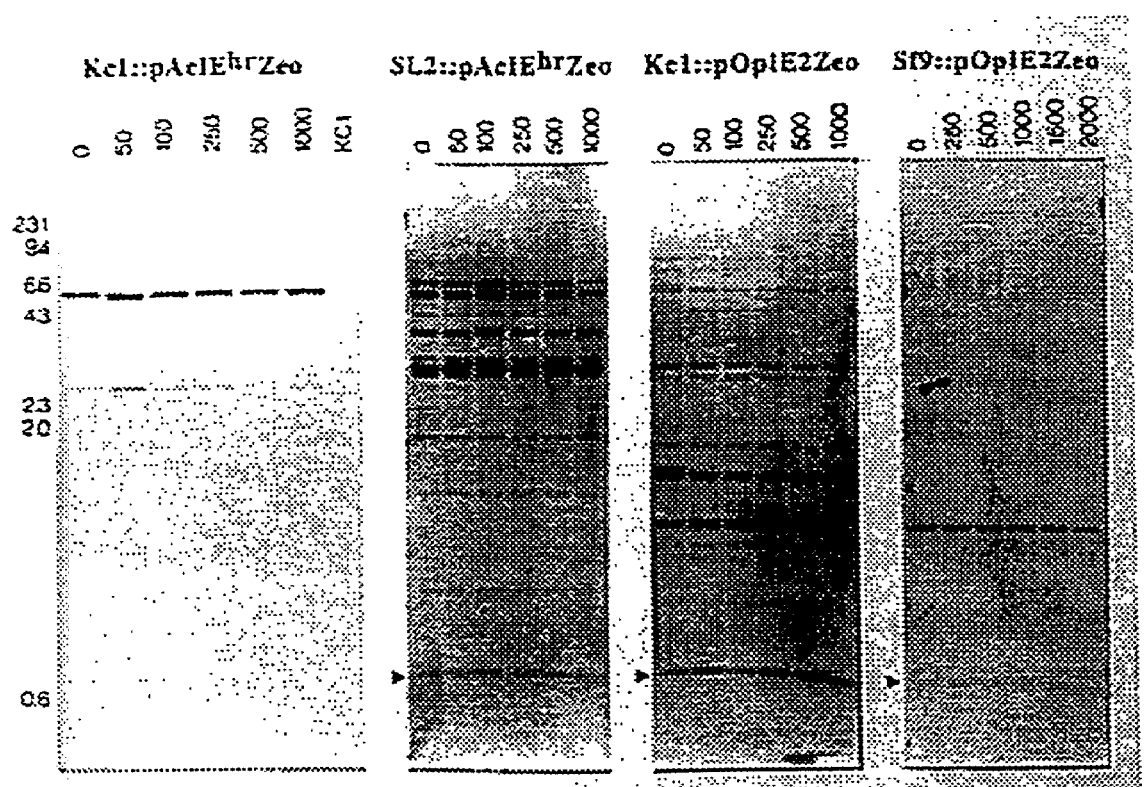
FIG. 6. Genomic Southern blot analysis of cell lines transformed with Zeocin resistance vectors and grown at increasing Zeocin concentrations. The cell line and transforming vector (the vector was also used as the probe) are shown above each autoradiograph. Numbers above the lanes indicate the concentration of Zeocin (μg/ml) in the medium with Kc1 indicating a non-transformed control lane. Molecular weight markers in kilobases are indicated in the margin. The arrow heads indicate the size of the Zeocin resistance gene.

Southern blots of non-transformed SL2 and Sf9 cell line DNA probed with the Zeocin construct did not show any hybridization signal. Southern blot analyses of total genomic DNA from transformed cell lines indicates that the transformation construct had stably integrated into the genomic DNA (FIG. 6). Due to the polyclonal nature of the cell lines, several bands are observed in each lane. However, the band number and intensity remains constant with increasing Zeocin concentrations, indicating that the polyclonal population is stable and that gene amplification is not selected for in order to increase Zeocin resistance. One may therefore conclude that the Op ie2 and Ac ie1$^{hr}$ promoters used to direct expression of the Zeocin resistance gene in the constructs of the present invention provide ample gene product for resistance at elevated concentrations of Zeocin.

These results show an unexpected advantage of the present invention, ie. stability of transforming DNA sequences. The stability of transforming DNA sequences in cell lines of the invention contrasts with the prior art reports discussed above which disclose the frequency with which amplification, and attendant genomic instability, may occur when using prior art selection systems.

Construction of a Zeocin Resistance Shuttle Vector

Figure 7:
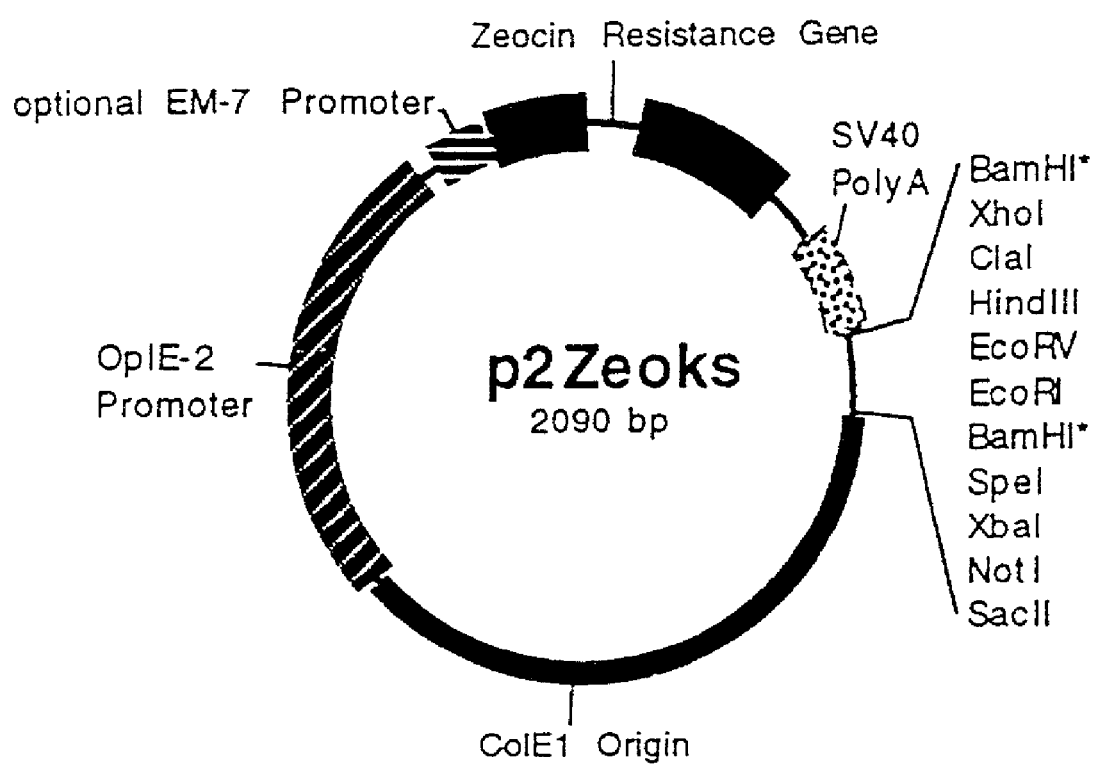
FIG. 7. The cloning/shuttle vector p2Zeoks. The 10 cloning sites are shown with the asterisk (*) indicating BamHI which cleaves twice within this region.

The Zeocin resistance shuttle vector p2Zeoks (FIG. 7) was constructed as follows: An 83 bp ApaI-NotI fragment containing a portion of the multiple cloning site from pBSIIKS was inserted into the ApaI-NotI sites of pZeoB, creating the plasmid pZeoBKS; the pZeoBKS plasmid was then digested with NotI and PstI and the resulting 750 bp fragment was ligated to the 1340 bp NotI-PstI fragment of pOpIE2ZeoB, resulting in the shuttle vector p2Zeoks (FIG. 7).

The p2Zeoks vector utilizes the Op ie2 gene promoter to drive expression of the ble Zeocin resistance gene in insect cells and the small synthetic EM-7 prokaryotic promoter, from the original pZeoSV vector, to direct expression in a prokaryotic host such as E. coli. Selection of transformed E. coli clones may be performed using modified LB (10 g/l tryptone, 5 g/l yeast extract, 5 g/l sodium chloride, pH 7.5) at 20–25 µg/ml Zeocin. Selection in insect cell lines may be accomplished in the presence of 150 µg/ml Zeocin for D. melanogaster cell lines and 250 µg/ml Zeocin for Sf9 cells.

The p2Zeoks vector is relatively small (2090 bp), which maximizes the size of heterologous sequences that may be cloned into the vector. Such heterologous sequences may be inserted at the multiple cloning site, which has ten unique restriction enzyme sites (BamHI, XhoI, ClaI, HindIII, EcoRV, EcoRI, SpeI, XbaI, NotI, and SacII) available for cloning.

Construction of Constitutive Insect Protein Expression Shuttle Vectors

The p2Z series of constitutive insect expression shuttle vectors (FIG. 8a) are derived from the cloning and shuttle vector p2ZeoKS (FIG. 7). The p2Z series illustrates that vectors of the invention may use a compound promoter comprised of a baculovirus immediate early promoter and a prokaryotic promoter, both operably linked to a selectable marker gene. In the p2Z series of FIG. 8, an Op ie2 or Op ie1 promoter is combined with the synthetic bacterial EM-7 promoter to drive expression of the ble gene and confers resistance to Zeocin in both insect cells and E. coli. This chimeric promoter is capable of mediating Zeocin resistance in a wide range of hosts, including E. coli, the D. melanogaster cell lines Kc1 and SL2, the lepidopteran cell lines Sf9 and Ld652Y as well as mosquito cell lines. The construction of the p2Z series of vectors is described below.

To construct p2ZOp2A an additional Op ie2 promoter was inserted into p2ZeoKS. as follows: the plasmid p2ZeoB was cleaved with BamHI, the 5' overhang filled-in using Klenow DNA polymerase with dNTPs, and then cleaved with NotI; a HindIII/BamHI fragment from pOpIE-NBamHI (Theilmann and Stewart, Virology, 187: 84–96 (1992)) containing the Op ie2 promoter was subcloned into the HindIII/BamHI site of pBKSII; this construct was cleaved with HindIII, blunt-ended using Klenow DNA polymerase with dNTPs, and then cleaved with NotI; this fragment which contained the Op ie2 promoter was ligated to the pZeoB vector from above to yield p2ZOp2A. This new construct retains a multiple cloning site, containing 6 unique restriction enzyme sites, downstream of the Op ie2 promoter. This vector may be suitable for the expression of full length cDNAs or promoter-less genes possessing a polyadenylation signal (pA) in a wide variety of insect cell lines.

To facilitate the expression of genes lacking pA signals or to examine the effect of mRNA stabilizing signals on heterologous gene expression, we created variants of the p2ZOp2A vector having either the SV40 early gene pA signal (p2ZOp2C) or the Op ie2 gene pA signal (p2ZOp2F).

The plasmid p2ZOp2C was constructed by inserting an EcoRI/SacII fragment containing the SV40 early gene pA signal sequence from pZeoSV into the EcoRI/SacII site of p2ZOp2A.

The plasmid p2ZOp2F was constructed as follows: the pA signal sequence from the Op ie2 gene was amplified by PCR using the oligonucleotides (designated 5' to 3') SEQ ID NO 2: CCGCGGATCGATATCTGACTAAATCT-TAGTTTGTATTGTCATGT and SEQ ID NO 3: CGGGT-GCGCACGCGCTTGAAAGGA; the PCR product was cloned into the SacII site of p2ZOp2A which had been made blunt using T4 DNA polymerase; the multiple cloning site was expanded using two sets of complimentary oligonucleotides, the first set (SEQ ID 4: AATTTAAACGTTGGTAC-CCTCGAGCTCAGCTGAATTCTGGATCCT and SEQ ID 5: CTAGAAGGATCCAGAATTCAGCT-GAGCTCGAGGTACCAAGCTTTA) was annealed and inserted into the EcoRI/XbaI site and the second set (SEQ ID 6: CTAGACCGGTCATATGCGGGCCGCG-GATCGATCGAT and SEQ ID 7: ATCGATCGATCCGCG-GCCGCATATGACCGT) was inserted into the XbaI/EcoRV site.

The presence of homologous sequences in the same vector, such as the two SV40 pA signals in p2ZOp2C, gives rise to the possibility that recombination between homologous SV40 pA sequences may occur; although we have not encountered this with commonly used rec E. coli hosts. Those skilled in this art will understand that the use of insect-derived pA signals may be functionally advantageous in insect cells. Therefore, an expanded multiple cloning site (MCS) with 13 unique restriction enzyme sites was incorporated into the F-derivative vectors that possess the Op ie2 pA signal sequences. In addition, these vectors also contain translation stop codons in all three reading frames to allow expression of truncated genes. The primer SEQ ID 8: 5' TCGGGTGCGCACGCGCTTGAAAGGA 3', is specific to the Op ie2 pA signal sequence and can be used to sequence the in-frame fusion region and is useful for the analysis of ordered 3' deletion series.

To further eliminate homologous sequences within the same vector, the p1Z series were developed that use the Op ie1 promoter to drive the Zeocin resistance gene making the more active Op ie2 promoter solely available to direct foreign gene expression. The vector p1ZOp2A was generated by cloning a SalI/BamHI fragment from pOPIE-1B74BamHI (Theilmann and Stewart, Virology, 187: 84–96 (1992)) containing the Op ie1 promoter was cloned into the SalI/BglII site of a transition vector. Subsequently, a NruI/PstI fragment was inserted into the BspHI (blunt-ended using Klenow DNA polymerase with dNTPs)/PstI site of p2ZOp2A replacing the Op ie2 promoter which was directing the Zeocin resistance gene.

The plasmid p1ZOp2F was created by inserting a 700 bp HaeII fragment containing the MCS of p2ZOp2F into the HaeII sites of p1ZOp2A.

Construction of a Non-Selectable Insect Protein Expression Vector

To enable the selection of stable cell lines producing heterologous proteins under the transcription of the Opie2 promoter, but without the presence of the Zeocin resistance gene, another vector was constructed. This vector designated pAmp2E was constructed as follows (FIG. 8a). A 1553 bp BspHI fragment from p2ZOp2E containing the Opie-2 promoter, multiple cloning site insect poly A tail and ColE1 section was ligated to a 1.0 kb BspHI fragment from pBluescriptIIks containing the ampicillin resistance gene. The B-lactamase gene provides the resistance required for selection in bacteria under ampicillin selection, but no selectable marker for selection in insect cells is provided. This vector pAmp2E has the ability to direct heterologous protein expression and may be used with other selection vectors such as G418, hygromycin, methotrexate or other selection vectors, in co-transformation experiments without having the Zeocin resistance gene present. In situations where Zeocin selection is not possible, due possibly to previous selection of a cell line with the Zeocin resistance gene, this vector will enable production of heterologous protein while selecting with any other selection marker available for the stable transformation of this cell line.

It also allows for the mixture of a heterologous protein producing vector with any selection vector, in ratios such as to maximize protein production in a stable selected cell line. Such ratios of vectors may include heterologous expression vector to selection vector ratios such as 1:1, 2:1, 5:1, 10:1 or any other such combination that selects for a stable cell line that produces the maximum amount of heterologous protein.

Construction of Secretion Protein Expression Shuttle Vectors

The ability to secrete a heterologous protein into the culture medium is of benefit for downstream processing of the protein. Several examples in this application demonstrate that insect cells are capable of secreting large amounts of heterologous proteins. In addition to those secretion signals already demonstrated in the text (melanotransferrin, transferrin, ITP), both the bombyxin and mellitin secretion signals were added to the vectors (FIG. 8a).

The bombyxin secretion signal was prepared by annealing the following two oligonucleotides SEQ ID 14: BBXF 5'-AATTATGAAG ATACTCCTTG CTATTGCATT AATGTTGTC AACAGTAAT GTGGGTGTCA ACAAGCTTA-3' and SEQ ID 15: BBXR 5'-CTAGTAAGCT TGTTGACACC CACATTACTG TTGACAACAT TAATGCAATA GCAAGGAGTA TCTTCAT. This annealed fragment was inserted into the EcoR1/BamHI site of p2ZOp2D. This intermediate was cleaved with HindIII/Pst and annealed to the HindIII/PstI fragment of p2ZOp2F containing the MCS, ori, and ie-2 promoter to create p2ZOp2G.

The honey bee mellitin secretion signal was removed from the vector pRSETB-HBM (Invitrogen, USA) as a 50 bp NdeI (partially filled in with dTNP and Klenow)/EcoRI fragment. This was ligated to p2ZOp2F cleaved with HindIII (partially filled in with dATP, dGTP, dCTP and Klenow) and EcoRI and ligated to the above fragment to create p2ZOp2I.

Construction of Inducible Insect Protein Expression Shuttle Vectors

Expression of foreign proteins, particularly those which maintain function across eukaryotic species boundaries, can disrupt cellular physiology to such an extent that total protein expression is significantly reduced. These nocuous proteins may be produced in cell line systems using inducible promoters to maintain the amount of protein within physiologically tolerable levels. For example, the hsp 70 promoter has been used to mediate expression of gated chloride ion channels (Shotkoski et al., *FEBS Lett.*, 380: 257–262 (1996)) and the Mtn promoter was used to control expression of the human H-ras oncogene (Johansen et al., *Genes Develop.*, 3: 882–889 (1989)).

To construct an inducible insect expression shuttle vector of the invention, the Mtn promoter was incorporated into the p2ZMtnF vector by inserting a 500 bp SalI/EcoRI fragment from pMT-1 (Kovach et al., *Insect Mol. Biol.*, 1: 37–43 (1992)) containing the Mtn promoter that was blunt-ended using Klenow DNA polymerase with dNTPs into the BamHI site of p2ZeoB which was also made blunt. The resulting vector, p2ZMtn, was cleaved with XhaI, blunt-ended using Klenow DNA polymerase with dNTP's and then re-cleaved with PstI yielding a fragment that contained the Zeocin resistance gene and the Mtn promoter. This fragment was ligated to a PstI/HindIII (blunted using Klenow DNA polymerase and dNTPs) fragment of p2ZOp2F containing an expanded MCS and the origin of replication to yield the p2ZMtnF vector. The p2ZMtnF vector contains an expanded MCS for efficient cloning as well as the Op ie2 pA signal and may provide regulated, inducible transgene expression in insect cell lines, including *D. melanogaster* and mosquito cell lines.

The use of the Mtn promoter as the inducible promoter in vectors of the invention may have advantages over the use of the hsp promoters. For example, protein can be produced continuously from the Mtn promoter using low levels of cadmium or copper salts to induce the promoter without dramatic effects on host physiology. In contrast, the hsp70 promoter produces low levels of product constitutively and induction requires periodic heat shock (Berger and Rudolph, Invertebrate Cell System Applications, CRC Press, Inc., Boca Raton, Fla. (1989)) which may impair cell growth.

Construction of a LacO/LacR Inducible System

An inducible expression vector that utilizes the lac repressor system was constructed. Two vectors were constructed both to evaluate the effectiveness of this system in insect cells and to provide tight control of extremely toxic proteins. The plasmid p2ZOp2J-1 was constructed by cloning a 235 bp BglII/NotI fragment from pET28a (Novagen) containing the lacO region, a ribosome binding site, an ATG translational start codon followed by a His and T7 protein tags; into the BamHI/NotI site of p2ZOp2F. For toxic proteins this vector also provides for regulation of the cryptic ie-2 promoter activity in bacteria when the lac repressor is present.

The plasmid p2ZOp2J-3 was constructed as follows. A BglII/NotI fragment from pOP13CAT containing an SV40 intron with three internal lacO regions was cloned into the BamHI/NotI site of p2ZOp2A. From this intermediate, a PstI/NotI (blunted with Klenow and dNTP's) fragment containing the SV40 intron/lacO combination was isolated and ligated to a PstI/PvuII fragment of p2ZOP2F to yield p2ZOp2J-39 (FIG. 8b)

A vector to express the lac repressor was constructed in the following way. A fragment containing the lac repressor was amplified from the lacI containing vector pet21 (Novagen) using the following primers SEQ ID 12:5'-TCAGCTGCAG ATGAAGAGGC CTAGACCTAT GAAACCAGTA ACGTTATACG ATGTC-3'; and, SEQ ID 13: 5'-ACTTAAGCTT ATAGCGATGA CTGCCCGCTT TCCAGTCGGG AAACCTGTCG-3'. The second primer contains the nuclear localization signal sequence required for directing the lac repressor protein to the nucleus. This fragment was cleaved with Pst1/HindIII and inserted into the PstI/HindIII site of pOp1/pA to yield pOp1lacR (FIG. 8b).

Construction of the Tet System

The Tet system is based on two regulatory elements derived from the tetracycline-resistance operon of the *E. coli* Tn10 transposon: the tet repressor protein (TetR) and the Tet operator DNA sequence (tetO) to which TetR binds. This system is typically called Tet-Off as the addition of tetracycline turns off transcription. An alternate TetR contains several amino acid changes which causes transcriptional activation in the presence of tetracycline. This system is designated Tet-On.

The vector p2ZOp2T contains a chimeric promoter consisting of the Opie2 promoter and seven copies of tetO. It was constructed by removing the 300 bp XhoI/SacI (blunted using T4 polymerase and dNTP's) fragment from pTRE (Clontech) and inserting this into the XhoI/NarI (blunted with Klenow and dNTP's) site of pBKSOpIE-2. This places the Tet operator upstream of a minimal promoter element of the Opie-2 promoter. From this cloning intermediate, an 800 bp XhoI (blunted with Klenow and dNTP's)/EcoRI fragment containing the TetO/Op ie-2 promoter was then placed into the BspHI (blunted with dNTP's)/EcoRI site of p1ZOp2F to yield p1ZOp2T (FIG. 8b).

The second key component of the system is a "regulator" plasmid which expresses a hybrid protein known as the tet-controlled transcriptional activator (tTA). tTA binds the Tet operator sequence (tetO) and thereby activates transcription in the absence of tetracycline. Thus, as tetracycline is added to the culture medium, transcription is turned off in a dose-dependent manner. The 1 kb EcoRI/BamHI fragment encoding tTA was removed from pTet-Off (Clontech, USA) and cloned into the EcoRI/BamHI site of p2ZOp2D yielding the plasmid p2ZOp2DtTA which is comparable to the Tet-Off system (FIG. 8b). The 1 kb EcoRI/BamHI fragment from Tet-On (Clontech) was also cloned into the EcoRI/BamHI site of p2ZOp2D yielding the plasmid p2ZOp2DrtTA which is comparable to the Tet-On system (FIG. 8b).

Construction of a Gal4 Control System

The gal4 control system allows for very tight control of a gene using a two stage system. The heterologous gene is placed behind a set of upstream activator sequences (UAS) derived from the gal 4 gene family and a minimal promoter derived from the hsp70 gene. Transcription requires the presence of the gal4 gene product which is controlled by the mtn promoter. Once the mtn promoter is activated, gal4 is made and this in turn binds the UAS sites and activates transcription of the heterologous gene.

The 3 kb NotI fragment from pGaTN containing the gal4 gene was inserted into the NotI site of p2ZmtnF to yield p2ZmtnFgal4 (FIG. 8b). This vector is used to induce expression of the gal4 gene product using methods described above in this patent and was used to construct cell lines that could be induced to express gal4. Other inducible promoter systems can also be used to drive the production of gal4.

The vector p2ZUASmPF (FIG. 8b) was created as follows. A 400 bp SphI (blunted with T4 and dNTP's)/XbaI fragment containing five UAS from pP[UAST] was inserted into the BspHI (blunted with Klenow and dNTP's)/XbaI site of p2ZOp2F. This vector contains the 5 UAS, a minimal promoter, a multiple cloning site and allows for selection under Zeocin. To create a B-gal reporter construct, the 3 kb EcoRI B-gal fragment from p2ZmtnFB-gal was placed into the EcoRI site to create p2ZUASmPFB-gal.

Expression of Reporter Genes to Assess Host Spectrum and Production Capacity

Plasmids containing either β-galactosidase or green fluorescent protein (GFP) reporter cassettes were constructed (FIG. 8) to assess the utility of expression systems of the invention in a variety of insect cell lines. The construction of each of the protein expression vectors is described below.

The plasmid p2ZOp2Aβ-gal was constructed by inserting a 4.2 kb EcoRI fragment from pDM79 containing the *D. melanogaster* alcohol dehydrogenase 5' untranslated region and AUG translational start site, the *E. coli* lacZ gene, and an SV40 transcriptional terminator and polyadenylation signal (pA) into the EcoRI site of p2ZOp2A.

The plasmid p2ZOp2C-GFP was created by inserting an 800 bp EcoRI fragment from pGFP10.1 (Chalfie et al., *Science*, 263: 802–805 (1994)) containing the GFP-encoding region into the EcoRI site of p2ZOp2C.

The plasmid p2ZMtnFβ-gal was generated by inserting the 4.2 kb EcoRI β-galactosidase gene fragment described above into the EcoRI site of p2ZMtnF.

Since the activity of β-galactosidase can be quantitatively determined, the p2ZOp2Aβ-Gal reporter plasmid may be used to predict the amount of foreign protein that can be produced in a specific cell line. Transient expression assays using 2 μg of p2ZOp2Aβ-Gal plasmid and 10 μl of the cationic liposome Cellfectin (Life Technologies, Gaithersburg, Md.) routinely resulted in levels of β-galactosidase activity approaching 800, 3000 and 20,000 units in Ld652Y, *D. melanogaster* and Sf9 cell lines, respectively.

With cell lines exhibiting moderate to high levels of endogenous β-galactosidase activity, such as Ld652Y, the GFP reporter plasmid may be used to estimate production capability. In addition, this unobtrusive marker allows the level of protein expression in individual cells to be determined. This small reporter cassette consisting of the Op ie2 promoter, the GFP coding region and a transcriptional termination and pA sequence can be easily incorporated into a heterologous protein expression vector or co-transformed in concert with the heterologous protein expression vector. Subsequently, individual cells exhibiting a higher degree of fluorescence and thus higher levels of heterologous protein expression may be selected using a fluorescence activated cell sorting (FACS) system without irreversible disruption of cellular physiology.

The ability to incorporate an antibiotic selection cassette, a heterologous protein expression cassette and a reporter cassette within the same vector is highly advantageous and is a consequence of the manner in which the individual cassettes and vectors of the invention are engineered. The small size of these vectors allows for relatively large genes to be cloned, manipulated and expressed without the need for cumbersome subcloning or resorting to cosmid or bacteriophage vectors. It follows that other unobtrusive markers, such as integral membrane proteins that may be detected using labeled antibodies, could also be applied to the selection system of the invention.

Inducible expression mediated by vectors of the invention was tested in *D. melanogaster* cell lines in transient expression assays using p2ZMtnβ-Gal reporter plasmid (FIG. 9). Subsequent to transformation, the Mtn promoter was induced by the addition of 50–1000 μM $CuSO_4$ (final concentration) from a 100 mM stock solution. The cells were transferred to six well tissue culture plates and incubated for an additional 48 hours at 27° C. at which time the cells were harvested, pelleted at 4,000×g in a microcentrifuge and resuspended in 60 μl of 0.25 M Tris-HCl (pH 7.4). The cells were lysed by freeze/thawing three times, the debris pelleted once again and β-galactosidase activity quantitated in the supernatant according to standard methods. Western blot analysis was conducted by electrophoretically separating 10 μg of cellular protein on 10% SDS-PAGE gels and transferring to a nitrocellulose membrane. β-galactosidase was detected using mouse monoclonal anti-β-galactosidase (Promega, Madison, Wis.) as the primary antibody at a 1/10,000 dilution and horseradish peroxidase-conjugated goat anti-mouse antibody (BioRad, Richmond, Calif.) as the secondary at a 1/20,000 dilution followed by detection using the ECL chemiluminescent system (Amersham, Oakville, ON).

In the absence of induction, β-galactosidase activity was only slightly higher (4–7 units) than the endogenous background activity (2.5 units) and could not be detected using western blot analysis. The addition of increasing concentrations of $CuSO_4$ resulted in corresponding increases in β-galactosidase production as recorded 48 hours after transformation. In transient assays using a $CuSO_4$ concentration of 1000 μM, induction of β-galactosidase expression was approximately 5–10 fold less than that observed for cell lines in which constitutive expression was mediated by the Op ie2 promoter. Within the sensitivity limits of the β-galactosidase assay, the Mtn promoter failed to function, either constitutively or with induction, in Sf9 or Ld652Y cell lines.

The lacI/LacO inducible system can also be used in insect cell lines. Western blot analysis of 48 hour insect cell pellets from transformations with p2ZOp2FlacR or pOp1LacR, using the commercially available LacR antibody (Stratagene, USA) demonstrated that the Lac repressor was made in insect cells. To generate stable clones expressing the lac repressor this clone was co-transfected into insect cell lines with the p2ZOp2J vector series. Co-transfection was done using 1 ug of each p2ZOp2J and pOp1LacR with 10 ul of Cellfectin.

Utilizing p2ZOp2J-1 or -3 with B-galactosidase as the reporter in Sf9 cells, it was found that repression of the B-gal reporter occurred with p2ZOp2J-1 construct (50 units), but repression was best with the p2ZOp2J-3 construct (10 units). Addition of 1 mmol IPTG (isopropyl β-D-thiogalactoside) allowed for derepression of the system and B-galactosidase production of 400 units from p2ZOp2J-1B-gal and 500 units from pZOp2J-3Bgal. Subsequent analysis using other insect cell lines including but not limited to Ld652Y, Hi5 and Kc1, demonstrated that the lac repressor system worked equally well in these systems.

The tet system can also be used in insect cells. Although expression from this system is lower than from the parent vector p2ZOp2F due to creation of a minimal promoter, the vector has the added benefit of tight regulation which will play an important role in the expression of enzyme cascades. Using B-gal as the reporter these constructs were tested for their ability to control B-galactosidase expression. The co-transfection of p2ZOp2TB-gal and p2ZOp2DtTA (Tet-Off) in insect cells demonstrated that in the presence of doxycycline (tetracyline derivative) the amount of B-galactosidase produced was not above background levels. Removal of doxycycline resulted in a 10 fold increase in the amount of B-gal produced.

Co-transfection of the vector p2ZOp2TB-gal and p2ZOp2DrtTA (Tet-On) in insect cells demonstrated that in the absense of doxycycline (tetracyline derivative) the amount of B-galactosidase produced was also not above background. Addition of doxycycline resulted in a 4 fold increase in the amount of B-gal produced over background.

Both of these experiments demonstrates that the Tet system functions as an inducible system in insect cells.

To test the gal4 system in insect cell lines the vector p2ZUASmPFB-gal was placed in insect cell lines harboring the p2ZmtnFgal4 construct. Alternatively the constructs could be co-transfected into cell lines. No B-gal activity was detected in both transient and stable insect cell lines. Upon addition of 500 uM copper sulphate to induce the mtn promoter, B-gal expression was found to be greater than 100 units indicating that this induction system is functional in insect cells. The advantage of this induction system over the above systems is the two stage control system which may be critical when dealing with enzyme cascades or signal transduction pathways that require precise on/off control. It also gives a third system for introducing an inducible gene product into insect cells. This is critical when studying cascade systems that requires multiple control points.

Generation of Stably Transformed Insect Cell Lines Expressing Heterologous Reporter Genes The ability of stable, transformed cell lines of the invention to express foreign protein was examined by generating polyclonal Sf9, SL2 and Ld652Y cell lines, as well as several clonal SL2 cell lines, possessing the pZOp2Aβ-Gal construct.

Transformation was accomplished as follows. Approximately, $2 \times 10^6$ cells were transformed with 2 µg of CsCl-purified plasmid and 10 µl of Cellfectin (Life Technologies, Gaithersburg, Md.) according the manufacturer's recommendations. The cells were transferred to 6-well tissue culture plates and allowed to recover and express the resistance marker for 48 hours At this time the cells were split 1:10 and resistant polyclonal cell lines selected with the addition of 150, 250 and 1000 µg of Zeocin' (Invitrogen, San Diego, Calif., USA) with the Ld652Y, D. melanogaster and Sf9 cell lines, respectively.

Clonal SL2 cell lines were generated by limited dilution, whereby $1 \times 10^3$ cells, that had been allowed to recover for 48 hours, were placed into individual wells of a 96 well micro-titre plate with $1 \times 10^4$ non-transformed feeder cells. Isolated clones appeared in a portion of the wells within 2–3 weeks.

Total genomic DNA was isolated as described above. Five micrograms of the total genomic DNA was digested with either PstI and SalI or EcoRI, separated by agarose gel electrophoresis and blotted onto nylon membranes. Southern blot analysis was conducted with the ECL chemiluminescent system (Amersham, England) using the entire pZOp2Aβ-Gal plasmid as a probe. Southern blotting confirmed that the clonal lines were indeed uniform and transformed with the vector. As expected, Southern blots on DNA isolated from non-transformed SL2, Sf9 and Ld652Y control cell lines did not show any hybridization signal.

When maintained under constant selection the "polyclonal" Ld652Y, Sf9 and SL2 cell lines expressed 2, 6 and 5500 units of β-galactosidase, respectively, after 20 passages (approximately 5 months). The stable SL2 clonal lines expressed between 1000–4000 units of β-galactosidase. In the absence of antibiotic selection β-galactosidase production by the polyclonal SL2 cell line declined, eventually stabilizing at approximately 1000 units. Southern blot analysis revealed that this decline in enzyme production did not result from a corresponding loss of vector sequences. This raises the possibility that genomic silencing of a fraction of the expression cassettes may have occurred in the absence of selective pressure, as is often observed with transgenes (Meyer, TIBTECH, 13: 332–337 (1995)).

Southern blot analysis of the β-galactosidase expressing polyclonal and clonal cell lines (FIG. 10) shows that a correlation exists between vector copy number and enzyme expression. The relative capacity of cell lines derived from different species to express heterologous proteins may be enhanced by developing criteria for transformation and selection that maximize vector DNA uptake and integration.

Characterization of Promoter Elements in the Op ie2 Promoter.

Characterization of the Op ie2 promoter indicates that it contains a number of distinct functional sequence elements. Previously published data, together with the data disclosed herein, together indicate that new promoters having homology to functionally important sequence elements of the Op ie2 promoter may be constructed in accordance with the present invention.

The 5' cis -acting promoter sequences of Op ie2 were initially analyzed by gross deletion analysis using chloramnphenicol acetyl transferase (CAT) reporter constructs in Ld652Y and Sf9 lepidopteran insect cell lines (Theilmann and Stewart, Virology, 187: 84–96 (1992)). CAT expression levels were much higher in Sf9 cells, which allowed for a more sensitive analysis of the Op ie2 promoter.

Preliminary deletion analysis identified two repeated elements that appeared to be involved in directing expression from the Op ie2 promoter (Theilmann and Stewart, *Virology*, 187: 84–96 (1992)). The consensus sequence of the repeated elements are SEQ ID 9: CTTATCGG and SEQ ID 10: ACAGGACGC, termed the GATA and IE2B elements. The GATA and IE2B elements are repeated seven and six times, respectively, in the ie2 promoter. The GATA element is identical to that found to bind cellular factors in the OpMNPV efp/gp64 and AcMNPVpe38 promoters (Krappa et al., *J. Virol.* 66: 3404–3503 (1992)). The IE2B element has not been found in any other baculovirus promoters. The GATA and IE2B elements are found three times as paired elements in the Op ie2 promoter (FIGS. 1a and 2).

For deletion analysis, an Op ie2 promoter reporter plasmid, pIE-2CAT, was constructed by placing the CAT gene 20 bp downstream from the Op ie2 transcription start site using BamHI linkers. The 5' promoter region was derived from the Op ie2 sequences 1–677 and the 3' polyadenylation (pA) sequences were derived from the Op ie2 sequences 1865 to 2010 (Theilmann and Stewart, *Virology*, 187: 84–96 (1992)). The CAT gene was obtained as the BamHI fragment of the pCAT plasmid (Mackett et al., *J. Virol.*, 49: 857–864 (1984)). Deletion subclones (5' to 3') of the promoter region were generated using ExoIII and either mung bean or Bal31 exonuclease (Sambrook et al., *Molecular Cloning: A Laboratory Manual*, Cold Spring Harbor, N.Y. (1989); Yanisch-Perron et al., *Gene*, 33:103–119 (1985)).

Figure 1A:
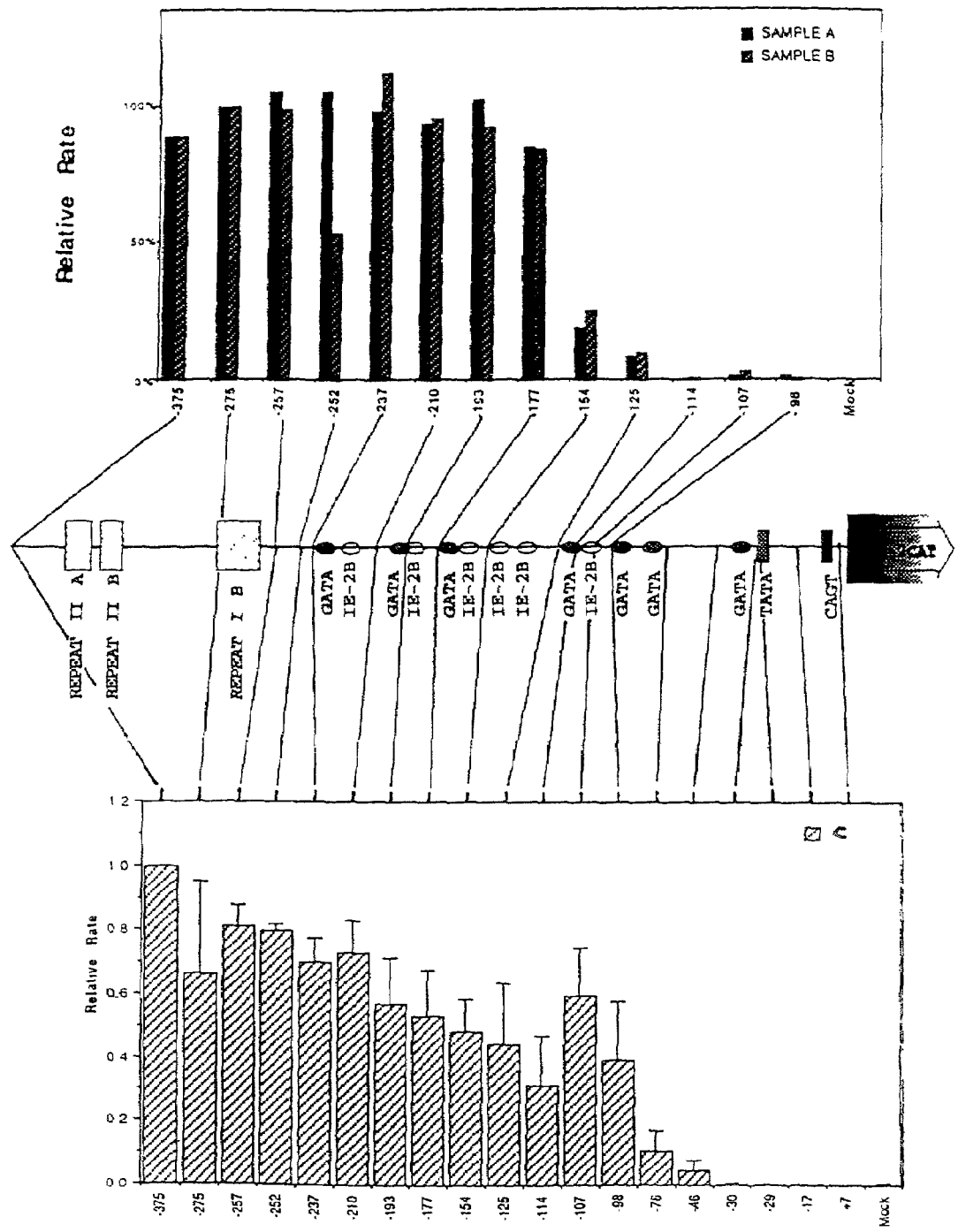
FIG. 1a. Deletion analysis of the OpMNPV ie2 promoter using the CAT reporter gene construct pIE2CAT. The graph shows the relative rates from two representative sample experiments using Sf9 (samples A and B) and Kc1 (C). All rates are given relative to deletion −275 which was given a value of 100%. The numbers below the graph indicate the 5' end of the promoter deletion constructs relative to the transcriptional start site. The schematic below the graph shows a diagram of the OpMNPV ie2 promoter and the approximate location of specific motifs which include the GATA elements (black circles), IE2B elements (open circles), Repeat I B and Repeat II A and B (hatched boxes), TATA box and CAGT transcriptional start sites (black boxes). The shaded arrow represents the CAT open reading frame. The lines connecting the graph with the schematic designate the approximate locations of 5' end of the deletions on the OpMNPV ie2 promoter.

The pIE-2CAT 5' to 3' deletion constructs were transfected into Sf9 and Kc1 cells, the cells harvested and processed for CAT assays (Neumann et al., *BioTechniques*, 5: 444–448 (1987)) and the results summarized in FIG. 1a. The minimal or basal promoter required to obtain detectable levels of CAT expression from the Op ie2 promoter in Ld652Y, Kc1 and Sf9 cells was 125 bp, 46 bp and 98 bp upstream from the transcription start site, respectively (FIG. 1a). Fine deletion analysis of the Op ie2 promoter region was conducted to determine the functional significance of the Op ie2 specific regulatory elements. Deletions up to the –177 bp did not significantly affect maximal CAT expression in either Sf9 and Ld652Y cells (the sequence of IE-2 from –177 bp to 0 bp in FIG. 2a corresponds to SEQ ID NO: 1 from bp 351 to bp 527). Further deletion of an additional 24 base pairs to position –152 results in up to a 75% reduction of CAT expression. The region between positions –177 and –152 contains a GATA and IE2B element pair. Expression is further reduced to approximately 10% of maximal levels when an additional 30 bps are deleted from positions –154 to –125. This region contains two IE2B elements. Further deletion of base pairs –125 to –114, which eliminates most of a GATA sequence in a GATA-IE2B element pair, results in almost undetectable levels of expression.

In some embodiments, with Kc1 cells, there may be a correlation between decline in promoter activity and increasing 5' promoter deletion (FIG. 1a). However unlike the lepidopteran cell lines, only a single GATA sequence is required for minimal detectable promoter activity in Kc1 cells. The addition of more GATA copies increases promoter activity in Kc1 cells as does the inclusion of GATA-IE2B sequences. Full promoter activity in this embodiment is achieved when the Repeat IIA and B are present.

These results indicate that the GATA-IE2B pairs are regulatory elements of the Op ie2 promoter. These data suggest that functional variations of the Op ie2 promoter may be constructed in accordance with the present invention that include sequences homologous to the Op ie2 sequences between –177 to –114. In particular, functional new promoters may be designed that include sequences homologous to the GATA IE2B element pair.

Figure 1B:
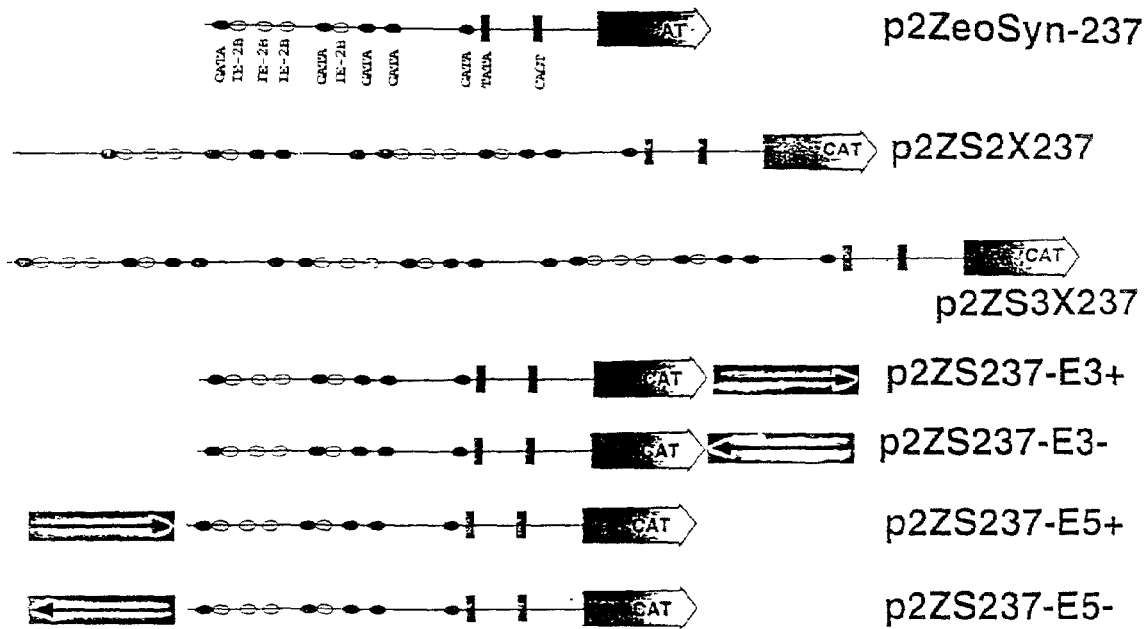
FIG. 1b. Analysis of chimeric synthetic OpMNPV ie2 promoter constructs using the CAT reporter construct. A base promoter designated p2ZeoSyn-237 included all the GATA and IE-2B sequences up to nucleotide −237. The effect of duplicating and triplicating this sequence is compared in Ld652Y, Sf9 and Kc1 cell lines. In addition the positional effects of an enhancer (OpE) found 3' to the ie-2 gene, was studied with the comparative results in various cell lines shown in the figure.
Figure 1B:
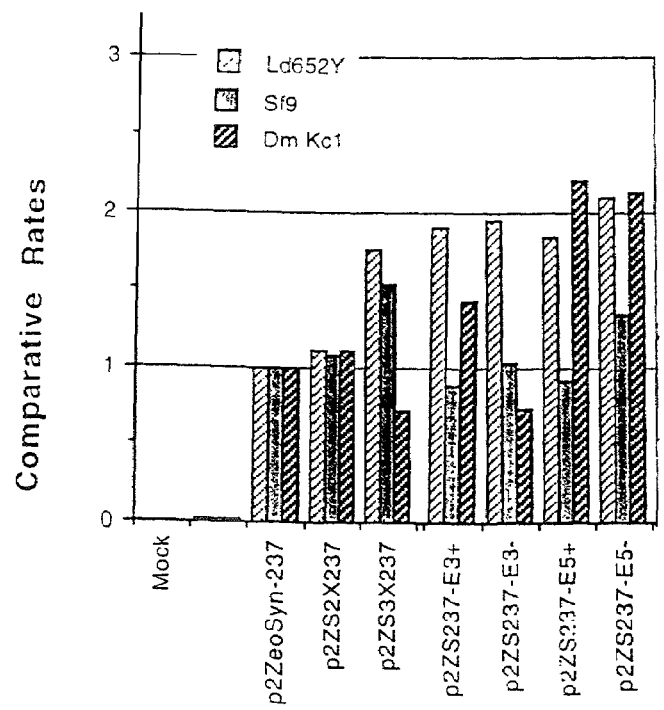

A study of constructing chimeric promoters, in order to increase promoter activity, utilizing components of the ie-2 promoter was also done (See FIG. 1b). Utilizing the –237 5' deletion construct as the base (p2ZS237), a number of synthetic chimeric promoter combinations were made and tested in three cell lines using the CAT reporter. Duplicating the 237 region resulted in a minimal increase in promoter activity over the p2ZS237 construct. Triplicating the region caused a 1.8 and 1.5 fold increase in CAT activity in Ld652Y and Sf9 cells respectively, while in Kc1 cells a decrease in in activity was seen. An enhancer sequence (OpE) identified downstream of the Opie-2 gene was also added to the construct either 5' or 3' to the base-promoter/CAT gene, in either the plus or minus orientation. The enhancer sequence OpE is identified as 12 complete or partial repetitions of the 66 bp element SEQ ID 16 5'-CCTTT CAAGC GCGTGCG-CAC CCGAAAAGCA GGGTCGCCGC TGACGCACTG CTAAAAATA GCACGCG-3' (Theilmann and Stewart, Virology 187:97–106 (1996)) In all cases inclusion of the enhancer OpE allowed approximately a 2 fold increase in activity over the base promoter in Ld652Y cells. With Sf9 cells, only when the enhancer was 5' to the promoter in the minus orientation was increased promoter activity seen. Kc1 cells showed a two fold increase in promoter activity with the enhancer 5' to the promoter in either orientation. The plus orientation of the enhancer 3' to the gene gave a 1.5 fold increase in activity while in the minus orientation a decrease in promoter activity was seen.

These results provide further evidence that various chimeric promoter combinations are useful for increasing protein production from various cell lines, in one embodiment the p2ZS237-OpE5—combination provides the most enhanced activity in cell lines.

FIG. 2 shows an alignment of the promoter sequences from the OpMNPV ie2 gene and the homologous ien gene from the related AcMNPV. The alignment was performed using the UWGCG GAP program (Devereux et al., *Nucl. Acids Res.*, 12: 387–395 (1984)). The sequence alignment in FIG. 2 shows that the –177 to –114 region of Op ie2, which is required for maximal Op ie2 activity, contains almost no homology to the AcMNPV ien promoter. The ien promoter does not include the IE2B element of the Op ie2 promoter. A further distinction between the Op ie2 and ien promoters is apparent from the results of the deletion of the Op ie2 –275 to –257 region. The –275 to –257 Op ie2 deletion removes Repeat IB which is highly homologous to an element in the AcMNPV ien promoter shown to be a positive cis-acting regulatory element for the AcMNPV ien promoter in Sf9 cells (Carson et al., *J. Virol.*, 65: 945–951 (1991)). The deletion results disclosed herein indicate that a complete copy of the Repeat IB region is not essential for high level expression of Op ie2 in Sf9 cells, distinguishing the Op ie2 promoter functionally from the AcMNPV ien promoter.

Characteristics of the Op ie2 Promoter

There are a number of unexpected advantages associated with the use of the Op ie2 promoter in shuttle vectors of the present invention. As discussed above, in shuttle vectors of the invention, the Op ie2 promoter exhibits unexpectedly higher levels of heterologous gene expression compared to the enhancer-less Ac ie1 promoter in either *D. melanogaster* or *Spodoptera* cell lines. In addition, the β-galactosidase assays of transformed cell lines disclosed herein indicate that the activity of the Op ie2 promoter is restricted to insect cells, with no detectable function in mammalian cell lines.

This latter finding is surprising, given that the opposite result, ie. active promotor function in mammalian cells, has been reported for the Ac ie1 promoter (Carbonell et al., J. Virol., 56: 153–160 (1985)).

The unexpected finding that the Op ie2 promoter does not function in mammalian cells confers vectors of the present invention with an important advantage over prior art vectors that use promoters that may function in mammalian cells. Use of vectors of the present invention incorporating the Op ie2 promoter minimizes the potential for accidental transfer of active heterologous genes to non-target organisms. Accordingly, use of such vectors of the present invention may circumvent the application of the restrictions that are properly imposed on transgenic studies where the nature of the relevant gene constructs raises the possibility that heterologous genes could be transferred to, and expressed in, unintended hosts.

The Op ie2 sequence elements identified herein by deletion analysis may be responsible for the unexpected properties of the Op ie2 promoter: activity in a broad range of insect cells that are both permissive and non-permissive to replication of the intact baculovirus; lack of detectable activity in mammalian cells; and, expression levels rivaling that of other related promoters but without the requirement for enhancer elements. Those skilled in this art will recognize that the precise sequence of the naturally occuring Op ie2 promoter may be modified to a certain degree to provide promoters that function in the same way to provide similar results, such modifications are within the scope of the present invention.

As used herein to refer to nucleic acid sequences, the terms "homology" or "homologous" denote a degree of sequence identity and functional similarity. Naturally occuring homologous sequences may be evolutionarily related, in the sense that they share a common ancestral sequence. Homologous sequences may also be created artificially through synthesis or mutagenesis. In either case, homologous sequences as identified herein exhibit a sufficient degree of sequence identity to confer similar biological functions on the sequences. The term "homology" is used herein to refer to the extent of sequence identity between two sequences, so that homologous sequences may have varying degrees of homology, ie. sequence identity. Those skilled in this art recognize that sequences that have substantial homology in functionally important segments of a sequence, such as the GATA and IE2B Op ie2 sequence elements identified herein by deletion analysis, may exhibit similar biological properties, even where other regions of such sequences do not show significant homology. Homologous sequences preferably have regions of substantial homology. Substantial homology between sequences, or between portions of sequences, means at least 75% sequence identity, preferably at least 90% sequence identity and more preferably at least 95% sequence identity between such sequences.

In one embodiment, the present invention comprises an insect promoter having homology to, and capable of functioning as, an immediate early baculovirus promoter. Such a promoter may exhibit homology to any naturally occuring immediate early baculovirus promoter, and would be capable of functioning in place of such a promoter to mediate gene expression in the baculovirus system. Such promoters preferably have substantial homology to a naturally occuring immediate early baculovirus promoter in functionally important regions of such a naturally occuring promoter, such as the GATA and IE2B Op ie2 sequence elements identified herein by deletion analysis. Alternatively, such promoter sequences may exhibit substantial homology to an entire naturally occuring immediate early baculovirus promoter, such as Op ie2. Alternatively, an insect promoter having homology to, and capable of functioning as, an immediate early baculovirus promoter may be characterized by the property of hybridizing to such an immediate early baculovirus promoter under stringent conditions. Stringent conditions for such hybridization are sequence dependent and will be different in different circumstances. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of perfectly matched sequences hybridize. In some embodiments, stringent conditions will be those in which the salt concentration is about 0.02 molar or lower at pH 7 and the temperature is at least about 60° C. for relatively short sequences.

EXAMPLE 1 a) Expression of Human Melanotransferrin (p97)

The ability of vectors of the invention to direct the expression of a highly modified heterologous proteins was examined by generating constructs containing a cDNA encoding human melanotransferrin (also known as p97) under the control of either the constitutive (Op ie2) or inducible (Mtn) promoters.

Melanotransferrin is a sialoglycoprotein that is transported to the cell's outer surface where it is attached via a glycosylphosphatidylinositol anchor rather than by typical hydrophobic transmembrane domains (Food et al., *J. Biol. Chem.*, 269: 3034–3040 (1994)). The protein was first described as a melanoma-specific diagnostic marker (Brown et al., *Proc. Natl. Acad. Sci. USA*, 78: 539–543 (1981)) and was subsequently shown to be present at elevated levels in the brain tissues of Alzheimer's patients (Jefferies et al., *Brain Res.*, 712: 122–126 (1996)). The inducible p2ZMtn97 and constitutive p2ZOp2C97 constructs were generated by cloning an EcoRI-NruI fragment from pA3-2 containing the entire protein-encoding region from the p97 cDNA into the EcoRI-PvuII site of the mammalian expression vector pZeoSV to generate pZeoSV97. Subsequently, an EcoRI-BglII fragment containing the p97 coding region plus an SV40 pA sequence was subcloned from pZeoSV97 into the EcoRI-BamHI site of p2ZOp2A to generate p2ZOp2C97 (a constitutive expression construct). In another series a SpeI-BglII fragment from pZeoSV97 was subcloned into the XbaI-BglII site of p2ZMtn to generate p2ZMtn97 (an inducible expression construct). Cells were transformed with 2 μg of CsCl-purified DNA and 10 μl of Cellfectin as described previously. In transient assays the cells were harvested 48 hours after transformation, pelleted at 4,000×g in a microcentrifuge and resuspended in 50 μl of cell lysis buffer [20 mM Tris-HCl (pH 7.2), 0.15 M NaCl, 2 mM EDTA, 1% NP40 and 0.5 mM phenylmethylsulphonyl fluoride]. Stably transformed clonal cell lines were selected as described above, however, Sf9 did not require the addition of feeder cells to the micro-titre wells. Western blot analysis was conducted by electrophoretically separating 10 μg of protein on 10% non-denaturing SDS-PAGE gels and transferring to nitrocellulose membranes. p97 protein was detected using the L235 anti-p97 monoclonal antibody as the primary antibody at a 1/10 dilution of culture supernatant in phosphate-buffered saline and horseradish peroxidase-conjugated goat anti-mouse antibody (BioRad, Richmond, Calif.)

as the secondary at a 1/20,000 dilution followed by detection with the ECL chemiluminescent system (Amersham, Oakville, ON).

Western blot analysis of transiently transformed insect cell lines using a p97-specific monoclonal antibody revealed that Sf9, *D. melanogaster*, and to a lesser extent Ld652Y, cell lines were capable of expressing detectable levels of p97 (FIG. 11A). This demonstrates the need for systems, such as we have engineered, that are capable of expression in a variety of cell lines. Stable, transformed Sf9 and SL2 clonal cell lines were generated which express p97 using either the constitutive ie2 or inducible Mtn promoters, respectively (FIG. 11B). Under selection these cell lines showed no decline in p97 expression after 12 passages over the course of three months. As was the case with the β-galactosidase producing cell lines, Southern blot analysis revealed a correlation between vector copy number and the relative levels of protein expression. The molecular weight of p97 produced by the Sf9 cells was similar to that of the baculovirus-expressed p97, whereas the molecular weight of the p97 produced from the same construct in *D. melanogaster* cells was slightly less. The p97 derived from the baculovirus system has a slightly lower molecular weight than the human p97. Two dimensional electrophoresis revealed that the difference in molecular weight between the p97 expressed in human cells and the p97 expressed by the baculovirus in Sf9 cells, is due to a lack of complex carbohydrate modifications. Finally, the L235 monoclonal antibody used to detect p97 is specific for an epitope encompassing a disulfide crosslink within the protein. The p97 protein is not only highly processed but also highly folded, thus detection of recombinant p97 in these insect cell lines not only reflects their ability to synthesize the polypeptide but also to manage complex secondary and tertiary structural organizations.

b) Localization of Recombinant p97 in Transformed Insect Cells

Two forms of the p97 protein occur naturally in mammals. Approximately 80% of the human p97 attached to the cell surface via a glycosyl phosphatidylinositol (GPI) anchor covalently linked to the carboxyl terminus of the protein. A second form which constitutes about 20% of the total p97 is exported out of the cell into the extracellular fluid by an, as yet, unknown mechanism (Food et al., *J. Biol. Chem.*, 269: 3034–3040 (1994)).

Indirect immunofluorescence was used to determine the precise cellular localization of the heterologous p97 expressed in insect cell lines. Transformed cells were allowed to adhere to glass coverslips, which had previously been coated with a solution of 1 mg/ml poly-L-lysine (400,000 MW) and allowed to dry, for 30 minutes. The slides were rinsed in phosphate buffered saline (PBS) and fixed for five minutes in freshly prepared 4% paraformaldehyde followed by a 45 second incubation in a 1:1 solution of methanol:acetone. The slides were rinsed three times in PBS, then incubated in 0.5% Triton X-100 in PBS for 10 minutes followed by three additional rinses in PBS. The cells were blocked for 20 minutes in FATS (20% fetal calf serum, 0.5% Tween-20 in PBS) followed by a 60 minutes incubation with the L235 anti-p97 monoclonal antibody (used as undiluted hybridoma supernatant) in a humidified chamber. The slides were washed three times in PBS over the course of 10 minutes and then incubated with the secondary antibody (1/30 dilution of FITC-conjugated goat-anti-mouse-Fab fragments) for 60 minutes. The slides were washed three times with PBS, mounted and viewed using either a fluorescence or confocal microscope.

These experiments indicated that the p97 expressed in the Sf9 cell lines was properly localized to the outer membrane of the cell (FIG. 12a). Conversely, transformed SL2 or Kc1 cell lines did not exhibit any fluorescence on the cell surface of the cell despite producing substantial amounts of p97 as indicated by western blot analysis. Occasionally, punctate staining within the cell was observed but this could not be localized to a specific region or organelle and thus may be cytoplasmic. This phenomenon may be related to the reduced size of the p97 expressed in either of the *D. melanogaster* cell lines, since it is well known that the post-translational addition of complex carbohydrates to proteins while in the endoplasmic reticulum is associated with proper localization. Despite a slight reduction in molecular weight, Sf9 cells apparently are capable of conducting sufficient core modifications with this particular protein to allow proper localization, whereas, *D. melanogaster* cell lines are not. However, this in itself may be of significant advantage in that downstream purification of cytoplasmic proteins is much simpler than for proteins that must be dissociated from membrane components. This again underscores the need for an insect transformation system that functions in cell lines derived from different genera of insects so that the specific post-translational processing capabilities of such different cell lines may be assayed efficiently.

c) Quantification of Recombinant p97 Expression

The amount of p97 produced by the transformed insect cell lines was quantitatively determined using an indirect immunofluorescence assay. The p97 was first released from the cell surface by cleavage with the GPI-specific enzyme phosphatidylinositol phospholipase C (PI-PLC) and then immunoprecipitated from supernatant using a p97 specific antibody. The amount of p97 in the precipitate was determined by incubation with a labeled antibody (in this case goat-anti-mouse-IgG-FITC) and quantitated using a fluorometer. Using equivalent numbers of cells the Sf9 clone (C.16) resulted in 4,000 fluorometric units of cell surface p97 expression, whereas, recombinant FACS-selected amplified Chinese hamster ovary (CHO) cells expressed approximately 10,000 units at the cell surface. When the relative size and surface areas of the two cell lines are taken into account the levels of expression are comparable. Insect cell lines can typically be grown to much higher densities than mammalian cell lines, suggesting that the transformed insect cell lines of the invention would produce as much, if not more, p97 than the amplified CHO cells. The expression from the transformed Sf9 cells might be optimized in a number of ways: screening larger number of clones, by FACS selection, by increasing the expression cassette copy number through modified transformation protocols, by analyzing expression throughout the growth phase to determine the optimal time for cell harvest, or by a combination of these approaches. As expected no p97 was released from the surface of transformed *D. melanogaster* cell lines by PI-PLC cleavage.

d) Secretion of p97 Using GPI-deficient Constructs

The majority of the p97 expressed from the full length cDNA construct in the transformed Sf9 clones was associated with the cell wall. To determine if the step limiting production was in processing and attachment of the GPI anchor, a series of carboxyl terminus deletions were generated to eliminate the GPI signal sequence encoding region.

The nested 3' deletions were generated to eliminate the p97 GPI signal sequence using the exonuclease 3/S1 nuclease method (Sambrook et al., Molecular Cloning: A Laboratory Manual. Laboratory Press, Cold Spring Harbor, N.Y. 1989). Approximately 10 mg of the plasmid pA3-2 was digested with NruI, which cleaves 87 bp downstream of the stop codon, and subjected to exonuclease 3 treatments ranging from 30–180 seconds so as to remove the terminal 25 amino acids (approximately 200 bp) from the NruI site. The ends were made blunt using Klenow DNA polymerase and dNTPs, digested with HindIII which cleaves 5' to the start codon and the pooled fragments from each time point cloned into the HindIII-EcoRV site of p2ZOp2F. This vector possesses stop codons in all three frames to replace the stop codon eliminated when generating the 3' deletions.

Several pertinent deletions are shown in FIG. 12b and can be categorized relative to the amino acid sequence of the chicken homologue. Elimination of the terminal 16 amino acids (constructs −16 and −15) from the human p97 gives rise to a protein that is effectively analagous to the secreted chicken form [McNagny, K. M., Rossi, F., Smith, G. and Graf, T. 1996. The eosinophil-specific cell surface antigen, EOS47, is a chicken homologue of the oncofetal antigen melanotransferrin. Blood 87: 1343–1352] that results from differential splicing of the mRNA transcript. Constructs −20 and −21 have lost the majority of the GPI signal sequence but have retained both the alanine residue to which the GPI is attached and the most terminal cysteine residue to ensure correct protein folding. Conversely, both of these critical amino acids have been eliminated in constructs −35 and −37.

Transformation of Sf9 with deletion constructs under the control of the constitutive Op IE-2 promoter resulted in many resistant p97-expressing clones. Western blot analysis of cell pellets and the corresponding amount of concentrated culture supernatant revealed that the majority of the p97 was being secreted into the culture medium (FIG. 12c). The cell pellet of cells transformed with constructs −15, −16, −20 and −21 exhibited two proteins of slightly different molecular weights observed and likely represent intermediates arising from either glycosylation or processing of the amino terminal secretion signal peptide. Only a single distinct band was reproducibly observed in samples of culture medium. Construct −35, which does not contain the terminal cysteine residue, was also actively secreted but appeared as a larger diffuse band on the western blots. This artifact is due to the fact that non-denaturing SDS-PAGE must be used when conducting western blot analysis with the L235 monoclonal since the epitope it recognizes possesses a cysteine disulphide bond and thus the protein remains partially intact. The −35 construct does not contain the terminal cysteine residue and thus the carboxyl portion of the protein remains free and able to bind more SDS resulting in a larger but diffuse band. Nonetheless, the protein is correctly channeled to the exterior of the cell.

When transformed with the same constitutive constructs none of the resistant Drosophila cell line clones exhibited detectable levels of p97 expression. In transient assays p97 expression was detected in both the cell pellet and supernatant at approximately equivalent ratios (data not shown), however, it cannot be concluded that the protein is being secreted since the transformation process itself permeablizes the cell membrane and compromises cell integrity resulting in loss of cytoplasmic contents and/or cell death. The appreciable amount of p97 that remained associated with the cell pellet would indicate that this is most likely the case.

To determine if removal of the GPI signal sequence which results in secretion of p97 also increased the rate of synthesis a time course experiment was conducted (FIG. 12d). The amount of p97 produced was determined using an indirect immunofluorescence assay (Kennard et al., Biotechnol. Bioeng. 42: 480–486 (1993)). The highest overall rate of expression occurred in early-mid log phase but continued to accumulate well into the stationary phase and ceased only with the onset of cell death. Total maximum accumulation in the culture approached 10 mg/ml, corresponding to approximately 3.3 mg and 5 mg/106 cells for Sf9 p97-16 and p97-21, respectively. Although this amount was produced by a low density of Sf9 cells, it represents a 6–7 fold increase in production when compared to the full length GPI-anchored form expressed in transformed Sf9 cells and is equivalent to the baculovirus. Obviously, by increasing Sf9 cell density, concentrations approaching 50 mg/ml could be obtained. No attempts were made to express the GPI-deficient form in either mammalian cells or using the baculovirus system but a similar increase in productivity might be expected. Western blot analysis revealed that the protein remained intact for several days in the culture effluent despite the onset of cell death and lysis (FIG. 12e).

These results demonstrate that minor modifications of the native protein may facilitate transport throught the cell and/or secretion out of the cell. Similar constructs may be adapted to confer similar properties in mammalian systems. This includes both cells grown in culture and chimeric or transgenic animals using appropriate mammalian expression vectors.

EXAMPLE 2 a) Expression of Insect Ion Transport Peptide (ITP)

To further illustrate the utility of the insect protein expression system of the invention, the system was used to test the ability of several insect cell lines to express the secreted insect ion transport peptide hormone (ITP). In vivo ITP is secreted by the corpus cardiacum and promotes salt and water readsorption in the locust (Shistocerca gregaria) ileum. In addition to being secreted the protein also requires extensive amino and carboxyl terminal proteolytic processing, disulfide bond formation and possibly amidation at the carboxyl terminus for activation (Meredith et al., J. Exp. Biol., 199: 1053–1061 (1996)).

A plasmid vector containing an ITP expression cassette was constructed as follows: A 405 bp SmaI-EcoRI cDNA fragment containing the ITP coding region was inserted into the ScaI-EcoRI site of pZeoSV. This intermediary plasmid was then cleaved with HindIII and the ends made blunt with Klenow DNA polymerase and dNTPs followed by cleavage with NotI to remove a 630 bp fragment containing the ITP open reading frame fused to the SV40 transcriptional termination and pA signal sequence. This fragment was inserted into p2ZOp2A that had been cleaved with EcoRI, made blunt with Klenow DNA polymerase and dNTPs and then cleaved again with NotI to generate plasmid p2ZOp2C-ITP.

Several insect cell lines were transformed with 2 μg of CsCl-purified plasmid DNA and 10 μl of Cellfectin as described above. Approximately 48 hours after transformation the cells were centrifuged at low speed (3,000×g) and the supernatant assayed for biological activity according to Audsley et al., J. Exp. Biol., 173: 261–274 (1992). High levels of activity were detected only in the supernatants of transformed D. melanogaster cell lines, Kc1 and SL2 (FIG. 13a). Much lower levels of activity were detected in the lepidopteran cell line, Sf9, with no activity present with Ld652Y or the Trichoplusia ni cell line, Hi5.

When ITP was expressed in the AcMNPV baculovirus expression system, levels of biological activity were approximately 100 fold less than that observed with the D. melanogaster cell lines of the invention. This may be due to a variety of factors, however, peptide sequencing of the baculovirus-expressed ITP revealed that the amino terminus of the peptide was incorrectly processed, which could result in reduced activity. In addition, we generated several stably transformed Kc1, SL2 and Sf9 cell lines expressing recombinant ITP. The D. melanogaster cell lines stably expressed and exported high levels of ITP, based on biological assays, whereas the Sf9 cell lines produced more moderate levels of biologically active product. These results demonstrate that the post-translational processing ability of stably transformed insect cell lines of the invention differs markedly from that of a lytic baculovirus expression system.

EXAMPLE 3 a) Expression of Factor X

The insect expression system was also used to test the ability of several insect cell lines to direct secretion of human Factor X using a human transferrin (Tf) secretion signal. Factor X is a plasma glycoprotein that participates in the blood coagulation cascade (Davie et al;, Adv. Enzymol. Relat. Areas Mol. Biol. 48:277–318 (1979)). It is composed of a 16.9 kDa light chain and a 42.1 kDa heavy chain held together by a disulphide bond. The E2 domain of Factor X contains the activation peptide and the catlytic domain and is defined as the DNA sequence from 399 to 1456 of the human Factor X cDNA (Leytus et al., Biochem. 25:5098–5102 (1986)).

A plasmid vector containing the E2 domain of Factor X was created as follows. A 1.2 kb HindIII/EcoRI fragment containing the Tf secretion signal, the E2 domain of FX and a Histidine x6 tag was cloned into the HindIII/EcoRI site of p2ZOp2F.

Several insect cell lines were transformed with 2 ug of Qiagen purified plasmid DNA and 10 ul of Cellfectin as described above. Approximately 48 hours after transformation the culture was collected and the cells were removed by a low speed (3,000×g) centrifugation.

Western blot analysis was done by separating 20 ul of the supernatant in non-reducing loading buffer on a 10% SDS polyacrylamide gel and transferring to nitrocellulose. Factor X protein was detected using a commercially available anti-Factor X polyclonal antibody as the primary antibody at a 1/5000 dilution, horseradish peroxidase-conjugated goat anti-rabbit antibody (BioRad, Richmond, Calif.) as the secondary at 1/20,000 followed by detection with the ECL chemiluminescent system (Amersham, Oakville, ON).

Western blot analysis of both transiently transformed and stable transformed polyclonal cell lines demonstrated that Factor X was efficiently secreted into the medium using the transferrin signal sequence in all cell lines tested (FIG. 13b). This once again demonstrates the versatility of the Op ie-2 promoter in the expression of heterologous proteins from a number of insect cell lines. It also demonstrates the ability of insect cells to correctly process a human transferrin secretion signal.

The Factor X protein produced can be collected from the media by binding of the Histidine x6 sequence to a Ni-NTA agarose column (Qiagen). When the collected protein is cleaved at the activation peptide, the protein has similar activity to the natural activated human Factor X. This indicates that all the proper post-translational modifications for Factor X are carried out appropriately in insect cells.

Construction of Transposon-Based Transformation/Protein Expression Vectors

Transposon-based expression vectors may be constructed comprising portions of the transposable element DNA in proper orientation, functionally equivalent to the transposon inverted terminal repeats and the adjacent DNA sequences that are required for transposition. The amount of adjacent sequence required for transposition may be predetermined by biochemical assays, such as DNA footprinting analysis using the transposase enzyme and/or by tests for biological function. Transposon-based vectors of the invention may contain a heterologous protein expression cassette placed within the regions of a transposable element that are essential for transposition.

Transposon-based vectors of the invention may or may not include the transposase enzyme coding region. The transposase gene may be placed under the control of an inducible promoter. In one embodiment, the transposase gene may be integrated into host insect cells that are intended to receive vectors of the invention. In an alternative embodiment, an inducible transposase gene may be placed on a second helper plasmid which is co-transformed with an expression cassette-containing transposon of the invention. In such an embodiment, the helper plasmid with the transposase gene may lack the functional inverted terminal repeats of the transposable elements and therefore will be unable to integrate into the host genome via transposition.

Another embodiment is the cotransfection with RNA, produced in another system such as the Sindbis Expression System or InvitroScript Cap System (Invitrogen Calif., USA) that contains the transposase message which is readily translated into the transposase protein inside the cell, with the expression-cassette-containing transposon of the invention. In another embodiment, the transposase protein purified using known biochemical techniques can be co-transformed with the expression cassette-containing transposon of the invention. DNA plasmids that contain the P-element, hobo, mariner and other insect based transposons are known and are readily available in a variety of forms. The present invention comprises transposon-based expression cassettes based on the P-element, mariner and the hobo elements to be used in dipteran cells. In accordance with another aspect, the invention comprises mariner and hobo-based transposon expression vectors for use in a wide array of cell lines. The invention may be adapted to work using other transposons capable of transposition in an insect cell. All such vectors comprise the terminal inverted repeats that are functionally involved in transpostion, and all information necessary for function of the expression cassette is located within the functional boundaries of the inverted repeats.

To adapt the Zeocin selection system of the invention for use in transposon-based expression vectors of the invention, P-element based vectors were constructed. The vectors are designated p2ZOp2Aπ and p2ZOp2Bπ.

The vector p2ZOp2Aπ contains an expression cassette within the boundaries of the P-element ends, constructed as follows: A 1.8 kb PvuII/NdeI fragment from plasmid pDM26 (Mismer and Rubin, Genetics, 116: 565–578 (1987)) which contains a portion of the D. melanogaster white gene flanked by the P-element inverted terminal repeats was inserted into the SacII site of the expression cassette p2ZOp2A which had been made blunt using T4 polymerase. The expression cassette inserted in this manner is flanked by the P-element inverted repeats and has three unique restriction enzyme sites for the insertion of foreign genes (FIG. 14).

The vector p2ZOp2Bπ contains additional unique restriction enzyme sites for foreign gene insertion. This vector was constructed by inserting the expression cassette p2ZOp2A in the opposite orientation to its insertion in p2ZOp2Aπ.

The p2ZOp2Aπ and p2ZOp2Bπ transposon-based shuttle vectors may be used for cloning and gene manipulation in *E. coli* and for transformation of either insect cell lines or whole insects (these vectors have been used to transform whole *D. melangaster*) via heterologous recombination or, if a transposase source is present, via transposition. Transformants may be selected by Zeocin resistance.

Known P-element based shuttle vectors use separate eukaryotic and prokaryotic selectable markers, such as the hygromycin B phosphotransferase or neomycin phosphotransferase genes under the control of *D. melanogaster* promoters for eukaryotic selection, and antibiotic selectable markers such as ampicillin or tetracyline resistance for selection in bacteria. The use of separate selectable marker genes in a shuttle vector considerably increases the size of such prior art vectors and limits their utility for the manipulation and insertion of large genes. The present invention addresses this problem through the use of the chimaeric Op ie2-EM7 promoter (or the Op ie2 promoter alone, with cryptic prokaryotic promotion from within the Op ie2 promoter sequence) to direct expression of the Zeocin resistance gene for selection in both eukaryotes and prokaryotes.

In one aspect the invention comprises a Zeocin resistance protein expression vector based on the hobo transposable element. The plasmid p1ZOp2Ahobo was constructed by inserting a NarI/PvuII fragment from pUChobo containing the hobo inverted terminal repeats, into the SacII site of p1Zop2A, which had been made blunt with T4 DNA polymerase (FIG. 14). In this vector three unique restriction sites are available for cloning foreign protein-encoding genes under the control of the ie2 promoter.

To test the transposon-based gene expression system of the invention, several reporter constructs were created (FIG. 14) as follows:

The plasmid pDM79IE1was constructed by inserting a 650 bp SalI-BamHI fragment from pOPIE-1B74BamHI containing the Op ie1 promoter region into the SalI-BamHI site of pDM79.

The plasmid pDM79IE2 was constructed by first inserting a 700 bp HindIII-BamHI fragment from pOPIE-NΔBamHI containing the Op ie2 promoter region into the HindIII-BamHI of pBKSII to generate the intermediate pBKOpIE2 to place a SalI site in the 5' proximal region. A SalI-BamHI fragment was then subcloned into pDM79.

To construct the plasmid pDM79IE2GFP, an 810 bp fragment from pGFP (Clonetech, Palo Alto, Calif., USA) containing the GFP-encoding region was prepared by cleavage with SpeI. The overhang was partially repaired with Klenow DNA polymerase using dCTP and dTTP, followed by cleavage with BamHI. The resulting fragment was inserted into pAcIE1$^{hr}$/PA that had been cleaved with HindIII, partially repaired with Klenow DNA polymerase using dATP and dGTP, and then cleaved with BgIII. This plasmid, pAcIE$hr$GFP was subsequently cleaved with SalI, the ends made blunt using Klenow DNA polymerase with dNTPs, and then religated to remove the SalI site to form pAcIE$^{hr}$GFPSal$^-$. The 4.0 kb β-galactosidase reporter gene in pDM79 was replaced with the GFP reporter gene by insertion of a 850 bp KpnI-EcoRI fragment from pAcIE$^{hr}$GFPSal$^-$ encoding the GFP open reading frame followed by a 200 bp EcoRI fragment containing the SV40 transcriptional terminator. Finally, the Op ie2 promoter was inserted as a 750 bp SalI-BamHI fragment from pBKOpIE2 into the SalI-BamHI site to generate pDM79GFP.

To construct the plasmid pDM79IE-2-Gal, a 500 bp SalI/XhoI fragment containing a segment of the Gal4 gene was inserted into the SalI site of pDM791E-2. This vector is useful for detecting the mobile element in the SL2delta2,3 cell line via Southern analysis as background signal from probing with the gal4 segment is negligible when compared to other probes used for detecting the element.

The plasmid p1ZOp2AhoboGFP was constructed by inserting an 800 bp EcoR1 fragment from pGFP10.1 containing the GFP-encoding region into the EcoRI site of p1ZOpp2Ahobo.

Construction of Transposase Producing Cell Lines

Introduction of a fully functional transposon-based expression cassette, capable of both integration into the genomic DNA by transposition and subsequent re-mobilization, is facilitated if the transposase enzyme is present within the cell nucleus at the time of delivery of the vector DNA. This is important since, in the absence of transposase, it is more likely that the vector will randomly integrate via heterologous recombination into the cellular DNA, rather than integrating by transposition. Random integration may disrupt the integrity of the transposon. In addition, plasmid DNAs that have integrated via heterologous recombination may be unstable and prone to excision from the genome unless strong selection pressures are applied.

The transposase enzyme can be made available at the time of delivery of vector DNA in a number of ways, including:

1) by stably incorporating a modified version of the transposase gene into the genome of the cell line prior to transformation, in which case the native constitutive transposase promoter may be replaced by a regulatable promoter;

2) by cotransformation with the vector and a helper plasmid, the helper plasmid being capable of expressing the transposase gene but incapable of transposition into the genome;

3) by cotransformation with the vector and the transposase enzyme itself;

4) by cotransformation with the vector and transposase encoding mRNA, which when translated will produce the transposase enzyme; or, 5) by previous of cotransfection with a defective insect virus that expresses the transposase. This virus is unable to replicate and thus can be used to deliver DNA or RNA to the cell.

These and other approaches may be used that function to make transposase available within the cell nucleus, at the time of delivery of vector DNA, to direct integration of the transposon-based cassette via transposition.

One aspect of the invention comprises a transgenic cell line that can be induced to produce transposase prior to transformation with the expression cassette (FIG. 15). This approach may be used to maximize the probability that integration will occur via transposition, since transposase expression may be induced in such cells relatively quickly, typically in a matter of hours.

The native form of the P-element transposase mRNA is incorrectly processed in somatic tissue and the natural transposase gene would not therefore function in immortalized cell lines. In one aspect of the invention, a P-element transposase source has been used which has been modified to delete the intron between exon 2 and exon 3 to yield a gene, referred to as Δ2-3, that is capable of producing active transposase in both germ-line and somatic tissues. In accordance with this aspect of the invention, production of transposase may be controlled using a regulated inducible promoter, for example the *D. melanogaster* metal-responsive metallothionein (mtn) or galactose-repressible (gal) promoters. The use of inducible promoters facilitates production of high levels of transposase in response to induction, and facilitates repression of expression in the absence of inducer. For example, the mtn promoter can efficiently regulate the Δ2-3 transposase gene even when there are more than 100 copies of the gene per cell.

Other transposase proteins may be used to mobilize transposon-based expression cassettes in conjunction with other transposable elements. For example, other transposases may be used in conjunction with the transposable elements hobo, hermes, minos, or mariner. In each case the transposase gene may be placed immediately downstream of a regulable promoter. The promoter may also be operably linked to an expression cassette containing a selectable resistance marker for such antibiotics as hygromycin B, G-418, methotrexate, or Zeocin. The transposase containing vector may be transfected into the appropriate cell line and selection applied. Production and regulation of the transposase may be monitored by Western blot or Northern blot analysis and by functional assays of transposition using transposon-based excision indicator plasmids.

A *D. melanogaster* SL2 cell line (MT Δ2-3) expressing the P-element transposase under the control of the mtn promoter was made previously and is available from the American Type Culture Collection as ATCC CRL-10901 (Kaufman et al., *Cell*, 59: 359–371 (1988)). The manner in which this transposase gene was inserted into the expression construct and the large number of constructs integrated into the genome of the cell line results in detectable amounts of transposase gene expression in the absence of induction. Cell lines such as this which constitutively express transposase may not be the most advantageous hosts for creating transformed, inducible, protein expressing cell lines in accordance with the invention. The use of this cell line in accordance with the invention does, however, demonstrate the utility of the system of the invention for introducing and amplifying a transposon-based expression cassette.

In accordance with other aspects of the invention, transposase constructs have been created and inserted into SL2 cell lines at much lower copy numbers than in ATCC CRL-10901 cells, to provide tighter regulation of transposase production in a novel cell line designated SL2MTΔ2-3. To construct this cell line, a 2.4 kb Δ2-3 P-element transposase gene was amplified by PCR and inserted directly downstream of the mtn promoter contained in the vector pMT-2 (Kovach et al., *Insect Mol. Biol.*, 1: 37–43 (1992)). This plasmid contains a hygromycin-B resistance marker. The resulting vector was used to transform *D. melanogaster* SL2 cell lines. Cell lines with low copy numbers of the mtn-transposase construct were selected. Polyclonal antisera was generated against the P transposase protein, and was used to show that the SL2MTΔ2-3 cell line produces transposase of the correct molecular weight, and its expression is inducible. Transposase function was verified by transforming the SL2MTΔ2-3 cell line with an excision indicator plasmid, in which precise excision of a mini P element results in production of blue, rather than white, colonies. Mobilization of the P element was selected and verified by DNA sequencing.

Inducible transposase producing cell lines can be created for a wide spectrum of transposases, including hobo, mariner, minos, and piggyBac, as well as for retrotransposons requiring reverse transcriptase for mobility, such as copia, gypsy and Ty.

Transformation of Transposase Expressing Cell Lines

To insert engineered DNA constructs into the genome via transposition, marked transposons were created in which an Op ie1 or Op ie2 promoter-β-galactosidase reporter cassette, the bacterial ampicillin resistance gene, an origin of replication, and a heat-shock promoter-neomycin phosphotransferase selectable marker cassette were all flanked by the P element inverted repeats. This construct was introduced into the SL2MTΔ2-3 cell line under G-418 selection and expression of the β-galactosidase reporter gene was monitored. Integration of the transposon-based expression cassette via transposition into the SL2 MTΔ2-3 cell line was achieved by growing the cells to mid-log phase and inducing transposase expression with the addition of 0.25 mM copper sulfate 48 hours prior to transformation. Approximately $4 \times 10^6$ cells were pelleted by low speed centrifugation, resuspended in 1.0 ml of Graces minimal medium containing 10 μl of liposomes and 2 μg of the transposon-based vector DNA. The cell suspension was incubated for four hours at which time two mls of TC-100 complete medium was added. The cells are incubated for an additional 48 hours then selection is applied to isolate either clonal or polyclonal cell lines as described above.

The expression cassette construct integrated into a number of independent sites within the genome. Plasmid rescue of sequences flanking the transposon terminal repeats indicated that a large fraction of the constructs had been inserted into the cell's genome via transposition and not by recombination. Introduction of the constructs via transposition is important to imparting stability upon the transforming DNA sequences. In this manner, they will have integrated into independent, widely-separated sites throughout the genome and will be less subject to destabilizing effects such as gene amplification or loss resulting from tandem repeat-induced recombination. The cell lines are stable, and heterologous protein expression continues unabated in the absence of antibiotic selection for hundreds of cell generations. Similar systems based on other transposons, such as the mariner and hobo elements are within the scope of the invention.

Analysis of Genomic Integration Events

The integration of the transposon cassettes into the SL2 MTΔ2-3 cell line genomic DNA was verified by plasmid rescue of individual genomic insertions, followed by sequence analysis of the unique genomic DNA flanking the transposon inverted terminal repeats (FIG. 16*b*). In these experiments DNA was isolated from a polyclonal SL2 MTΔ2-3 cell line that had been transformed with pDM79OPIE2. Sequences flanking the 5' inverted repeats were rescued by digesting one microgram of genomic DNA with XhoI, religation of digested DNA fragments at increasingly dilute concentrations, followed by transformation of *E. coli* DH10B with the religated DNA, and plating transformed *E. coli* onto LB medium supplemented with 100 μg/ml ampicillin and 50 μl of a 20 mg/ml solution of the chromogenic β-galactosidase substrate, X-gal per plate. Colonies that were ampicillin-resistant (ie. contained β-lactamase gene present in pDM79) and were blue in appearance (resulting from transcription of the β-galactosidase gene in *E. coli* from a cryptic bacterial promoter site located in the Op ie2 promoter were isolated and the plasmid DNA analyzed. The existence of this cryptic bacterial promoter gives rise to the surprising and totally unexpected result that in some embodiments, the EM7 promoter is not absolutely necessary in shuttle vectors of the invention because the cryptic bacterial promoter in the Op ie2 promoter will serve the same function in its place. White, ampicillin-resistant colonies also appeared, these result from rescue of the construct used to introduce the mtn-transposase cassette. DNA flanking the 3' insertion sites were analyzed by digestion with XbaI, ligation, transformation of E. coli DH10B and plating onto LB medium supplemented with 100 μg/ml ampicillin and 50 μg/ml kanamycin. Colonies that were both ampicillin and kanamycin-resistant (due to transcription of the neomycin phosphotransferase gene in E. coli from a cryptic promoter located in upstream sequences) were identified and analyzed. The plasmid DNA was isolated and digested with HindIII which releases a 500 bp white gene that serves as a spacer between the 5' and 3' inverted repeats in the pDM79 vectors and is lost during transposition. None of the plasmid DNAs rescued from the transformed SL2 MTΔ2-3 cell line exhibited this 500 bp spacer fragment indicating that integration occurred via transposition and not heterologous recombination. Sequence analysis revealed that the transposons had integrated into independent sites within the genome via 'precise' transposition. Several transposons integrated into well characterized regions of the D. melanogaster genome including the heat shock locus, heterochromatic regions, as well as into other pDM79OpIE2 transposons. These well-characterized regions represent distinctly different regions of the D. melanogaster genome, confirming integration into independent sites.

Stability of Recombinant Transposon Cell Lines

The stability of the SL2 MTΔ2-3 cell lines transformed with pDM79OpIE 1 or pDM79OpIE2 was measured by continual subculture (approximately 30 passages) over the course of 26 weeks. Populations of cells that had been selected with 1 mg/ml G-418 either in the presence or absence of 100 μM CuSO$_4$ continuously produced β-galactosidase over the entire period with only minor week-to-week variations (FIG. 16a). As a further indication of stability, removal of the selective antibiotic did not result in loss of enzyme production as had been observed with constructs introduced via heterologous recombination. In accordance with one aspect of the invention, should heterologous protein production decline after an extended period of time, as a result for example of gene silencing or related phenomenon, that the protein expression may be reactivated by inducing transposition of the expression cassettes to new transcriptionally active genomic sites.

Subsequent freeze thaw cycles of the cell lines further demonstrated stability of production. Samples were placed in liquid nitrogen for several weeks, rescued and analyzed for β-galactosidase production. No decrease in B-galactosidase levels were seen over several freeze thaw cycles. Therefore, should the levels of heterologous protein production decline after continuous subculture over long periods, it should be possible to re-establish the cultures from previously frozen aliquots.

Amplification of Transposon-Based Expression Cassette

To assess the overall heterogeneity of polyclonal cell lines transformed with a transposon vector of the invention, and to determine what proportion of such cells contain amplified numbers of expression cassettes, the SL2 MTΔ2-3 cell line was transformed with the pDM79IE2GFP reporter plasmid. Examination of the cell lines indicated that approximately 20–30% of the cells expressed significantly higher levels of GFP than the rest of the population (FIG. 17). These amplified cells could be separated from the remainder of the poorly-expressing cells using a fluorescence-activated-cell-sorting system or by dilution analysis and manual selection. Should the modified transposon also contain a cassette for another heterologous gene it follows that expression of this protein would be closely correlated with GFP production. In effect, the present invention allows the use of an unobtrusive marker such as GFP to facilitate the identification of transformed cell lines that are likely to provide increased expression of a heterologous protein of interest. In this context, "unobtrusive" means that the marker gene is not significantly deleterious to the transformed cell when the unobtrusive marker is expressed. This approach also allows for transformation, selection and amplification of the expression cassette without the use of antibiotics at any stage of the process.

Expression from transformed cells isolated during the initial round of selection may be further enhanced by subsequent induction of the transposition mechanism. In some embodiments, expression of the transposase enzyme under the control of the Mtn promoter may be induced with 0.5 mM CuSO$_4$ for 24 hours, the transposase will identify the specific transposons and through replicative transposition will amplify and insert additional copies of the transposon cassette into other genomic positions. Clonal or polyclonal cell lines are established, reselected and analyzed. This process can be repeated several times until an optimal number of copies of the transposon cassette is obtained. Cell lines with optimal copies of transposon cassettes may then be scaled up for continuous protein production.

Another assessment of gene amplification was conducted as follows. The transposon containing expression cassette pDM79IE-2gal was transformed into the SL2 MTdelta2-3 cell lines as follows. SL2 MTdelta2-3 cells (1×106 cells) were plated in each well of a 6 well cell culture plate in 1 ml of Grace's medium. The cells were allowed to attach for 30 minutes and CuSO4 to a final concentration of 500 mM was added. The cells were incubated for 3 hours after which the medium was removed and the cells washed once with 2 ml of Graces's medium. One ml of Grace's medium that contained either 1 ug (P1), 100 ng (P2), 10 ng (p3) or 1 ng (P4) of plasmid DNA and 10 ul of Cellfectin was prepared as previously described, applied to the SL2 MTdelta2-3 cells and the cells incubated at 27° C. for 4 hours. After this time the medium was removed from the cells and replaced with 2 ml of TC-100 medium containing 5% FBS, 250 μg/ml G418, 200 μg/ml hygromycin and the cells incubated for 40 hours. Each well containing a different amount of transforming DNA was set up as a poplyclonal cell line. After 3 transfers (approximately 2 weeks) to new flasks a sample was removed for DNA and β-galactosidase analysis. A further sample was then subjected to 3 hours of 500 mM CuSO4, washed with 2 ml of Graces, allowed to recover for 2 days and then placed on 500 μg/ml G418, 200 μg/ml Hygromycin. After three transfers (approximately 2 weeks) a sample was taken for both DNA and B-galactosidase analysis.

The results are shown in Table 2, where Initial cell lines are the polyclonal lines set up after the first transformation, and induced cell lines are polyclonal cell lines set up after induction of that particular initial polyclonal cell line. P0 is a cell line that was transformed with 1 ug of the plasmid pDM79IE-2gal-HdIIIdel. This plasmid is the pDM79IE-2gal with a deleted 500 bp HindIII fragment, which contains the P element inverted repeats necessary for transposition. As expected no increase in B-galactosidase activity was seen with this polyclonal cell line after induction of the transposase.

TABLE 2

| Initial Cell lines | β-gal (units) | Induced Cell lines | β-gal (units) |
|---|---|---|---|
| P0-1 | 2.5 | P0-2 | 2.0 |
| P1-1 | 2.7 | P1-2 | 7.6 |
| P2-1 | 0.2 | P2-2 | 4.9 |
| P3-1 | 0 | P3-2 | 0 |
| P4-1 | 0.9 | P4-2 | 0.2 |

These results demonstate that induction of a transposase in a cell line containing an expression cassette within a transposon can lead to a cell line capable of higher production of the recombinant protein contained in the expression cassette.

Conclusion

As will be apparent to those skilled in the art in the light of the foregoing disclosure, many alterations and modifications are possible in the practice of this invention without departing from the spirit or scope thereof. Variations of the invention may be understood from the teaching of the references cited herein, all such references are hereby incorporated by reference. In some embodiments, the vectors of the invention may be adapted for use with a variety of antibiotic selection schemes. Additional promoter elements may be used in accordance with the invention to potentiate expression from baculovirus immediate early promoters. The Op ie1 and Op ie2 genes encode transcription factors that transactivate their own as well as other early and delayed-early baculovirus promoters (Theilmann and Stewart, Virology, 180:492–508 (1991); Theilmann and Stewart, Virology, 187: 84–96 (1992)). Additionally, an enhancer element has been identified adjacent to the 3' end of the ie2 coding region which functions together with the ie1 gene product to increase early gene expression from reporter constructs by 10–17 fold in Ld652Y and Sf9 cells, respectively (Theilmann and Stewart, Virology, 187: 97–106 (1992)). Stable cell lines expressing these transcriptional activators may potentiate expression by these promoters or broaden the spectrum of cell lines in which the promoters function inefficiently. In some embodiments, other more promiscuous transposable elements may be adapted to transfer the expression cassettes into cell lines derived from a larger variety of species. Accordingly, the scope of the invention is to be construed in accordance with the substance defined by the claims which follow the Sequence Listing.

Sequence Listing (1) GENERAL INFORMATION:
   (I) APPLICANT:
     (A) NAME: The University of British Columbia, Research Administration, Room 331, IRC Building
     (B) STREET: 2194 Health Sciences Mall
     (C) CITY: Vancouver
     (D) STATE: British Columbia
     (E) COUNTRY: Canada
     (F) POSTAL CODE (ZIP): V6T 1Z3
     (G) TELEPHONE: (604) 822-8596
     (H) TELEFAX: (604) 822-8589
   (ii) TITLE OF INVENTION: Insect Expression Vectors
   (iii) NUMBER OF SEQUENCES: 11
   (iv) COMPUTER READABLE FORM:
     (A) MEDIUM TYPE: Floppy disk
     (B) COMPUTER: IBM PC compatible
     (C) OPERATING SYSTEM: PC-DOS/MS-DOS

What is claimed is:

1. A shuttle vector for transforming insect cells and prokaryotic cells, comprising:
   a) a prokaryotic origin of replication;
   b) a promoter region comprising an insect promoter and a prokaryotic promoter sequence; and
   c) a selectable marker coding sequence operably linked to the promoter region, such that the selectable marker is under the transcriptional control of the insect promoter in insect cells and the prokaryotic promoter sequence in prokaryotic cells, wherein the selectable marker is thereby expressed in both prokaryotic and insect cells to confer resistance to a bleomycin/phleomycin-type antibiotic on cells transformed with the shuffle vector.

2. The shuttle vector of claim 1, wherein the bleomycin/phleomycin-type antibiotic is Zeocin.

3. The shuttle vector of claim 1, further comprising an insertion site for heterologous DNA.

4. The shuttle of claim 3, wherein the insertion site for heterologous DNA is under the transcriptional control of a second insect promoter.

5. The shuttle vector of claim 4, further comprising a heterologous DNA sequence inserted at the insertion site and under the transcriptional control of the second insect promoter.

6. The shuttle vector of claim 1, wherein the insect promoter is an immediate early baculovirus promoter.

7. The shuttle vector of claim 1, wherein the insect promoter comprises the sequence as shown in SEQ ID NO: 1 from bp 351 to bp 527.

8. The shuttle vector of claim 7, wherein the insect promoter comprises the sequence as shown in SEQ ID NO: 1.

9. The shuttle vector of claim 1 further comprising DNA transposable elements.

10. The shuttle vector of claim 9, wherein the selectable marker coding sequence is between the transposable elements.

11. The shuttle vector of claim 10, further comprising an insertion site for heterologous DNA between the transposable elements.

12. The shuttle vector of claim 11, further comprising a heterologous DNA sequence inserted at the insertion site and under the transcriptional control of a second insect promoter.

13. The shuttle vector of claim 9, further comprising an inducible transposase gene between the transposable elements.

14. Insect cells transformed with the shuttle vector of claim 1.

15. Insect cells transformed with the shuttle vector of claim 9.

16. Recombinant insect cells transformed with the shuttle vector of claim 1, wherein said insect cells express a heterologous insect ion transport peptide hormone encoded by a nucleotide sequence in the shuttle vector.

17. The shuffle vector of claim 1, wherein the insect promoter comprises a sequence having at least 95% sequence identity to SEQ ID NO: 1 from bp 351 to bp 527, and wherein the insect promoter is a functional promoter.

18. The shuttle vector of claim 1, wherein the insect promoter comprises a sequence having at least 95% sequence identity to SEQ ID NO: 1, and wherein the insect promoter is a functional promoter.

19. The shuttle vector of claim 1, wherein said insect promoter comprises SEQ ID NO: 1, and the prokaryotic promoter sequence is a cryptic promoter within said insect promoter, and wherein said cryptic promoter directs expression of said selectable marker in said prokaryotic cells.

* * * * *

SEQUENCE LISTING

```
<160> NUMBER OF SEQ ID NOS: 50

<210> SEQ ID NO 1
<211> LENGTH: 564
<212> TYPE: DNA
<213> ORGANISM: Orgyia pseudotsugata

<400> SEQUENCE: 1
catgatgata aacaatgtat ggtgctaatg ttgcttcaac aacaattctg ttgaactgtg     60
ttttcatgtt tgccaacaag cacctttata ctcggtggcc tccccaccac caacttttttt   120 gcactgcaaa aaaacacgct tttgcacgcg ggcccataca tagtacaaac tctacgtttc    180
gtagactatt ttacataaat agtctacacc gttgtatacg ctccaaatac actaccacac   240 attgaaccctt tttgcagtgc aaaaaagtac gtgtcggcag tcacgtaggc cggccttatc    300
gggtcgcgtc ctgtcacgta cgaatcacat tatcggaccg gacgagtgtt gtcttatcgt    360
gacaggacgc cagcttcctg tgttgctaac cgcagccgga cgcaactcct tatcggaaca   420
ggacgcgcct ccatatcagc cgcgcgttat ctcatgcgcg tgaccggaca cgaggcgccc    480
gtcccgctta tcgcgcctat aaatacagcc cgcaacgatc tggtaaacac agttgaacag   540
catctgttac agcgacacaa catg                                            564

<210> SEQ ID NO 2
<211> LENGTH: 44
<212> TYPE: DNA
```

<213> ORGANISM: Orgyia pseudotsugata

<400> SEQUENCE: 2
ccgcggatcg atatctgact aaatcttagt ttgtattgtc atgt     44

<210> SEQ ID NO 3
<211> LENGTH: 24
<212> TYPE: DNA
<213> ORGANISM: Orgyia pseudotsugata

<400> SEQUENCE: 3
cgggtgcgca cgcgcttgaa agga     24

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: PCR
      amplifier

<400> SEQUENCE: 4
aatttaaacg ttggtaccct cgagctcagc tgaattctgg atcct     45

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: PCR
      amplifier

<400> SEQUENCE: 5
ctagaaggat ccagaattca gctgagctcg aggtaccaag cttta     45

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: PCR
      amplifier

<400> SEQUENCE: 6
ctagaccggt catatgcggg ccgcggatcg atcgat     36

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: PCR
      amplifier

<400> SEQUENCE: 7
atcgatcgat ccgcggccgc atatgaccgt     30

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 8
tcgggtgcgc acgcgcttga aagga     25

<210> SEQ ID NO 9
<211> LENGTH: 55
<212> TYPE: DNA
<213> ORGANISM: Artificial Sequence
<220> FEATURE:
<223> OTHER INFORMATION: Description of Artificial Sequence: Primer

<400> SEQUENCE: 9
tcagctgcag atgaagaggc ctagacctat gaaaccagta acgttatacg atgtc      55

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 10
acttaagctt atagcgatga ctgcccgctt tccagtcggg aaacctgtcg            50

<210> SEQ ID NO 11
<211> LENGTH: 67
<212> TYPE: DNA
<213> ORGANISM: Artificial Sequence
<220> FEATURE:
<223> OTHER INFORMATION: Description of Artificial Sequence: Bombyxin
      secretion signal oligonucleotide fragment

<400> SEQUENCE: 11
aattatgaag atactccttg ctattgcatt aatgttgtca acagtaatgt gggtgtcaac      60
aagctta      67

<210> SEQ ID NO 12
<211> LENGTH: 67
<212> TYPE: DNA
<213> ORGANISM: Artificial Sequence
<220> FEATURE:
<223> OTHER INFORMATION: Description of Artificial Sequence: Bombyxin
      secretion signal oligonucleotide fragment

<400> SEQUENCE: 12
ctagtaagct tgttgacacc cacattactg ttgacaacat taatgcaata gcaaggagta      60
tcttcat      67

<210> SEQ ID NO 13
<211> LENGTH: 66
<212> TYPE: DNA
<213> ORGANISM: Artificial Sequence
<220> FEATURE:
<223> OTHER INFORMATION: Description of Artificial Sequence: Enhancer
      sequence OpE

<400> SEQUENCE: 13
cctttcaagc gcgtgcgcac ccgaaaagca gggtcgccgc tgacgcactg ctaaaaatag      60
cacgcg      66

<210> SEQ ID NO 14
<211> LENGTH: 462
<212> TYPE: DNA
<213> ORGANISM: Artificial Sequence
<220> FEATURE:
<223> OTHER INFORMATION: Description of Artificial Sequence:Promoter
      sequence of the OpMNPV ie2 gene -continued

```
<400> SEQUENCE: 14
ccccaccacc aacttttttg cactgcaaaa aaacacgctt ttgcacgcgg gcccatacat    60
agtacaaact ctacgtttcg tagactattt tacataaata gtctacaccg ttgtatacgc   120
tccaaataca ctaccacaca ttgaaccttt ttgcagtgca aaaaagtacg tgtcggcagt   180
cacgtaggcc ggccttatcg ggtcgcgtcc tgtcacgtac gaatcacatt atcggaccgg   240
acgagtgttg tcttatcgtg acaggacgcc agcttcctgt gttgctaacc gcagccggac   300
gcaactcctt atcggaacag gacgcgcctc catatcagcc gcgcgttatc tcatgcgcgt   360
gaccggacac gaggcgcccg tcccgcttat cgcgcctata aatacagccc gcaacgatct   420
ggtaaacaca gttgaacagc atctgttaca gcgacacaac at                     462

<210> SEQ ID NO 15
<211> LENGTH: 88
<212> TYPE: DNA
<213> ORGANISM: Artificial Sequence
<220> FEATURE:
<223> OTHER INFORMATION: Description of Artificial Sequence: Fragment of
      promoter sequence of the AcMNPV ien gene

<400> SEQUENCE: 15
gataaattta aaatgaattt ttttgcaatg caaaaaagtt cacttttgcc tgacactcca    60
tatacagtac aatctctaca aatcgtag                                      88

<210> SEQ ID NO 16
<211> LENGTH: 92
<212> TYPE: DNA
<213> ORGANISM: Artificial Sequence
<220> FEATURE:
<223> OTHER INFORMATION: Description of Artificial Sequence: Fragment of
      promoter sequence of the AcMNPV ien gene

<400> SEQUENCE: 16
ctattttatt agaatagtct acactgtacg atacgctccc aatatactac tacactatca    60
acttttttgc attacaaaaa agttcatttt tg                                 92

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Fragment of
      the promoter sequence of the AcMNPV ien gene

<400> SEQUENCE: 17
cctggcaagt tc                                                       12

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Fragment of
      the promoter sequence of the AcMNPV ien gene

<400> SEQUENCE: 18
ccccaccact attgtct                                                  17

<210> SEQ ID NO 19
<211> LENGTH: 16
<212> TYPE: DNA
<213> ORGANISM: Artificial Sequence
```

```
<220> FEATURE:
<223> OTHER INFORMATION: Description of Artificial Sequence: Fragment of
      the promoter sequence of the AcMNPV ien gene

<400> SEQUENCE: 19
tatcagtcgt gcagta                                                    16

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Fragment of
      the promoter sequence of the AcMNPV ien gene

<400> SEQUENCE: 20
ctgataaaca gtataaatac agctgccgtt ctactcgtaa gcacagttca              50

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Fragment of
      the promoter sequence of the AcMNPV ien gene

<400> SEQUENCE: 21
agcctcacag cctagtgaac agtat                                          25

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: IE2B
      promoter element

<400> SEQUENCE: 22
gacaggacgc                                                           10

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: IE2B
      promoter element

<400> SEQUENCE: 23
cttatcgtga caggacgc                                                  18

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: IE2B
      promoter element

<400> SEQUENCE: 24
aacaggaagc                                                           10

<210> SEQ ID NO 25
<211> LENGTH: 18
<212> TYPE: DNA
<213> ORGANISM: Artificial Sequence
<220> FEATURE:
```

<223> OTHER INFORMATION: Description of Artificial Sequence: IE2B
    promoter element

<400> SEQUENCE: 25
cttatcggaa caggacgc                                          18

<210> SEQ ID NO 26
<211> LENGTH: 132
<212> TYPE: DNA
<213> ORGANISM: Artificial Sequence
<220> FEATURE:
<223> OTHER INFORMATION: Description of Artificial Sequence:Native
    melanotransferrin (p97) construct
<221> NAME/KEY: CDS
<222> LOCATION: (1)..(129)

<400> SEQUENCE: 26 gac tac gtg gcg gcg ctg gaa ggg atg tcg tct cag cag tgc tcg ggc    48
Asp Tyr Val Ala Ala Leu Glu Gly Met Ser Ser Gln Gln Cys Ser Gly
 1               5                  10                  15 gca gcg gcc ccg gcg ccc ggg gcg ccc ctg ctc ccg ctg ctg ctg ccc    96
Ala Ala Ala Pro Ala Pro Gly Ala Pro Leu Leu Pro Leu Leu Leu Pro
             20                  25                  30 gcc ctc gcc gcc cgc ctg ctc ccg ccc gcc ctc tga                   132
Ala Leu Ala Ala Arg Leu Leu Pro Pro Ala Leu
         35                  40

<210> SEQ ID NO 27
<211> LENGTH: 43
<212> TYPE: PRT
<213> ORGANISM: Artificial Sequence
<220> FEATURE:
<223> OTHER INFORMATION: :

<400> SEQUENCE: 27

Asp Tyr Val Ala Ala Leu Glu Gly Met Ser Ser Gln Gln Cys Ser Gly
 1               5                  10                  15

Ala Ala Ala Pro Ala Pro Gly Ala Pro Leu Leu Pro Leu Leu Leu Pro
             20                  25                  30

Ala Leu Ala Ala Arg Leu Leu Pro Pro Ala Leu
         35                  40

<210> SEQ ID NO 28
<211> LENGTH: 84
<212> TYPE: DNA
<213> ORGANISM: Artificial Sequence
<220> FEATURE:
<223> OTHER INFORMATION: Description of Artificial Sequence: Deletion
    construct made of the melanotransferrin (p97) gene
<221> NAME/KEY: CDS
<222> LOCATION: (1)..(81)

<400> SEQUENCE: 28 gac tac gtg gcg gcg ctg gaa ggg atg tcg tct cag cag tgc tcg ggc    48
Asp Tyr Val Ala Ala Leu Glu Gly Met Ser Ser Gln Gln Cys Ser Gly
 1               5                  10                  15 gca gcg gcc ccg gcg ccc ggg gcg ccc ctg atc tga                    84
Ala Ala Ala Pro Ala Pro Gly Ala Pro Leu Ile
             20                  25

<210> SEQ ID NO 29
<211> LENGTH: 27
<212> TYPE: PRT
<213> ORGANISM: Artificial Sequence
<220> FEATURE:
<223> OTHER INFORMATION: :

<400> SEQUENCE: 29

Asp Tyr Val Ala Ala Leu Glu Gly Met Ser Ser Gln Gln Cys Ser Gly
 1               5                  10                  15

Ala Ala Ala Pro Ala Pro Gly Ala Pro Leu Ile
            20                  25

<210> SEQ ID NO 30
<211> LENGTH: 87
<212> TYPE: DNA
<213> ORGANISM: Artificial Sequence
<220> FEATURE:
<223> OTHER INFORMATION: Description of Artificial Sequence: Deletion
      construct made of the melanotransferrin (p97) gene
<221> NAME/KEY: CDS
<222> LOCATION: (1)..(84)

<400> SEQUENCE: 30 gac tac gtg gcg gcg ctg gaa ggg atg tcg tct cag cag tgc tcg ggc      48
Asp Tyr Val Ala Ala Leu Glu Gly Met Ser Ser Gln Gln Cys Ser Gly
 1               5                  10                  15 gca gcg gcc ccg gcg ccc ggg gcg ccc cta tct gac taa                  87
Ala Ala Ala Pro Ala Pro Gly Ala Pro Leu Ser Asp
            20                  25

<210> SEQ ID NO 31
<211> LENGTH: 28
<212> TYPE: PRT
<213> ORGANISM: Artificial Sequence
<220> FEATURE:
<223> OTHER INFORMATION: :

<400> SEQUENCE: 31

Asp Tyr Val Ala Ala Leu Glu Gly Met Ser Ser Gln Gln Cys Ser Gly
 1               5                  10                  15

Ala Ala Ala Pro Ala Pro Gly Ala Pro Leu Ser Asp
            20                  25

<210> SEQ ID NO 32
<211> LENGTH: 72
<212> TYPE: DNA
<213> ORGANISM: Artificial Sequence
<220> FEATURE:
<223> OTHER INFORMATION: Description of Artificial Sequence: Deletion
      construct made of the melanotransferrin (p97) gene
<221> NAME/KEY: CDS
<222> LOCATION: (1)..(69)

<400> SEQUENCE: 32 gac tac gtg gcg gcg ctg gaa ggg atg tcg tct cag cag tgc tcg ggc      48
Asp Tyr Val Ala Ala Leu Glu Gly Met Ser Ser Gln Gln Cys Ser Gly
 1               5                  10                  15 gca gcg gcc ccg gcg ccc atc tga                                      72
Ala Ala Ala Pro Ala Pro Ile
            20

<210> SEQ ID NO 33
<211> LENGTH: 23
<212> TYPE: PRT
<213> ORGANISM: Artificial Sequence
<220> FEATURE:
<223> OTHER INFORMATION: :

<400> SEQUENCE: 33

Asp Tyr Val Ala Ala Leu Glu Gly Met Ser Ser Gln Gln Cys Ser Gly
 1               5                  10                  15

```
Ala Ala Ala Pro Ala Pro Ile
            20

<210> SEQ ID NO 34
<211> LENGTH: 69
<212> TYPE: DNA
<213> ORGANISM: Artificial Sequence
<220> FEATURE:
<223> OTHER INFORMATION: Description of Artificial Sequence:Deletion
      construct made of the melanotransferrin (p97) gene
<221> NAME/KEY: CDS
<222> LOCATION: (1)..(66)

<400> SEQUENCE: 34 gac tac gtg gcg gcg ctg gaa ggg atg tcg tct cag cag tgc tcg ggc      48
Asp Tyr Val Ala Ala Leu Glu Gly Met Ser Ser Gln Gln Cys Ser Gly
  1               5                  10                  15 gca gcg gcc cca tct gac taa                                          69
Ala Ala Ala Pro Ser Asp
            20

<210> SEQ ID NO 35
<211> LENGTH: 22
<212> TYPE: PRT
<213> ORGANISM: Artificial Sequence
<220> FEATURE:
<223> OTHER INFORMATION: :

<400> SEQUENCE: 35

Asp Tyr Val Ala Ala Leu Glu Gly Met Ser Ser Gln Gln Cys Ser Gly
  1               5                  10                  15

Ala Ala Ala Pro Ser Asp
            20

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence:Deletion
      construct made of the melanotransferrin (p97) gene
<221> NAME/KEY: CDS
<222> LOCATION: (1)..(18)

<400> SEQUENCE: 36 gac tac gtg gcg gcg atc tga                                          21
Asp Tyr Val Ala Ala Ile
  1               5

<210> SEQ ID NO 37
<211> LENGTH: 6
<212> TYPE: PRT
<213> ORGANISM: Artificial Sequence
<220> FEATURE:
<223> OTHER INFORMATION: :

<400> SEQUENCE: 37

Asp Tyr Val Ala Ala Ile
  1               5

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence:Deletion
      construct made of the melanotransferrin (p97) gene
```

```
<221> NAME/KEY: CDS
<222> LOCATION: (1)..(24)

<400> SEQUENCE: 38 gac tac gtg gat ctg act aaa tct tag                           27
Asp Tyr Val Asp Leu Thr Lys Ser
  1               5

<210> SEQ ID NO 39
<211> LENGTH: 8
<212> TYPE: PRT
<213> ORGANISM: Artificial Sequence
<220> FEATURE:
<223> OTHER INFORMATION: :

<400> SEQUENCE: 39

Asp Tyr Val Asp Leu Thr Lys Ser
  1               5

<210> SEQ ID NO 40
<211> LENGTH: 29
<212> TYPE: PRT
<213> ORGANISM: Artificial Sequence
<220> FEATURE:
<223> OTHER INFORMATION: Description of Artificial Sequence:Chicken p97
      homolog

<400> SEQUENCE: 40

Cys Ser Gly Ala Gly Asn Lys Leu Ile Gln Gln His Leu Leu Val Ile
  1               5                  10                  15

Thr Phe Val Pro Phe Ile Ile Leu Gly Gln Leu Gln Gly
             20                  25

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence:Chicken p97
      homolog

<400> SEQUENCE: 41

Cys Ser Gly Ala Val Ser Pro Glu Leu Cys Phe Gln Lys Arg
  1               5                  10

<210> SEQ ID NO 42
<211> LENGTH: 56
<212> TYPE: DNA
<213> ORGANISM: Artificial Sequence
<220> FEATURE:
<223> OTHER INFORMATION: Description of Artificial Sequence: Rescued
      P-element end

<400> SEQUENCE: 42
cgacgggacc accttatgtt atttcatcat gggccagacc cacgtagtcc agcggc      56

<210> SEQ ID NO 43
<211> LENGTH: 56
<212> TYPE: DNA
<213> ORGANISM: Artificial Sequence
<220> FEATURE:
<223> OTHER INFORMATION: Description of Artificial Sequence: Rescued
      P-element end

<400> SEQUENCE: 43
cgacgggacc accttatgtt atttcatcat gtctcgaacc aacgagagca gtatgc      56
```

```
<210> SEQ ID NO 44
<211> LENGTH: 56
<212> TYPE: DNA
<213> ORGANISM: Artificial Sequence
<220> FEATURE:
<223> OTHER INFORMATION: Description of Artificial Sequence: Rescued
      P-element end

<400> SEQUENCE: 44
cgacgggacc accttatgtt atttcatcat ggtacagaca tctacttccc cccgct        56

<210> SEQ ID NO 45
<211> LENGTH: 56
<212> TYPE: DNA
<213> ORGANISM: Artificial Sequence
<220> FEATURE:
<223> OTHER INFORMATION: Description of Artificial Sequence: Rescued
      P-element end

<400> SEQUENCE: 45
cgacgggacc accttatgtt atttcatcat gatcttgcgc tttaaaatgt ggagtc        56

<210> SEQ ID NO 46
<211> LENGTH: 56
<212> TYPE: DNA
<213> ORGANISM: Artificial Sequence
<220> FEATURE:
<223> OTHER INFORMATION: Description of Artificial Sequence: Rescued
      P-element end

<400> SEQUENCE: 46
cgacgggacc accttatgtt atttcatcat ggtctggcca ttctcatcgt gagctt        56

<210> SEQ ID NO 47
<211> LENGTH: 56
<212> TYPE: DNA
<213> ORGANISM: Artificial Sequence
<220> FEATURE:
<223> OTHER INFORMATION: Description of Artificial Sequence: Rescued
      P-element end

<400> SEQUENCE: 47
cgacgggacc accttatgtt atttcatcat gagccaaaca gaaagcagaa aagctc        56

<210> SEQ ID NO 48
<211> LENGTH: 56
<212> TYPE: DNA
<213> ORGANISM: Artificial Sequence
<220> FEATURE:
<223> OTHER INFORMATION: Description of Artificial Sequence: Rescued
      P-element end

<400> SEQUENCE: 48
cgacgggacc accttatgtt atttcatcat ggcctgacct aagcagattt gactgc        56

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Rescued
      P-element end

<400> SEQUENCE: 49
cgacgggacc acctt        15
```

```
<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Rescued
      P-element end

<400> SEQUENCE: 50
caacgctacc taatcttaag aacca                                              25
```